United States Patent
Tajima et al.

(10) Patent No.: US 8,309,109 B2
(45) Date of Patent: Nov. 13, 2012

(54) COSMETIC AND METHOD FOR PRODUCTION THEREOF

(75) Inventors: Kazuo Tajima, Yokohama (JP); Yoko Imai, Tokyo (JP); Teruo Horiuchi, Sayama (JP); Yasuhiro Nohata, Yokkaichi (JP)

(73) Assignees: Hakuto Co., Ltd., Tokyo (JP); Kanagawa University, Kanagawa (JP)

( * ) Notice: Subject to any disclaimer, the term of this patent is extended or adjusted under 35 U.S.C. 154(b) by 596 days.

(21) Appl. No.: 12/308,876

(22) PCT Filed: Jun. 29, 2007

(86) PCT No.: PCT/JP2007/063145
§ 371 (c)(1),
(2), (4) Date: Dec. 29, 2008

(87) PCT Pub. No.: WO2008/001902
PCT Pub. Date: Jan. 3, 2008

(65) Prior Publication Data
US 2009/0280149 A1 Nov. 12, 2009

(30) Foreign Application Priority Data
Jun. 30, 2006 (JP) ................. 2006-182306

(51) Int. Cl.
*A61K 8/06* (2006.01)
(52) U.S. Cl. ................... 424/401; 536/123.1
(58) Field of Classification Search .......... None
See application file for complete search history.

(56) References Cited

U.S. PATENT DOCUMENTS
5,670,139 A * 9/1997 Allard et al. ............ 424/59
(Continued)

FOREIGN PATENT DOCUMENTS
EP 1 486 193 A1 12/2004
(Continued)

OTHER PUBLICATIONS
Machine translation of EP 1500385, description only (accessed Apr. 26, 2011).*

*Primary Examiner* — Daniel Sullivan
*Assistant Examiner* — Barbara Frazier
(74) *Attorney, Agent, or Firm* — McGinn IP Law Group, PLLC

(57) ABSTRACT

A cosmetic in an emulsified state, in which a titanium dioxide microparticle coated with hydrous silicic acid and/or a hydrous silicate compound, a higher alcohol, an oily component other than the higher alcohol, and a polysaccharide are contained, and the polysaccharide containing at least one of fucose, glucose, glucuronic acid and rhamnose as a constituent monosaccharide, and having fucose and/or rhamnose in a side chain is contained in an amount of 0.01% by weight to 1% by weight relative to the total amount of the cosmetic. And a cosmetic containing the higher alcohol, the oily component and the polysaccharide in an emulsified state, in which the higher alcohol is composed of two or more kinds of higher alcohols having different molecular weights, and is contained in the cosmetic in an amount of 1% by weight to 20% by weight relative to the total amount of the cosmetic. The oily component is contained in an amount of 1% by weight to 20% by weight relative to the total amount of the cosmetic, and the polysaccharide is contained in an amount of 0.01% by weight to 1% by weight relative to the total amount of the cosmetic, and a producing method thereof.

6 Claims, 1 Drawing Sheet

U.S. PATENT DOCUMENTS

2008/0031906 A1 * 2/2008 Nohata et al. ................. 424/401

FOREIGN PATENT DOCUMENTS

| | | | |
|---|---|---|---|
| EP | 1 500 385 A1 | | 1/2005 |
| EP | 1500385 | * | 1/2005 |
| EP | 1 820 538 A1 | | 8/2007 |
| JP | 2007-8901 | | 1/2007 |
| JP | 2007-238516 | | 9/2007 |
| WO | WO 2006/028012 | * | 3/2006 |

* cited by examiner

COSMETIC AND METHOD FOR PRODUCTION THEREOF

TECHNICAL FIELD

The present invention relates to a cosmetic capable of stably dispersing and emulsifying titanium dioxide microparticles of which surfaces are coated with hydrous silicic acid and a compound thereof, blending into skin, exhibiting excellent water resistance, and providing good touch.

In addition, the present invention relates to a cosmetic capable of maintaining an emulsified state with storage stability, and providing smooth touch without adding any organic substance generally classified as a surfactant, and irrespective of the kinds of a component to be emulsified, and a method for producing such a cosmetic.

BACKGROUND ART

Recently, it has been stated that ultraviolet rays accelerate skin aging, and in order to protect skin from ultraviolet rays, cosmetics and skin care products for external use, each containing an ultraviolet rays absorber and a ultraviolet rays scattering agent, have been frequently used. Titanium dioxide, in particular, titanium dioxide microparticles, are mainly used as the ultraviolet rays scattering agent. Various shapes such as a solid powder, milky lotion, oil, etc. are blended according to objects thereof. Most of these sun care products are W/O type emulsified cosmetics using surfactants.

The ultraviolet rays care effect of the sun care product compositions is mainly obtained by reflecting ultraviolet rays with titanium dioxide microparticles contained in the cosmetics. Therefore, in order to reflect ultraviolet rays more efficiently, the cosmetics containing titanium dioxide are required to become homogeneous on skin after applied, and keep that state. Generally, emulsion type cosmetics have features that the water content after applied evaporates or penetrates through skin, and a remaining oily component and dispersed titanium dioxide remain on skin homogeneously and closely adhere thereto.

The emulsion type cosmetic, however, contains a surfactant in order to emulsify components thereof, so that, when sweating, sweat and the surfactant blend into each other, and further, the surfactant, oily component and titanium dioxide blend into each other. Consequently, the homogeneity of titanium dioxide on skin is degraded with sweat. When the homogeneity is thus degraded, and titanium dioxide becomes inhomogeneous on skin, the reflectance of the ultraviolet rays remarkably drops so that the operation as the ultraviolet care cosmetic cannot be achieved.

Under the above circumstances, many sun care product compositions adopt a W/O type emulsion, and by mixing a high viscosity silicone that is difficult to blend with the surfactant, the surfactant locally exists inside the W/O type sun care product composition, whereas the high viscosity silicone locally exists in an outermost part thereof, and consequently, the surfactant is prevented from blending with sweat. Thus, the water resistance of the sun care product composition is improved, and even if sweating, the homogeneity of titanium dioxide on skin is maintained, and consequently, the ultraviolet rays care effect continues for a sufficient period of time.

However, when the water resistance is improved in this manner, the cosmetic becomes difficult to be washed away by normal washing methods using soaps and face cleansing foams. And in order to remove the sun care product compositions, they have been wiped out by oils for use in wiping, and then washed away using soaps or face cleansing foams.

Where general adult women use the sun care product compositions on their faces, by cleansing them with the above-described two steps, troubles caused by remaining sun care product compositions can be reduced, but where the ultraviolet rays protective cosmetics are applied to arms and foots, or children use the same, in many cases, the ultraviolet rays protective cosmetics have been tried to remove only by washing with soaps, and consequently, it has been difficult to remove the ultraviolet rays protective cosmetics sufficiently. As a result, it becomes insufficient to clean the ultraviolet rays protective cosmetics so that they remain in pores, etc. in skin, to cause rough skin, skin eruptions, etc. In addition, as described above, the conventional ultraviolet rays protective cosmetics have been intended to improve the water resistance, while sacrificing the readily washing properties thereof, so that many of the ultraviolet rays protective cosmetics have exhibited good water resistance, but have not been readily washed away.

Under the above circumstances, O/W type cosmetics which are emulsified with an emulsifying method using no surfactant have been considered as the cosmetics which are readily washed away with a normal washing method using soaps and cleansing foams. The technique of emulsifying oily components by use of the technique such as nanodispersion, etc. has been known as the emulsifying method without using any surfactant (see Non patent documents 5, 6 and Patent document 1, for example). This technique means the three-phase emulsifying method of carrying out emulsification by making nanoparticles of polysaccharide, which exist in a system of oil/amphipathic chemical compound/water as an independent phase adhere to surfaces of oily components with van der Waals' force. This emulsification is excellent as the emulsifying method with which the emulsion stability of the components to be emulsified, such as oily components, etc. is maintained for a long period of time without adding any surfactant or any substance exhibiting substantially surface active performance.

However, the emulsion-dispersing of the titanium dioxide microparticles, which serves to achieve the ultraviolet rays protective effect, has not been sufficient. The reason is that the titanium dioxide microparticle blended in the cosmetics has light activity so that in order to prevent the titanium dioxide microparticle from directly contacting skin for improving safety, the surface of the titanium dioxide microparticle has been coated with various kinds of inorganic compounds and organic compounds.

Many kinds of chemical compounds have been used for coating, and examples thereof include aluminum hydroxide, stearic acid, hydrous silicic acid, dimethylpolysiloxane, methyl-hydrogen-polysiloxane, etc. By blending titanium dioxide subjected to the surface treatment with these chemical compounds, for example, with polysaccharide to be used in the present invention, cosmetics exhibiting ultraviolet rays preventive actions and good touch can be obtained, but, where the constituent monosaccharide of the above-described polysaccharide is glucuronic acid having carboxyl groups, the available surface treatment for titanium dioxide is limited.

Namely, when polyhydric metal ions or polyhydric metal ion chemical compounds are contained in the surface treatment of titanium dioxide, metal ions dissolve out with time, even if a very small amount is contained. The dissolved polyhydric metal ions combine with carboxyl groups of the polysaccharide to provide aggregation to the polysaccharide. The polysaccharide having aggregating power gradually become tight, the cosmetics homogeneously emulsified become solid, and water may be separated therefrom. And, if polyhydric metal is not contained as a surface treating agent, similar phenomena may occur where a polyhydric metal-based surface treating agent is used in the surface treatment step, and a residue thereof is intermixed therein.

Therefore, in the surface treatment step of titanium dioxide, sodium silicate solution is directly reacted with titanium dioxide powder. Otherwise, it becomes necessary to use a titanium dioxide microparticle subjected to the heat treatment, which does not contain polyhydric metal, by using the method of performing the surface treatment with hydrous silicic acid and a hydrous silicate compound after the surface treatment with methyl-hydrogen-polysiloxan.

The cosmetic contains various many components according to the kind thereof, and, for example, contains organic solvents, oils, moisturizer, astringents, bleaching agents, UV preventive agents, oxidation preventive agents and perfumes as oily components. The oily components have the cleaning effect, water-retaining effect, emollient effect and protective effect against skin, and perform the functions of improving the spreading ability, smooth feeling, glossiness, adhering properties, etc. of the cosmetic.

Where the oily components as components to be emulsified, which are contained in this cosmetic, are used in the cosmetic, conventionally, these components have been emulsified and dispersed in purified water, using surfactants.

In the case of the oily components, the surfactants have been selected according to required HLB values thereof and characteristics of surfaces of granules, and the emulsification and dispersion have been carried out using many kinds of surfactants. The required HLB values of the surfactants adapted to be used as an emulsion-dispersing agent must be made different between the case of oil-in water (O/W) emulsions being produced and the case of water-in-oil (W/O) emulsions being produced, and the thermal stability and storage stability are not sufficient so that many and various kinds of surfactants have been used as a mixture thereof (see Non patent documents 1 through 4, for example).

The conventional emulsifying method using surfactants is based on the technique of adsorbing surfactants on interfaces between oil and water to decrease surface energy therein so that a large amount of emulsifiers (surfactants) have been needed to reduce an interfacial tension thereof.

The surfactants, however, are low in biodegradation to cause bubbling, and accordingly, exhibit the problems such as environmental pollution so that the reduction of the amount of the surfactants has been required.

And emulsifiers for oily components have been generally prepared by physicochemical emulsifying methods such as the HLB method, phase inversion emulsifying method, phase transition temperature emulsifying method, gel emulsifying method, etc., and in these methods, the emulsions have been prepared by decreasing surface energies in oil/water interfaces to stabilize systems thermodynamically. Therefore, in order to select the emulsifiers mostly suited to the cosmetics, very troublesome and lots works have been needed, and since, in the cosmetics, many kinds of oily components are mixed therein, stable emulsification thereof has been frequently difficult.

In addition, the cosmetics are required to exhibit many and various effects so that it is needed to stabilize many substances (components to be emulsified) exhibiting various surfacial tensions in a single cosmetic. In particular, silicone oil is chemically stable, safe with substantially no reactivity, odorless with little stickiness, has a low surface tension with good spreading ability, and has smooth feeling so that it has been blended in many cosmetics such as creams, milky lotions, lotions, gels, etc.

However, since silicone oil is very hydrophobic and the interfacial tension thereof is low, it has been difficult to stabilize silicone oil in aqueous solutions. And where the surfactants adapted to emulsify silicone oil are used, there has occurred the problem that emulsification of organic acids such as stearic acid, etc. and higher alcohols such as cetanol, etc. becomes instable, and in the case of the substances such as titanium dioxide particles and iron oxide particles, of which surfacial tensions are extremely different from that of organic compounds being used in the cosmetic, there has occurred the problem that emulsification becomes more difficult.

And when a large amount of oily component is intermixed with water, there occurs a phase transition in "type" of the emulsion, and where the surfactant is used, an oily component phase and a water phase may separate from each other.

Under the above circumstances, in order to solve the problems concerning the emulsification with the use of surfactant, the technique of emulsifying oily components without adding any surfactant using the technique such as nanodispersion, etc. has been known (see Non patent documents 5, 6 and Patent Document 1, for example).

This technique means the three-phase emulsifying method of carrying out emulsification by making a nanoparticle that exists in a system of oil/amphipathic chemical compound/water as an independent phase adhere to a surface of an oily component with van der Waals' force. This emulsification is excellent as the emulsifying method, because no surfactant (including substance having a substantially surface active performance) is added, and the emulsion stability of the components to be emulsified, such as the oily component, etc. is maintained for a long period of time.

However, the cosmetics prepared by using this technique were bad feelings so as not to be practical. Namely, when the cosmetics are used actually, as shown in FIG. 1, the oily components deform due to pressure of fingers, etc. and friction forces against skin upon applying them to the skin, and consequently, van der Waals' force between nanoparticles and the oily components decreases or disappears, whereby the nanoparticles separate from surface of the oily component. As a result, the oily components dispersed coalesce with each other on skin to become large oil drops to separate from water. The thus separated oily components exist on skin as drops to degrade the skin absorbent. Therefore, in order to improve the blending properties into skin of the cosmetics prepared by the three-phase emulsifying method, surfactants or chemical compounds having substantially surface-active effect, such as phospholipid including hydrogenated lecithin, ceramido derivative including sphingolipid have been added so that the cosmetics containing no surfactant have not been able to be produced.

Non patent document 1: "Emulsion Science" Edited by P Sherman, Academic PressInc. (1969)

Non patent document 2: "Microemulsions-Theory and Practice-Edited by Leon M. price, Academic Press Inc. (1977)

Non patent document 3: "Technique of Emulsification and Solubilization" edited by Susumu Tsuji, Kougakutosho Ltd. (1976)

Non patent document 4: "Developing Technique of Functional Surfactants" published by CMC Publishing Co., Ltd. (1998)

Non patent document 5: Abstract of The 43$^{rd}$ Annual Meeting of the Japan Oil Chemists' Society, Oosaka University, Convention Center (Nov. 1-Nov. 2, 2004)

Non patent document 6: Abstract of The 57th Meeting on Colloid and Interface Chemistry of The Chemical Society of Japan (Sep. 9-Sep. 11, 2004)

Patent document 1: Patent application laid open No. 2004-130300

DISCLOSURE OF THE INVENTION

Problems to be Solved by the Invention

In order to solve these problems, the present inventors have an object of providing an ultraviolet rays protective cosmetic which contains no oily component difficult to blend with soap, etc., such as a surfactant and high viscosity silicone, and consequently, providing an sun care product composition which exhibits a sufficient water resistance and is readily washed away, and a production method thereof.

In addition, they have found that by adding a specific polysaccharide and a specific higher alcohol, emulsifying at 70° C. or more, and cooling them to 40° C. while agitating, cosmetics in the emulsified state, which preferably blend into skin, can be obtained.

Furthermore, the present inventors have studied intensively to develop cosmetics prepared using a novel emulsifying technique in the emulsifying method of oily components. As a result, they have found that the cosmetics in the emulsified state, which blend into skin, are prepared by mixing a specific polysaccharide and two or more kinds of specific higher alcohols, emulsifying them at 70° C. or more, and cooling them to 40° C. while agitating. And, they have found that by selecting specific oily components out of the oily components, classifying them to two groups, and adding one or more kinds of the oily components from each of the two groups, the emulsion system thereof is drastically stabilized, and have completed the present invention based on these findings. The cosmetics in accordance with the present invention do not contain any surfactant (inclusive of any substance having a substantially surface active performance), and the emulsion stability of components to be emulsified, such as oily components thereof, is maintained over a long period of time.

Under the above-described circumstances, the object of the present invention is to provide a cosmetic in which an emulsion excellent in thermal stability and storage stability is formed by selecting and mixing a specific polysaccharide, two or more kinds of higher alcohols, each having a melting point of 45° C. or more, and one or more kinds of oily components selected out of each of two classified groups, and which exhibits good feelings in use, and to provide a producing method of this cosmetic.

Means for Solving the Problems

The present invention according to claim 1 provides an emulsified cosmetic characterized in that in the cosmetic containing a higher alcohol, an oily component other than the higher alcohol, and a polysaccharide in an emulsified state, a titanium dioxide microparticle of which a surface is coated with hydrous silicic acid and/or a hydrous silicate compound is contained, the oily component is contained in an amount of 1% by weight to 20% by weight relative to the total amount of the cosmetic, and
the polysaccharide contains at least one of fucose, glucose, glucuronic acid and rhamnose as a constituent monosaccharide, and has fucose and/or rhamnose in a side chain, and the polysaccharide is contained in an amount of 0.01% by weight to 1% by weight relative to the total amount of the cosmetic.

In accordance with the present invention of claim 1, there is provided with a titanium dioxide microparticle of which a surface is coated with hydrous silicic acid and/or a hydrous silicate compound. Hydrous silicic acid and/or a hydrous silicate compound are substances having lest reactive to the polysaccharide including glucuronic acid having carboxyl groups as constituent components thereof. Therefore, by virtue of titanium dioxide subjected to the surface treatment with this hydrous silicic acid and/or a hydrous silicate compound, aggregation due to the polysaccharide dispersed in the cosmetic is difficult to occur, so that high stability thereof in the cosmetic can be obtained.

The cosmetic of the present invention contains a higher alcohol, an oily component other than the higher alcohol, and a polysaccharide, and the polysaccharide containing at least one of fucose, glucose, glucuronic acid and rhamnose as a constituent monosaccharide, and having fucose and/or rhamnose in a side chain is contained in an amount of 0.01% by weight to 1% by weight relative to the total amount of the cosmetic. Consequently, nanoparticles of the polysaccharide, which are randomly dispersed in the cosmetic, can be made to adhere to the surface of the oily component with van der Waals' force, and this oily component can be emulsified by the three-phase emulsifying method. Therefore, it is unnecessary to add any surfactant (inclusive of any substance having substantially surface acting performance) in the cosmetic, whereby the emulsification stability of a component to be emulsified, such as the oily component, etc. can be maintained over a long period of time.

In accordance with the present invention of claim 2, in the cosmetic containing a higher alcohol, an oily component and a polysaccharide in an emulsified state, the higher alcohol contains two or more kinds of higher alcohols, each having a melting point of 45° C. or more, and is contained in an amount of 1% by weight to 20% by weight relative to the total amount of the cosmetic, the oily component is contained in an amount of 1% by weight to 20% by weight relative to the total amount of the cosmetic, and the polysaccharide containing at least one of fucose, glucose, glucuronic acid and rhamnose as a constituent monosaccharide, and having fucose and/or rhamnose in a side chain is contained in an amount of 0.01% by weight to 1% by weight relative to the total amount of the cosmetic.

In accordance with the present invention of claim 2, two or more kinds of higher alcohols, each having a melting point of 45° C. or more, are contained in an amount of 1% by weight to 20% by weight relative to the total amount of the cosmetic. When two or more kinds of higher alcohols, each having a melting point of 45° C. or more, are contained, the size of aggregates of the higher alcohols and polysaccharide becomes inhomogeneous so that the crystallization thereof becomes difficult, whereby the emulsification becomes more stable. When only one kind of higher alcohol is contained, the emulsification can be performed, but, when allowed to stand at elevated temperatures such as 40° C., water separates therefrom. It is considered that when one kind of higher alcohol is used, the higher alcohol becomes a regular state (liquid crystal state) between other oil and water, the aggregates have gradually changed to crystals with time, and consequently, leaved the water.

If the amount of the higher alcohol is 1% by weight or less relative to the total amount of the cosmetic, sufficient emulsification is not obtained. Even if the amount is 20% by weight or more, stable emulsification is possible, but the higher alcohol of the present invention has a melting point of 45° C. so that when the composition ratio thereof is increased, the amount of the components that are at normal temperature or more increases to make the touch of the cosmetic hard after application, thereby degrading feeling upon using.

The oily component is contained in an amount of 1% by weight to 20% by weight relative to the total amount of the cosmetic. When the amount of the oily component is 1% by weight or less, sufficient smoothness as the cosmetic cannot be provided against skin, whereas when the amount of the oily component is 20% by weight or more, a stable emulsified state cannot be obtained with the higher alcohol and the polysaccharide in accordance with the present invention.

The polysaccharide composed of at least one of fucose, glucose, glucuronic acid and rhamnose as a constituent monosaccharide, and having fucose and/or rhamnose in a side chain is contained in an amount of 0.01% by weight to 1% by weight relative to the total amount of the cosmetic. Where the later-describing specific polysaccharide and higher alcohol are used, a quasi-active agent having hydrophilic properties and hydrophobic properties is formed, and this quasi-active agent enables the oily component to be emulsified stably. When the amount of this polysaccharide is 0.01% by weight or less, sufficient stability cannot be obtained, whereas when 1% by weight or more, improvement of the stability performance corresponding to the addition amount is not effected, which is less preferable in cost.

The present invention according to claim 3 is a cosmetic in an emulsified state, which contains a titanium dioxide microparticle, wherein the titanium dioxide microparticle coated with hydrous silicic acid and/or a hydrous silicate compound is prepared by directly subjecting a titanium dioxide microparticle to a surface treatment with hydrous silicic acid and/or a hydrous silicate compound, or by subjecting a titanium dioxide microparticle to a surface treatment with methyl-hydrogen-polysiloxane, and then, subjecting it to a surface treatment with hydrous silicic acid and a hydrous silicate compound.

In accordance with the present invention of claim 3, the titanium dioxide microparticle coated with hydrous silicic acid and/or a hydrous silicate compound is prepared by directly subjecting a titanium dioxide microparticle to a surface treatment with hydrous silicic acid and/or a hydrous silicate compound, or by subjecting a titanium dioxide microparticle to a surface treatment with methyl-hydrogen-polysiloxane, and then subjecting it to a surface treatment with hydrous silicic acid and/or a hydrous silicate compound. Consequently, polyvalent metal does not remain on a surface of the titanium dioxide microparticle, and by using the titanium dioxide microparticle subjected to the surface treatment, intermixing of components adapted to add a plus electrical charge is restrained so that nanoparticles of randomly granulate polysaccharide do not generate any aggregating force, whereby the emulsified state of the cosmetic can be made more stable.

The present invention according to claim 4 is a cosmetic in an emulsified state, wherein the titanium dioxide microparticle coated with hydrous silicic acid and/or a hydrous silicate compound contains a titanium dioxide microparticle containing substantially no aluminum nor aluminum compounds.

In accordance with the present invention of claim 4, the titanium dioxide microparticle coated with hydrous silicic acid and/or a hydrous silicate compound contains the titanium dioxide microparticle containing substantially no aluminum nor aluminum compounds. Consequently, nanoparticles of randomly granulated polysaccharide do not generate any aggregating force, whereby the emulsified state of the cosmetic can be made more stable.

The present invention according to claim 5 is a cosmetic in an emulsified state, wherein the titanium dioxide microparticle coated with hydrous silicic acid and/or a hydrous silicate compound is contained in an amount of 1% by weight to 20% by weight relative to the total amount of the cosmetic, the higher alcohol is contained in an amount of 1% by weight to 15% by weight relative to the total amount of the cosmetic, and the oily component other than the higher alcohol in an amount of 0.5% by weight to 30% by weight relative to the total amount of the cosmetic.

In accordance with the present invention of claim 5, the titanium dioxide microparticle is contained in an amount of 1% by weight to 20% by weight relative to the total amount of the cosmetic so that the cosmetic exhibits sufficient ultraviolet rays preventive effect. When the amount is 1% by weight or less, the ultraviolet rays preventive effect is not sufficient, whereas even if 20% by weight or more is contained, effect corresponding to the increment thereof cannot be expected, so as to be less preferable in cost.

The higher alcohol is contained in an amount of 1% by weight to 15% by weight relative to the total amount of the cosmetic, and the oily component other than the higher alcohol is contained in an amount of 0.5% by weight to 30% by weight relative to the total amount of the cosmetic. Therefore, the oily component is sufficiently emulsified. Where the higher alcohol is contained in an amount of 1% by weight or less relative to the total amount of the cosmetic, sufficient emulsification is not effected, whereas where 15 weight % by weight or more is contained, stable emulsification is possible, but as the composition ratio increases, the components at normal temperature or more increases, thereby hardening touch of the cosmetic after application, and consequently, feeling upon using is degraded.

The oily component other than the higher alcohol is contained in an amount of 0.5% by weight to 30% by weight relative to the total amount of the cosmetic. When the oily component is 0.5% by weight or less, sufficient smoothness sufficient as the cosmetic cannot be provided, whereas when 30% by weight or more is contained, stable emulsified state due to the higher alcohol and the polysaccharide in accordance with the present invention cannot be obtained.

The present invention according to claim 6 is a cosmetic in an emulsified state, in which two or more kinds of higher alcohols, each having a melting point of 45° C. or more, are contained as the higher alcohol.

In accordance with the present invention of claim 6, two or more kinds of higher alcohols, each having a melting point of 45° C. or more, are contained as the higher alcohol so that the size of aggregates of the higher alcohols and the polysaccharide becomes inhomogeneous so that crystallization thereof becomes difficult, whereby the emulsification becomes more stable. When only one kind of the higher alcohol is contained, the emulsification can be performed, but, when allowed to stand at elevated temperatures such as 40° C., water separates therefrom. It is considered that when one kind of the higher alcohol is used, the higher alcohol becomes a regular state (liquid crystal state) between other oil and water, the aggregates have gradually changed to crystals with time, and consequently, water emitting phenomena occurs.

And, by further adding two or more kinds of higher alcohols, each having a melting point of 45° C., the cosmetic well blends into skin, and the stability is further improved.

The present invention according to claim 7 is a cosmetic in an emulsified state, wherein the mixing ratio of the two or more kinds of higher alcohols is such that the mixing ratio of a higher alcohol of which the content is a maximum and a higher alcohol of which the content is a minimum ranges from 1:1 to 5:1.

In accordance with the present invention of claim 7, the mixing ratio of the two or more kinds of higher alcohols is such that the mixing ratio of a higher alcohol of which the content is a maximum and a higher alcohol of which the content is a minimum ranges from 1:1 to 5:1 so that, in the two or more kinds of mixed higher alcohols, one higher alcohol is mixed in the ratio of at least one fifth relative to the other one higher alcohol, and consequently, aggregates of the higher alcohols having different molecular weights and the polysaccharide form a substantially corresponding amount of aggregates, each having different sizes, thereby preventing the formation of a homogeneous particulate structure, and consequently, enabling the stabilization of the emulsified state.

The present invention according to claim 8 is a cosmetic in an emulsified state, wherein the higher alcohol is composed of two or more kinds of higher alcohols selected from hexadecanol, octadecanol, eicosanol and docosanol, each of the selected two or more kinds of the higher alcohols is contained in an amount of 0.4% by weight or more relative to the total amount of the cosmetic, and the total of the selected two or more kinds of the higher alcohols is contained in an amount of 0.8% by weight to 20% by weight relative to the total amount of the cosmetic.

In accordance with the present invention of claim 8, the above-described specific two or more kinds of the higher alcohols are used, and consequently, a plurality of chemical compounds, each having hydroxyl groups, are contained, so that the aggregates generated from the polysaccharide and higher alcohols have various sizes, thereby preventing the aggregates of the higher alcohols having different molecular weights and the polysaccharide from forming a homogeneous particulate structure, and consequently, enabling the stabilization of the emulsified state.

In addition, if each higher alcohol is not used in an amount of 0.4% by weight or more, the effect due to the use of two or more kinds of the higher alcohols cannot be sufficiently effected. And, when the amount of a mixture of two or more kinds of higher alcohols is 0.8% by weight or less relative to the total amount of the cosmetic, a sufficient particulate structure cannot be formed with the polysaccharide, whereas even when 20% by weight or more is intermixed, the effect corresponding to the intermixing content is not achieved, which is not preferable in cost.

The present invention according to claim 9 is a cosmetic in an emulsified state, wherein the cosmetic contains one or more kinds of the materials selected from the groups of tripotassium phosphate, trisodium phosphate, potassium metaphosphate, sodium metaphosphate, sodium pyrophosphate, sodium tripolyphosphate, sodium tetrapolyphosphate, sodium pentapolyphosphapte, potassium pyrophosphate, potassium tripolyphosphate, potassium tetrapolyphosphate, potassium pentapolyphosphate, citric acid, sodium citrate, potassium citrate, hydroxyethane diphosphonic acid, and diethylenetriamine pentaacetic acid in an amount of 0.05% by weight to 5% by weight relative to the total amount of the cosmetic.

In accordance with the present invention of claim 9, the cosmetic contains one or more kinds of the materials selected from the groups of tripotassium phosphate, trisodium phosphate, potassium metaphosphate, sodium metaphosphate, sodium pyrophosphate, sodium tripolyphosphate, sodium tetrapolyphosphate, sodium pentapolyphosphapte, potassium pyrophosphate, potassium tripolyphosphate, potassium tetrapolyphosphate, potassium pentapolyphosphate, citric acid, sodium citrate, potassium citrate, hydroxyethane diphosphonic acid, and diethylenetriamine pentaacetic acid in an amount of 0.05% by weight to 5% by weight relative to the total amount of the cosmetic. Therefore, even if the component adapted to add a plus electrical charge is blended in the cosmetic, the above-described phosphates (ion), citrates (ion), phosphinous acid compounds (ion), acetic acid compounds (ion) speedily react to neutralize it, and make the apparent charge of the emulsion to a minus charge, whereby the stability of the emulsified state can be improved.

The present invention according to claim 10 is a cosmetic in an emulsified state, wherein the polysaccharide contains at least a polysaccharide represented by the following general formula (chemical 1).

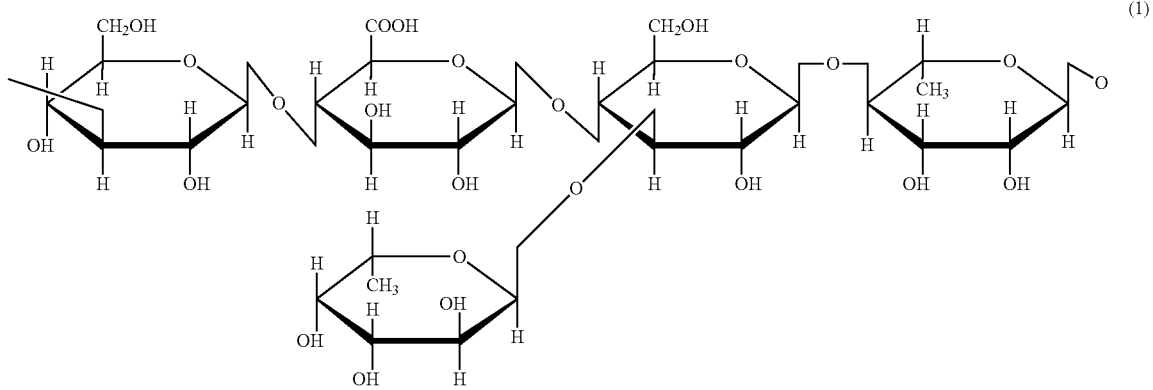

In accordance with the present invention of claim 10, at least the polysaccharide represented by the above-described general formula (1) is contained in the polysaccharide so that when components to be emulsified are emulsified with the polysaccharide represented by the above-described general formula (1) and two or more kinds of specific higher alcohols, the cosmetic in a stable emulsified state can be obtained. By using the above-described polysaccharide and two or more kinds of specified higher alcohols, the polysaccharide and the higher alcohols are bonded to each other with hydrogen bonds, and aggregates (clusters) are generated to form a particulate structure, whereby the cosmetic with a stable emulsified state can be obtained.

The present invention according to claim 11 is a cosmetic in an emulsified state, wherein the oily component contains at least an oily component (A) composed of at least one selected from the group consisting of silicone oil, fluorinated Hydrocarbon and derivatives thereof, hydrocarbon, fatty acid, fatty acid ester of monohydric alcohol, animal and vegetable oils, oxycarboxylic acid ester, fatty acid ester of polyhydric alcohol (melting point: 40° C. or less) and liquid wax an oily component (B) composed of at least one selected from the group consisting of solid wax, dihydric higher alcohol, cyclic alcohol and fatty acid ester thereof, fatty acid ester of polyhydric alcohol (melting point: 40° C. or less) and phospholipids
in a weight ratio of the oily component (A) to the oily component (B), which ranges from 2:1 to 50:1.

In accordance with the present invention of claim 11, by adding the oily component (A) that is liquid at normal temperature, and the oily component (B) that is solid or paste at normal temperature, and hydrous, smooth touch and finishing feel upon application, relieving of blocked feeling and improvement of touch after application, and improvement of feeling upon using are effected. The ratio of the content of the oily component (A) to the oily component (B) ranges from 2:1 to 50:1, preferably ranges from 3:1 to 30:1, and more preferably ranges from 5:1 to 10:1.

The present invention according to claim 12 preferably contains, as the oily component (A) that is liquid at normal temperature, dimethyl polysiloxan, trimethyl polysiloxan, squalane, paraffin; isopropyl palmitate, myristyl myristate, isostearyl myristate, glyceryl triethylhexanoate, glyceryl tricaplyrate.tricaprate, grape seed oil, rosa canina fruit oil, sunflower oil, olive fruit oil, avocado oil, macadamia ternifolia seed oil, meadowfoam seed oil, shea oil and jojoba seed oil, and one or more kinds of these materials can be used.

It is preferable that the oily component (B) that is solid or paste at normal temperature is composed of at least one selected from beeswax, hydrogenated jojoba oil, chimyl alcohol, batyl alcohol, cholesterol, cholesteryl stearate, phytosterol, glyceryl trimyristate and glyceryl tristearate, and one or more kinds of these materials can be used. By using this combination, the balance with the higher alcohol in accordance with the present invention becomes good, smoothness and penetrating feeling of the cosmetic upon application are good, and filmed feeling after application is improved.

In accordance with the present invention of claim 12, the method of classifying the oily components to two groups of the oily component (A) and the oily component (B), and selecting and combining at least one out of each of the groups has been found from experiences, and consequently, the reasons for the effect have not been sufficiently made clear.

The present invention according to claim 13 is a cosmetic in an emulsified state, which does not contain any one of a cationic surfactant, anionic surfactant, and nonionic surfactant composed of alkylene (carbon atoms: 2 to 4) oxide adduct.

In accordance with the present invention of claim 13, since the cosmetic does not contain any one of a cationic surfactant, anionic surfactant, and nonionic surfactant composed of alkylene (carbon atoms: 2 to 4) oxide adduct, emulsified substances that are stable over a long period of time, and well blending into skin can be obtained, whereby it is unnecessary to use any surfactant having substantially surface-acting performance, and consequently, a cosmetic well blending into skin without contaminating the surrounding environment, can be obtained. In addition, as the surfactant having substantially surface-acting performance is not used, a cosmetic with high safety, which exhibits water resistance and is capable of being washed away with general face cleansing and bathing, such as soap cleansing, etc., can be obtained.

The present invention according to claim 14 is a cosmetic in an emulsified state, wherein the polysaccharide is granulated to random particle diameters.

In accordance with the present invention of claim 14, since the polysaccharide is granulated to random particle diameters, a cosmetic wherein the emulsified state of the oily component is stable can be obtained.

The present invention according to claim 15 is a method for producing a cosmetic in an emulsified state, which contains a titanium dioxide microparticle, a higher alcohol, an oily component other than the higher alcohol and a polysaccharide, wherein
a titanium dioxide microparticle of which a surface is coated with hydrous silicic acid and/or a hydrous silicate compound is used as the titanium dioxide microparticle,
after preparing a solution by dissolving the polysaccharide containing at least one of fucose, glucose, glucuronic acid and rhamnose as a constituent monosaccharide, and having fucose and/or rhamnose in a side chain in water and/or a hydrophobic solvent at 70° C. or more in an amount of 0.01% by weight to 1% by weight relative to the total amount of the cosmetic,
the higher alcohol is added to the solution in an amount of 1 to 20% by weight relative to the total amount of the cosmetic to be dissolved, the oily component is added to the solution in an amount of 1 to 20% by weight relative to the total amount of the cosmetic to be dissolved, and the solution is emulsified and agitated at 70° C. or more, and
the solution containing emulsified and agitated components is cooled to 40° C. or less.

In accordance with the present invention of claim 15, first, the polysaccharides containing at least one of fucose, glucose, glucuronic acid and rhamnose as a constituent monosaccharide, and having fucose and/or rhamnose in a side chain is dissolved in water and/or a hydrophobic solvent at 70° C. or more in an amount of 0.01 to 1% by weight relative to the total amount of the cosmetic material to prepare a solution. Therefore, the solution of the polysaccharide enables randomly dispersed nanoparticles in the cosmetic to adhere to the surface of the oily component with van der Waals' force so that this oily component can be emulsified by the three-phase emulsifying method. Therefore, it is unnecessary to add any surfactant (inclusive of substances having substantially surface-acting performance) in the cosmetic, whereby the emulsification stability of components to be emulsified, such as the oily component, etc. can be maintained over a long period of time. By emulsifying the solution in which the polysaccharide, at least two kinds of higher alcohols and the above-described oily component are dispersed at 70° C. or more, the components to be emulsified can be emulsified stably.

The higher alcohol is added to the solution in an amount of 1% by weight to 20% by weight relative to the total amount of the cosmetic to be dissolved, and the oily component is added to the solution in an amount of 1% by weight to 20% by weight relative to the total amount of the cosmetic to be dissolved, and emulsified and agitated at 70° C. or more. Therefore, by virtue of the solution of the above-described polysaccharide, the oily component in the amount corresponding to 1% by weight to 20% by weight is sufficiently emulsified. When the higher alcohol is 1% by weight or less relative to the total amount of the cosmetic, sufficient emulsification cannot be obtained, whereas when 20% by weight or more, sufficient emulsification is possible, but when the composition ratio is increased, the amount of the components that are solid at normal temperature increases to make touch after application hard, whereby the feeling upon using is degraded.

Furthermore, the solution containing the emulsified and agitated components is cooled to 40° C. or less. By cooling a mixture of the above-described polysaccharide, two or more kinds of the higher alcohols and the oily component, which is dispersed in water and the hydrophilic solvent by emulsifying and agitating at 70° C. or more, to 40° C. or less, while continuously emulsifying and agitating in this state, this state can be fixed. Therefore, the cosmetic in accordance with the present invention has the state in which the oily component and water are dispersed specifically so that a cosmetic in an emulsified state, which well blends into skin, can be obtained. Where the mixture is cooled to 40° C. or less while being emulsified and agitated, the same agitating device can be used.

The present invention according to claim 16 is a method for producing a cosmetic containing a higher alcohol, an oily component other than the higher alcohol and a polysaccharide in a emulsified state, wherein after preparing a solution by dissolving the polysaccharide containing at least one of fucose, glucose, glucuronic acid and rhamnose as a constituent monosaccharide, and having fucose and/or rhamnose in a side chain in water and/or a hydrophobic solvent at 70° C. or more in an amount of 0.01% by weight to 1% by weight relative to the total amount of the cosmetic, the higher alcohol containing two or more kinds of higher alcohols, each having a melting point of 45° C. or more, is added to the solution in an amount of 1% by weight to 20% by weight relative to the total amount of the cosmetic to be dissolved, the oily component is added to the solution in an amount of 1 to 20% by weight relative to the total amount of the cosmetic to be dissolved, the solution is emulsified and agitated at 70° C. or more, and the solution containing emulsified and agitated components is cooled to 40° C. or less.

In accordance with the present invention of claim 16, first, the polysaccharide containing at least one of fucose, glucose, glucuronic acid and rhamnose as a constituent monosaccharide, and having fucose and/or rhamnose in a side chain is dissolved in water and/or a hydrophobic solvent at 70° C. or more in an amount of 0.01 to 1% by weight relative to the total amount of the cosmetic to prepare a solution.

Therefore, when the above-described specific polysaccharide and the higher alcohol to be added in the solution later are dissolved, a quasi-active agent having a hydrophilic part and a hydrophobic part is formed, and this quasi-active agent enables the oily component to be stably emulsified. When this polysaccharide is 0.01% by weight or less, sufficient stability cannot be effected, whereas when the amount is 1% by weight or more, the improvement of the stability performance corresponding to the addition amount is not obtained so as to be less preferable in cost.

Next, the higher alcohol containing two or more kinds of higher alcohols, each having a melting point of 45° C. or more, is added to the solution in an amount of 1% by weight to 20% by weight relative to the total amount of the cosmetic, and the oily component is added to the solution in an amount of 1% by weight to 20% by weight relative to the total amount of the cosmetic, and they are dissolved. The higher alcohol in accordance with the present invention is dispersed in a dispersion liquid of the polysaccharide, in which the polysaccharide is sufficiently dispersed, and two or more kinds of higher alcohols, each having a melting point of 45° C. or more, are contained in the solution so that the size of the particles composed of the higher alcohols and the polysaccharide becomes inhomogeneous, and the emulsified particles containing the oily component become difficult to be crystallized, whereby the emulsification becomes more stable. The stable emulsification cannot be obtained with only one kind of these materials.

When the content of the higher alcohol is 1% by weight or less relative to the total amount of the cosmetic, sufficient emulsification is not obtained, whereas when the amount is 20% by weight or more, stable emulsification is possible, but the higher alcohol in accordance with the present invention has a melting point of 45° C. or more so that when the composition ration is increased, the amount of the components that are solid at normal temperature increases to make touch of the cosmetic after application hard, thereby degrading feeling upon using.

The above-described solution is emulsified and agitated at 70° C. or more, and the solution containing the above-described components is cooled to 40° C. or less while being emulsified and agitated.

By emulsifying the solution in which the polysaccharide, two or more kinds of higher alcohols and the oily component are dispersed at 70° C. or more, the components to be emulsified can be emulsified stably.

By cooling a mixture of the above-described polysaccharide, two or more kinds of the higher alcohols and the oily component, which is dispersed in water and the hydrophilic solvent by emulsifying and agitating at 70° C. or more, to 40° C. or less, while continuously emulsifying and agitating in this state, this state can be fixed. Therefore, the cosmetic in accordance with the present invention has the state in which the oily component and water are dispersed specifically so that a cosmetic in an emulsified state, which well blends into skin, can be obtained. Where the mixture is cooled to 40° C. or less while being emulsified and agitated, the same agitating device can be used.

The present invention according to claim 17 is a method for producing a cosmetic in an emulsified state, which contains a titanium dioxide microparticle, wherein the titanium dioxide microparticle coated with hydrous silicic acid and/or a hydrous silicate compound is prepared by directly subjecting a titanium dioxide microparticle to a surface treatment with hydrous silicic acid and/or a hydrous silicate compound, or by subjecting a titanium dioxide microparticle to a surface treatment with methyl-hydrogen-polysiloxane, and then, subjecting it to a surface treatment with hydrous silicic acid and a hydrous silicate compound.

In accordance with the present invention of claim 17, by using the method of making titanium dioxide powder react with a solution of sodium silicate directly in the surface treatment step, or performing the surface treatment with hydrous silicic acid and a hydrous silicate compound, after performing the surface treatment with methyl-hydrogen-polysiloxane, the titanium dioxide microparticle subjected to the surface treatment capable of preventing polyvalent metal from remaining can be used, whereby intermixing of components adapted to add a plus electrical charge is restrained so that the cosmetic in accordance with the present invention becomes more stable.

The present invention according to claim 18 is a method for producing a cosmetic in an emulsified state, wherein the titanium dioxide microparticle coated with hydrous silicic acid and/or a hydrous silicate compound contains a titanium dioxide microparticle containing substantially no aluminum nor aluminum compounds.

In accordance with the present invention of claim 18, the titanium dioxide microparticle coated with hydrous silicic acid and/or a hydrous silicate compound is a titanium dioxide microparticle containing substantially no aluminum nor aluminum compounds. Consequently, since the titanium dioxide microparticle coated with hydrous silicic acid and/or a hydrous silicate compound contains the titanium dioxide microparticle containing substantially no aluminum nor aluminum compounds, nanoparticles of randomly granulated polysaccharide do not generate any aggregating force, whereby the emulsified state of the cosmetic can be made more stable.

The present invention according to claim 19 is a method for producing a cosmetic in an emulsified state, wherein the titanium dioxide microparticle coated with hydrous silicic acid and/or a hydrous silicate compound is contained in an amount of 1% by weight to 20% by weight relative to the total amount of the cosmetic, the higher alcohol is contained in an amount of 1% by weight to 15% by weight relative to the total amount of the cosmetic, and the oily component other than the higher alcohol is contained in an amount of 0.5% by weight to 30% by weight relative to the total amount of the cosmetic.

In accordance with the present invention of claim 19, the titanium dioxide microparticle coated with hydrous silicic acid and/or a hydrous silicate compound is contained in an amount of 1% by weight to 20% by weight relative to the total amount of the cosmetic so that the cosmetic exhibits sufficient ultraviolet rays preventive effect. In the case of 1% by weight or less, the ultraviolet rays preventive effect is not sufficient, whereas if 20% by weight or more is contained, effect corresponding to the increment thereof cannot be expected, so as to be less preferable in cost.

The titanium dioxide microparticle coated with hydrous silicic acid and/or a hydrous silicate compound is added in an amount of 1% by weight to 20% by weight relative to the total amount of the cosmetic, and agitated. At this time, by dissolving the titanium dioxide of the present invention into a slurry with glycerin and butylene glycol, the addition thereof can be performed smoothly. In accordance with the present invention, when the above-described specific polysaccharide and the higher alcohol to be added in the solution later are dissolved, a para active agent having a hydrophilic part and a hydrophobic part is formed, and this para active agent enables the oily component to be stably emulsified. When this polysaccharide is 0.01% by weight or less, sufficient stability is not obtained, and in the case of 1% by weight or more, improvement of the stability performance corresponding to the addition amount is not observed so as to be less preferable in cost.

The higher alcohol is contained in an amount of 1% by weight to 15% by weight relative to the total amount of the cosmetic, and the oily component other than the higher alcohol is contained in an amount of 0.5% by weight to 30% by weight relative to the total amount of the cosmetic. Therefore, the oily component is sufficiently emulsified. Where the higher alcohol is contained in an amount of 1% by weight or less relative to the total amount of the cosmetic, sufficient emulsification is not effected, whereas when 15 weight % by weight or more, stable emulsification is possible, but as the composition ratio increases, the amount of the components at normal temperature or more increases, thereby hardening touch of the cosmetic after application hard, and consequently, feeling upon using is degraded.

The present invention according to claim 20 is a method for producing a cosmetic in an emulsified state, wherein the higher alcohol has a melting point of 45° C. or more, and at least two kinds of higher alcohols are used.

In accordance with the present invention of claim 20, the higher alcohol has a melting point of 45° C. or more, and at least two kinds of the higher alcohols are used so that the size of particles of the higher alcohols and polysaccharide becomes inhomogeneous, whereby emulsified particles containing the oily component become difficult to be crystallized, and consequently, the emulsification becomes more stable. When only one kind of higher alcohol is contained, sufficient emulsification stability is not obtained.

The present invention according to claim 21 is a method for producing a cosmetic in an emulsified state, wherein the mixing ratio of the two or more kinds of the higher alcohols is such that the mixing ratio of a higher alcohol of which the content is a maximum and a higher alcohol of which the content is a minimum ranges from 1:1 to 5:1.

In accordance with the present invention of claim 21, the mixing ratio of the two or more kinds of the higher alcohols is such that the mixing ratio of a higher alcohol of which the content is a maximum and a higher alcohol of which the content is a minimum ranges from 1:1 to 5:1 so that one alcohols out of the two or more kinds of mixed higher alcohols is mixed in the ratio of at least one fifth relative to the other one higher alcohol, and consequently, aggregates of the higher alcohols having different molecular weights and the polysaccharide form a substantially corresponding amount of aggregates, each having different sizes, thereby preventing the formation of a homogeneous particulate structure, and consequently, enabling the stabilization of the emulsified state.

The present invention according to claim 22 is a method for producing a cosmetic in an emulsified state, wherein the higher alcohol is composed of two or more kinds of higher alcohols selected from hexadecanol, octadecanol, eicosanol, and docosanol, each of the selected two or more kinds of higher alcohols is contained in an amount of 0.4% by weight or more relative to the total amount of the cosmetic, and the total of the selected two or more kinds of higher alcohols is contained in an amount of 0.8% by weight to 20% by weight relative to the total amount of the cosmetic.

In accordance with the present invention of claim 22, the above-described specific two or more kinds of higher alcohols are used, and consequently, a plurality of chemical compounds, each having hydroxyl groups, are contained, so that the aggregates formed with the polysaccharide and higher alcohols have various sizes, thereby preventing the aggregates of the higher alcohols having different molecular weights and the polysaccharide from forming a homogeneous particulate structure, and consequently, enabling the stabilization of the emulsified state.

If each higher alcohol is not used in an amount of 0.4% by weight or more, the effect due to the use of two or more kinds of higher alcohols cannot be sufficiently achieved. And, when the amount of a mixture of two or more kinds of higher alcohols is 0.8% by weight or less relative to the total amount of the cosmetic, a sufficient particulate structure cannot be formed with the polysaccharide, whereas when 20% by weight or more is intermixed, the effect corresponding to the intermixing content is not observed, which is less preferable in cost.

The present invention according to claim 23 is a method for producing a cosmetic in an emulsified state, wherein the cosmetic contains one or more kinds of the materials selected from the group of tripotassium phosphate, trisodium phosphate, potassium metaphosphate, sodium metaphosphate, sodium pyrophosphate, sodium tripolyphosphate, sodium tetrapolyphosphate, sodium pentapolyphosphapte, potassium pyrophosphate, potassium tripolyphosphate, potassium tetrapolyphosphate, potassium pentapolyphosphate, citric acid, sodium citrate, potassium citrate, hydroxyethane diphosphonic acid, and diethylenetriamine pentaacetic acid in an amount of 0.05% by weight to 5% by weight relative to the total amount of the cosmetic.

In accordance with the present invention of claim 23, the cosmetic contains one or more kinds of the materials selected from the groups of the above-described phosphate compounds in an amount of 0.05% by weight to 5% by weight relative to the total amount of the cosmetic so that, if the component adapted to add a plus electrical charge is blended in the cosmetic, phosphates (ion), citrates (ion), phosphinous acid compounds (ion), and acetic acid compounds (ion) speedily react to neutralize it, and make the apparent charge to a minus charge, whereby the stability of the emulsified state can be improved.

The present invention according to claim 24 is a method for producing a cosmetic in an emulsified state, wherein the polysaccharide contains at least a polysaccharide represented by the following general formula (chemical 1).

one out of each of the groups, polar oils gather in a surface of the oily component, whereby a surface of an oil droplet has polarity much more to enhance the stability of the emulsified state. Consequently, even where ceramide powder, zinc oxide powder, mica powder as powders having surface activation, or such components as to damage the emulsification stability, such as ascorbyl acid phosphate magnesium, ascorbic acid glucoside, etc., which are easy to be deposited, are contained, a cosmetic capable of maintaining a stable emulsified state can be produced.

In addition, it is necessary that the amount of the oily component (A) is greater than that of the oily component (B), and it is necessary that the ratio thereof is 2:1 or more. In the case

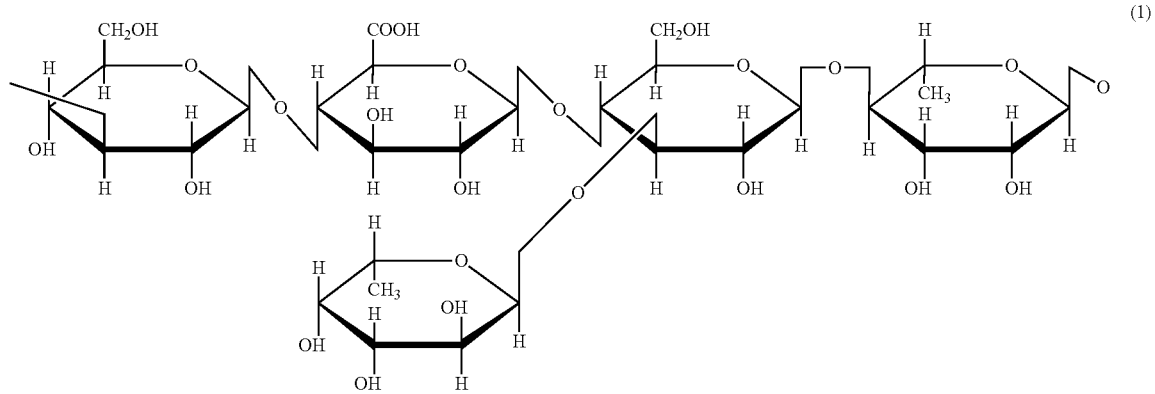

In accordance with the present invention of claim 24, in the method for producing the cosmetic, at least the polysaccharide represented by the above-described general formula (1) is contained in the polysaccharide so that when the component to be emulsified as other oily component are emulsified with the polysaccharide represented by the above-described general formula (1) and two or more kinds of specific higher alcohols, the cosmetic in a stable emulsified state can be obtained. By using the above-described polysaccharide and two or more kinds of specific higher alcohols, the polysaccharide and the higher alcohols are bonded to each other with hydrogen bonds, and aggregates (clusters) are generated to form a particulate structure, whereby the cosmetic in a Table emulsified state can be obtained.

The present invention according to claim 25 is a method for producing a cosmetic in an emulsified state, wherein the oily component contains an oily component (A) composed of at least one selected from the group consisting of silicone oil, fluorinated hydrocarbon and derivatives thereof, hydrocarbon, fatty acid, fatty acid ester of monohydric alcohol, animal and vegetable oils, oxycarboxylic acid ester, fatty acid ester of polyhydric alcohol (melting point: 40° C. or less) and liquid wax, and an oily component (B) composed of at least one selected from the group consisting of solid wax, dihydric higher alcohol, cyclic alcohol and fatty acid ester thereof, fatty acid ester of polyhydric alcohol (melting point: 40° C. or more) and phospholipid such that a weight ratio of the oily component (A) to the oily component (B) ranges from 2:1 to 50:1.

In accordance with the present invention of claim 25, by classifying specific components among the oily component to two groups of the oily component (A) and the oily component (B), in an emulsified state of the higher alcohol, oily component and polysaccharide, and selecting and combining at least of 50:1 or more, sufficient polarity is not obtained in the surface, so that stable emulsification is not obtained.

The present invention according to claim 26 is a method for producing a cosmetic, wherein the oily component (A) is composed of at least one selected from dimethyl polysiloxan, trimethyl polysiloxan, squalane, paraffin, isopropyl palmitate, myristyl myristate, isostearyl myristate, glyceryl triethylhexanoate, caprylic/capric acid triglyceryl glyceryl tricaplyrate.tricaprate, grape seed oil, rosa canina fruit oil, sunflower oil, olive fruit oil, avocado oil, macadamia ternifolia seed oil, meadowfoam seed oil, shea oil and jojoba seed oil, the oily component (B) is composed of at least one selected from beeswax, hydrogenated jojoba oil, chimyl alcohol, batyl alcohol, cholesterol, cholesteryl stearate, phytosterol, glyceryl trimyristate and glyceryl tristearate, and the oily component (A) and the oily component (B) are used in combination.

In accordance with the present invention of claim 26, the method of classifying the oily component to two groups of the oily component (A) and the oily component (B), and selecting at least one out of each of the groups has been found from experience, and consequently, the reasons for this effect have not been sufficiently made clear.

The present invention according to claim 27 is a method for producing a cosmetic in an emulsified state, wherein the cosmetic does not contain any one of a cationic surfactant, anionic surfactant and nonionic surfactant composed of alkylene (carbon atoms: 2 to 4) oxide adduct.

In accordance with the present invention of claim 27, since the cosmetic does not contain any one of a cationic surfactant, anionic surfactant, and nonionic surfactant composed of alkylene (carbon atoms: 2 to 4) oxide adduct. Therefore, emulsified substances that are stable over a long period of time, and blend into skin can be obtained, whereby it is unnecessary to use any surfactant having substantially surface-acting performance, and consequently, a cosmetic which well blends into skin without contaminating the surrounding environment can be obtained. In addition, as the surfactant having substantially surface-acting performance is not used, a cosmetic with high safety, which exhibits water resistance, and is capable of being washed away with general face cleansing and bathing, such as soap cleansing, etc., can be obtained.

The present invention according to claim 28 is a method for producing a cosmetic in an emulsified state, wherein the polysaccharide is granulated to random particle diameters.

In accordance with the present invention of claim 28, since the polysaccharide is granulated to random particle diameters, a cosmetic wherein the emulsified state of the oily component is stable can be produced.

Effect of the Invention

The present invention has a titanium dioxide microparticle of which a surface is coated with hydrous silicic acid and/or a hydrous silicate compound is contained so that no aggregating force is generated in the polysaccharide dispersed in the cosmetic, whereby high emulsification stability of the titanium dioxide microparticle can be obtained in the cosmetic.

The cosmetic of the present invention contains a higher alcohol, an oily component other than the higher alcohol, and a polysaccharide, the polysaccharide contains at least one of fucose, glucose, glucuronic acid and rhamnose as a constituent monosaccharide, and having fucose and/or rhamnose in a side chain, is contained in an amount of 0.01 to 1% by weight relative to the total amount of the cosmetic. Consequently, it is unnecessary to add any surfactant (inclusive of substances having substantially surface-acting performance) in the cosmetic, whereby the emulsification stability of components to be emulsified, such as the oily component, etc. can be maintained over a long period of time.

Furthermore, in accordance with the present invention, a specific polysaccharide and two kinds of higher alcohols, each having a melting point of 45° C. or more, are used so that a cosmetic in an emulsified state, which is excellent in thermal stability and storage stability, can be obtained. Therefore, a stable emulsified state can be maintained without using any surfactant, and a cosmetic excellent in touch and feel can be obtained. In addition, a cosmetic well blending into skin can be produced without adding any surfactant, etc.

Furthermore, in accordance with the present invention, by using a specific polysaccharide and two or more kinds of higher alcohols, each having a melting point of 45° C. or more, blending of other oily components becomes possible, and consequently, oily components can be emulsified irrespective of a required HLB value of many kinds of oily components to be emulsified, which are contained in the cosmetic, whereby the emulsification of hydrocarbon-based oily components and silicone-based oily components becomes possible, too. As a result, troubles and labours upon selecting emulsification dispersants suited to many kinds of components to be emulsified can be reduced to minimum.

BEST MODE FOR CARRYING OUT THE INVENTION

Figure 1:
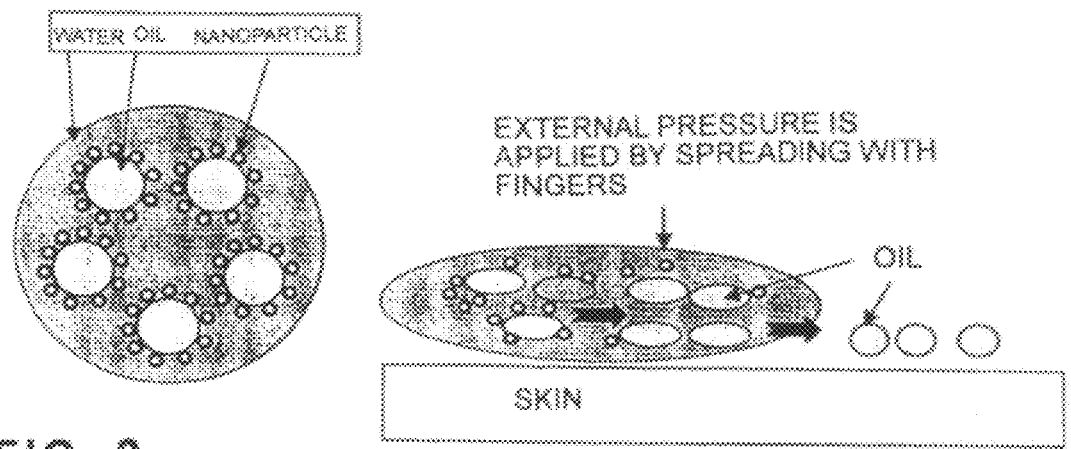
FIG. 1 is a diagram showing a movement of an oily component when the conventional cosmetic is applied to skin.

The cosmetic of the present invention is a cosmetic which contains a titanium dioxide microparticle of which a surface is coated with hydrous silicic acid and/or a hydrous silicate compound, a higher alcohol, an oily component other than the higher alcohol and a specific polysaccharide, and the polysaccharide is contained in an amount of 0.01% by weight to 1% by weight relative to the total amount of the cosmetic.

The above-described titanium dioxide microparticle is added to the cosmetic as an ultraviolet rays reflecting material. And, the cosmetic of the present invention is excellent in feeling upon using and excellent in stability while exhibiting sufficient water resistance though no surfactant is blended in order to enhance the water resistance, is readily washed away with soap, etc., is high in stability as products, and is capable of preventing ultraviolet rays.

In addition, the cosmetic of the present invention contains an oily component as a component to be emulsified in an amount of 1% by weight to 20% by weight relative to the total amount of the cosmetic as the oily component contained in a normal cosmetic, contains a specific polysaccharide in an amount of 0.01% by weight to 1% by weight relative to the total amount of the cosmetic, and contains two or more kinds of higher alcohols selected from hexadecanol, octadecanol, eicosanol, and docosanol in an amount of 1% by weight to 20% by weight relative to the total amount of the cosmetic. The oily component as the components to be emulsified include silicone oil, hydrocarbon, fluorinated hydrocarbon, wax, alcohol having carbon atoms of 14 or less, fatty acid ester, organic acid ester, etc., but organic substances of compounds having a dielectric constant ranging from 1 to 5 (F/m), and an inorganicity/organicity ratio ranging from 0 to 0.5 A are particularly desirable.

The sun care product compositions of the present invention include sunscreen creams, suntan milky lotions, makeup bases, foundations, control colors, concealers, and day skin care liquid (creams, milky lotions).

The higher alcohols used in the present invention are higher alcohols, each having a melting point of 45° C. or more, and more specifically include hexadecanol (cetyl alcohol) (melting point 50° C.), octadecanol (stearyl alcohol) (melting point 59° C.), eicosanol, and docosanol (behenyl alcohol)(melting point 72° C.), tetracosanol (melting point 74° C.), etc. as straight-chain saturated aliphatic alcohols, and hydrogenated rapeseed alcohol (melting point 60 to 70° C.), hydrogenated coconut alcohol (melting point 50 to 65° C.), hydrogenated palm alcohol (melting point 50 to 65° C.), etc. as alcohols obtained by adding hydrogen to plant extracted oils and fats. One kind or two or more kinds of these higher alcohols can be used in combination.

It is preferable that the higher alcohols are two or more kinds selected from of hexadecanol, octadecanol, eicosanol, and docosanol, each alcohol is contained in an amount of 0.4% by weight or more relative to the total amount of the cosmetic, and the total amount of these alcohols ranges from 0.8% by weight to 20% by weight, more preferably from 1% by weight to 15% by weight, relative to the total amount of the cosmetic.

The oily component as the component to be emulsified in accordance with the present invention includes silicone oil, fluorinated hydrocarbon and derivatives thereof, hydrocarbon, alcohol of which the melting point is 45° C. or less, polyhydric alcohol, fatty acid, fatty acid ester of monohydric alcohol, animal and vegetable oils, organic acid ester, wax, cyclic alcohol, fatty acid ester thereof, fatty acid ester of polyhydric alcohol, phospholipid, etc. It is preferable that specific components out of these oily components are classified to two groups of the oily component (A) and the oily component (B), at least one kind of oily component is selected from each group and used in combination as the oily component.

The oily component (A) used in the present invention is liquid at normal temperature, and the oily component (B) is solid or paste at normal temperature. Since the cosmetic of the present invention contains higher alcohols, each having a melting point higher than body temperature, the feel upon application becomes heavy to increase blocking feeling after application. Under the above circumstances, in order to obtain penetrating properties and smooth application feeling, the oily component (A) that is liquid at normal temperature is required to be blended.

The combination of only the higher alcohols, each having a melting point of 45° C. or more, and the oily component (A) degrades the blending into each other, and, upon applying, the oily component (A) spreads on skin and penetrates therethrough, but the higher alcohols inferior in smoothness cause heavily dragging feeling and does not improve blocked feeling.

By blending the hydrous oily component (B) that is solid or paste at normal temperature, the oily component (A) and the higher alcohols are bonded, whereby the compatibility with each other can be increased. Consequently, the smoothness becomes good entirely upon application, thereby effecting smooth feeling. And, by virtue of the hydrous properties of the oily component (B), the blocked feeling is eased, and feeling after application is improved, whereby feeling upon using is improved. The oily component (B) is a component serving as bonds, and can achieve such effect with an amount smaller than that of the oily component (A). The composition ratio of the oily component (A) and the oily component (B) ranges from 2:1 to 50:1 by weight ratio. It is preferable to use them in the range from 3:1 to 30:1, and more preferably, from 5:1 to 10:1.

Examples of the oily component (A) include silicone oil, fluorinated hydrocarbon and derivatives thereof, hydrocarbon, fatty acid ester of monohydric alcohol, animal and vegetable oils, oxycarboxylic acid ester, fatty acid ester of polyhydric alcohol (melting point: 40° C. or less) and liquid wax, and examples of the oily component (B) include solid wax, dihydric higher alcohol, cyclic alcohol and fatty acid ester thereof, fatty acid ester of polyhydric alcohol (melting point: 40° C. or less) and phospholipid.

Examples of the fatty acid include lauric acid, myristic acid, palmitic acid, stearic acid, behenic acid, oleic acid, linoleic acid, linolenic acid, undecylenic acid, arachidonic acid, docosahexaenoic acid (DHA), 12-hydroxystearic acid, isostearic acid, etc.

Examples of the alcohol having a melting point of 45° C. include rauryl alcohol, myristyl alcohol, oleyl alcohol, 2-hexyl decanol, isostearyl alcohol, 2-decyl tetradecynol, etc.

Examples of the silicone oil as the oily component (A) include dimethyl polysiloxane, trimethyl polysiloxane, ethyl methyl polysiloxane, diethyl polysiloxane, methyl-hydrogen-polysiloxane, methyl phenyl polysiloxane, polyether modified organo polysiloxane such as dimethyl siloxane-methyl(polyoxyethylene) siloxane copolymer and dimethyl siloxane-methyl(polyoxyethylene-polyoxypropylene) siloxane copolymer, cyclic dimethyl polysiloxane such as dimethylsiloxane-alkoxy (having 4 to 12 carbon atoms)methylsiloxane copolymer, octamethyl cyclotetrasiloxane, octamethyl cyclopentasiloxane, decamethyl cyclohexasiloxane, and dodecamethyl cyclohexasiloxane, fluorine modified organo polysiloxane such as fluoromethylsiloxane.dimethylsiloxane copolymer, fluoroalkyl.polyoxyalkylene modified organo copolymer, fluoroalkyl.polyoxyalkylene modified organo polysiloxane such as fluoromethyl siloxane.polyoxyethylene methylsiloxane copolymer and fluoromethylsiloxane.polyoxyethylene polyoxypropylene methylsiloxane copolymer, terminal or side chain modified organo polysiloxane such as dimethyl polysiloxane modified substance in which a hydroxyl group is introduced in a terminal thereof, and hydroxymethylsiloxane.dimethylpolysiloxane copolymer in which a hydroxyl group is introduced in a side chain partially, and modified amino organo polysiloxane such as dimethyl amino butyl methylsiloxane.dimethylsiloxane polymer having a dialkyl aminoalkyl group in a side chain thereof, etc. In particularly, dimethyl polysiloxane and trimethyl polysiloxane are suited.

Examples of the fluorinated hydrocarbon as the oily component (A) include polyperfluoroethoxymethoxy difluorohydroxyetyl, polyperfluoroethoxymethoxy difluorohydroxyetyl PEG phosphic acid, polyperfluoroethoxymethoxy difluorohydroxymethyl distearamide, perfluoropolyether, ethoxymethoxy difluorohydroxyetyl, perfluorodecalin, perfluorooctane.

Examples of the hydrocarbon as the oily component (A) include squalane, squalene, ceresin, paraffin (n-hydrocarbon having carbon atoms 16 to 40, or a mixture thereof), micro crystallin wax (a mixture of isoparaffin having a molecular weight of 450 to 1000, a small amount of n-paraffin, and naphtenic hydrocarbon), liquid paraffin, liquid isoparaffin, pristane, polyisobutylene, vaseline, etc. The preferable materials are squalane and paraffin.

Examples of the fatty acid ester of monohydric alcohol as the oily component (A) include ethyl acetate, butyl acetate, amyl acetate, ethylhexyl-2-succinate, 2-hexyl decyl adipate, di-2-heptyl undecyl adipate, cetyl 2-ethylhexanoate, diisopropyl sebacate, di-2-ethylhexyl sebacate, N-alkyl glycol monoisostearate, iso cetyl isostearate, trimethylolpropane triisostearate, ethylene glycol di-2-ethylhexanoate, trimethylolpropane tri-2-ethylhexanoate, pentaerythritol tetra-2-ethylhexanoate, cetyl ethylhexanoate, octyl dodecyl gum ester, oleyl oleate, octyl dodecyl oleate, decyl oleate, neopentylglycol dicaprate, triethyl citrate, ethylhexyl succinate, amyl acetate, ethyl acetate, butyl acetate, iso cetyl stearate, butyl stearate, diisopropyl sebacate, di-2-ethylhexyl sebacate, hexyldecyl dimethyloctanate, ethyl laurate, hexyl laurate, isopropyl myristate, cetyl octate, octyl dodecyl myristate, isostearyl myristate, myristate-2-hexyl decyl, myristyl myristate, isopropyl palmitate, 2-ethylhexyl palmitate, 2-hexyl decyl palmitate, 2-heptyl undecyl palmititate, butyl stearate, isocetyl stearate, decyl oleate, stealyl oleate, oleyl oleate, etc. The preferable materials among them are isopropyl palmititate, myristyl myristate and isostearyl myristate.

Animal and vegetable fats and oils as the oily component (A) include fats and oils derived from vegetables and animals. The fats and oils derived from, vegetables include drying oils, semi-drying oils, non-drying oils and vegetable fats that are solid at normal temperature, examples of the drying oils include sunflower oil, soybean oil, evening primrose oil, grape seed oil, Rose Hip Oil, Kukui Nut Oil, and examples of the semi-drying oils include almond oil, Sesame Oil, Wheat germ oil, corn oil and cottonseed oil, examples of the non-drying oils avocado oil, olive oil, cameria oil, Apricot Kernel Oil, CASTOR SEED OIL, PEANUT OIL, HAZEL SEED OIL, MACADAMIA TERNIFOLIA SEED OIL, and MEADOWFOAM SEED OIL, examples of the vegetable fats include COCOA SEED BUTTER, SHEA BUTTER, RHUS SUCCEDANEA FRUIT WAX, COCONUT OIL, PALM OIL, PALM KERNEL OIL, etc. grape seed oil rose hip oil, olive oil, avocado oil, madadamia ternifolia seed oil, meadowform seed oil, and shea butter among them are suited.

The fats and oils derived from animals include beef tallow, cattle leg grease, cattle bone fat, hardened beef tallow, hydrogenated oil, turtle oil, lard, horse grease, mink oil, liver oil, egg yolk oil, etc., Examples of oxycarboxylic acid ester include isostearyl malate, diisostearyl malate, triethyl citrate, cethyl lactate, myristyl Lactate, dimethyl succinate, etc.

Examples of fatty acid ester of polyhydric alcohol (melting point: 40° C. or less) as the oily component (A) include glyceryl tri-2-ethylhexanoate, glyceryl tricaplyrate.tricaprate, glyceryl tricaplyrate, glyceryl trilaurate, cholesteryl isostearate, glyceryl triisopalmitate, soft cholesteryl lanolate, propylene glycohol dicaplyrate, propylene glycohol dicaprate, propylene glycohol di nonanoate, propylene glycohol dicaplyrate.dicaprate, propylene glycohol distearate, propylene glycohol isostearate, propylene glycohol dioleate, etc. In particular, glyceryl tri-2-ethylhexanoate and glyceryl tricaplyrate.tricaprate are suited.

Examples of liquid wax as the oily component (A) include liquid lanolin and jojoba seed oil, and jojoba seed oil is preferable.

Examples of the solid wax as the oily component (B) include animal waxes and vegetable waxes, examples of the animal waxes include bees wax, whale wax, lanolin, hard lanolin, hardened lanolin, reduced lanolin, lanolin hydrous, etc., and examples of the vegetable waxed include carnauba wax, candelilla wax, hydrogenated jojoba oil, etc. Bees wax is preferable among them.

Examples of higher alcohol as the oily component (B) include chimyl alcohol (monopalmityl glycerinether), batyl alcohol (monostearyl glycerinether).

Examples of cyclic alcohols as the oily component (B) include cholesterol (cholesterine), dihydro cholesterol, phytosterol (sitosterol), campesterol, stigmasterol, etc., and cholesterol (cholesterine) and phytosterol (sitosterol) are preferable among them.

Examples of fatty acid ester of cyclic alcohols as the oily component (B) include cholesteryl stearic acid, cholestyeryl 12-hydroxystearic acid, cholestyeryl isostearic acid, cholesteryl.behenyl.octyldodecyl ester, cholesteryl.octyidodecyl dodecyl ester, oleic acid.phytosterol ester, 2-octyl, dodecyl phytosterol ester, 2-octyl, dodecyl behenyl.phytosterol ester, etc. Cholesteryl stearic acid is preferable among them.

Examples of fatty acid ester (melting point: 40° C. or more) of polyhydrous alcohol as the oily component (B) include glyceryl tripalmitate, glyceryl tristearate, glyceryl trioxystearate, glyceryl triundecylate, glyceryl trilanoline fatty acid, glyceryl trimyristate, grycel oligo ester (adipic acid.2-ethylhexanoate-stearate), gryceryl tri(caplyrate.caprate.myristate, stearate), dipentaerythritol fatty acid ester of erythritol fatty acid ester, dipentaerythritol hexaoxystearate, etc. In particular, grycel oligo ester (adipic acid.2-ethylhexanoate.stearate), gryceryl tri(caplyrate.caprate.myristate, stearate), dipentaerythritol (a mixture acid of hydroxystearic acid, stearic acid rosinic acid), 12-dipentaerythrityl hydroxysterate are suited.

Examples of phospholipid as the oily component (B) include soybean phospholipid and egg yolk lecithin, etc.

The higher alcohol of the present invention forms aggregates (clusters) with the polysaccharide of the present invention, and is adsorbed on the oily component so as to be separated from water and dispersed therein. Therefore, in the case of one kind of higher alcohol, the size of the aggregate (cluster) with the polysaccharide of the present invention becomes homogeneous so as to be arranged regularly, thereby becoming a liquid crystal state. Such liquid crystal state proceeds with age, and liquid crystals gradually separate from water and oil, whereby the emulsified state becomes unstable, which is less preferable. Therefore, by making the size of the aggregates (clusters) of the higher alcohol and the polysaccharide irregular, they can be prevented from being crystallized so as to be stabilized, and consequently, in order to make them more irregular, at least tow kinds, more preferably at least three kinds, of higher alcohols of the present invention are used in combination, whereby the stability is improved.

And the higher alcohol of the present invention forms aggregates (clusters) with the polysaccharide, and is adsorbed on the oily component so as to be separated from water and dispersed therein. Therefore, the proper content of the higher alcohol depends on the kind and the amount of the oily component to be blended, but the higher alcohol is required to be added in an amount of 1% by weight or more relative to the entire amount of the cosmetic, whereas, in the case of 1% by weight of less, a stable emulsified state is not obtained. In addition, when the content is 20% by weight or more, the effect thereof is obtained, but skin after application becomes such a state as being waxed, thereby deteriorating skin feel so as to be not practical as cosmetics.

And when one of at least two kinds of higher alcohols is excessively blended, the emulsification of the present invention becomes the state similar to the case where only one kind of higher alcohol is blended, and consequently, the higher alcohol becomes regularly crystallized state between other oil and water, and gradually crystallized with age to separate from water. Therefore, each higher alcohol is required to be added in an amount of 0.4% by weight or more. It is preferable that at least two kinds of higher alcohols are mixed such that the mixing ratio of the higher alcohol with a maximum content and the higher alcohol with a minimum content ranges from 1:1 to 5:1. Namely, it is preferable that the added higher alcohols are blended to other higher alcohols in a mixing ratio of five times or less, respectively.

With respect to the kind of the polysaccharide of the present invention, the polysaccharide may be used solely, or two or more kinds of other polysaccharides may be used in combination therewith. But, by using the polysaccharide represented by the later-describing general formula (1) solely, or using a combination of the polysaccharide represented by the later-describing general formula (1) and other polysaccharides, the effect of the present invention can be obtained most efficiently. And, such polysaccharide or polysaccharides is added in an amount of 0.01% by weight to 1% by weight, desirably, 0.02% by weight to 0.2% by weight, more desirably, 0.05% by weight to 0.08% by weight relative to the total amount of the final cosmetic. In the case of 0.01% by weight or less, sufficient effect is not obtained. And in the case of 1% by weight or more, the effect is obtained, but the cost increases so as not to be efficient.

The higher alcohol to be used in the present invention is composed of two or more kinds of higher alcohols selected from hexadecanol, octadecanol, eicosanol and docosanol. The higher alcohols are used such that each of the selected two or more kinds of higher alcohols is contained in an amount of 0.4% by weight or more relative to the total amount of the cosmetic, and that the total of the selected two or more kinds of higher alcohols is contained in an amount of 0.8% by weight to 20% by weight relative to the total amount of the cosmetic. It is assumed that after the aggregates (clusters) are formed with such higher alcohols and the polysaccharide of the present invention, the aggregates are adsorbed on other oily components, thereby separating from water in a dispersed state, and consequently, the inside of the system becomes a temperature of the melting point of the higher alcohols of the present invention or less, whereby the dispersed state of oil is fixed, and a good emulsified state is obtained.

Actually, it has been recognized that the emulsified state with the emulsifying method of the present invention is a special emulsified state different from the emulsified state with another emulsifying method using the oily components, particularly, the three-phase emulsifying method using no surfactant. Namely, where squalane that is liquid at normal temperature, the polysaccharide of the present invention and two or more kinds of higher alcohols are blended and emulsified, for example, the emulsified state is stable at 40° C. over a long period such as several months.
However, where tetradecanol with a low melting point (low in molecular weight), which is not the higher alcohol to be used in the present invention, is used alone or in combination with dodecanol for emulsification with the polysaccharide of the present invention and squalane, the emulsified state separates at 50° C. in several minutes. In addition, upon applying the emulsification with the higher alcohols having carbon (C) atoms of 24 or more, which are other than the higher alcohols to be used in the present invention, on skin, it twists to generate leaf-shaped substances so as to be incomplete as the cosmetic.

Since a large amount of various kinds of components are blended in the cosmetic, the stability thereof may be insufficient by blending only two or more kinds of the higher alcohols of the present invention according to the kind and the amount of the blended components. In particular, where ceramide powder, zinc oxide powder, titanium dioxide powder, and mica powder as powder exhibiting surface activity, or ascorbic acid phosphate magnesium, ascorbic acid glucoside, etc. that readily deposit, are blended, the effects thereof are great. In such a case, two or more kinds of higher alcohols of the present invention are blended, and in order to obtain a stable emulsified state, two or more kinds of oily components having different polarities are blended. Specifically, specific components out of the oily components are classified to two groups of the oily component (A) and the oily component (B), and one or more kind of the oily component out of each group are selected and used in combination. The oily component (A) is composed of one or more kind of oily component selected from the group consisting of silicone oil, fluorinated Hydrocarbon and derivatives thereof, hydrocarbon, alcohol having a melting point of 45° C. or less, fatty acid, fatty acid ester of monohydric alcohol, animal and vegetable oils and fats, oxycarboxylic acid ester, fatty acid ester of polyhydric alcohol (melting point: 40° C. or less) and liquid wax. The oily component (B) is composed of one or more kind of oily component selected from the group consisting of solid wax, cyclic alcohol and fatty acid ester thereof, fatty acid ester of polyhydric alcohol (melting point: 40° C. or less) and phospholipid. By combining the oily component (A) and the oily component (B), and blending them in a composition ratio ranging from 1:1 to 50:1 in a weight ratio, the stability of the emulsified state is further enhanced.

The method of classifying specific components out of the oily components of the present invention to two groups of the oily component (A) and the oily component (B), and selecting and combining at least one out of each of the groups of oily components has been found from experience, and consequently, the reasons for achievement of the effect have not been sufficiently made clear, but it can be assumed as follows. Where the oily components having polarities closer to each other are combined, the oily components are mixed in oil droplets homogeneously, and consequently, the entire polarity of the oil droplets decreases. In addition, by blending the oily components, each having a lower melting point and exhibiting a relatively higher polarity, surfaces of the oil droplets are prevented from being solidified, and the polarity thereof is maintained, thereby enhancing the compatibility with water, preventing the aggregation and crystallization of the components to be emulsified, and attributing to the stabilization thereof, and the chemical compound having a high melting point acts to decrease the size of the oil droplets, and when the size of the oil droplets is made more irregular, the aggregation and crystallization of the components to be emulsified are prevented and the stability thereof is enhanced.

When the oily components having different polarities are combined with each other, the stability of the emulsified state is increased, and when such substances as to make the emulsification and dispersion of the cosmetic unstable when blended in the cosmetic (ceramide powder, zinc oxide powder titanium dioxide powder, and mica powder as powder exhibiting surface activity, or ascorbic acid phosphate magnesium, ascorbic acid glucoside, etc. as powder that readily deposit) are used when blended in the cosmetic, the emulsion-dispersion of the cosmetic can be maintained stably so as to be effective, but where these substances are not blended, the combination of the oily components having different polarities is not limited thereby.

In addition, it is unnecessary to blend organic substances having surface active effect, lecithin, and hydrogenates thereof, phosphoid, chemical compounds thereof, glicolipid and chemical compounds thereof, ceramide and chemical compounds thereof, but there does not occur any problem even when they are blended as the moisturizer and the emollient agent.

The polysaccharide to be used in the present invention is the polysaccharide containing nanoparticles of at least one of fucose, glucose, glucuronic acid and rhamnose as a constituent monosaccharide, and having fucose and/or rhamnose in a side chain. This polysaccharide can have a nanoparticle-shaped configuration in a hydrophilic solvent. In addition, titanium dioxide microparticles are blended as the component for reflecting ultraviolet rays.

In addition, various kinds of components are blended in a large amount in the cosmetic so that the stability thereof may become insufficient according to the kind and the amount of the components to be blended. In particular, where ceramide powder, zinc oxide powder titanium dioxide powder, and mica powder as powder exhibiting surface activity, or ascorbic acid phosphate magnesium, ascorbic acid glucoside, etc. as powder that readily deposit are blended, the effects thereof are great. In such cases, by blending titanium dioxide microparticles, the higher alcohols, and the polysaccharide of the present invention, and blending one or more kinds of phosphates selected from the groups of tripotassium phosphate, trisodium phosphate, potassium metaphosphate, sodium metaphosphate, sodium pyrophosphate, sodium tripolyphosphate, sodium tetrapolyphosphate, sodium pentapolyphosphapte, potassium pyrophosphate, potassium tripolyphosphate, potassium tetrapolyphosphate, potassium pentapolyphosphate, citric acid, sodium citrate, potassium citrate, hydroxyethane diphosphonic acid, and diethylenetriamine pentaacetic acid in an amount of 0.05% by weight to 5% by weight relative to the total amount of the cosmetic, the stability of the cosmetic is improved.

The operation mechanism of the phosphates of the present invention has not been clarified, but it can be assumed, as follows. When the component adapted to add a plus electrical charge exists in the cosmetic, the aggregating action operates against the polysaccharide to be used in the present invention to tighten the emulsified substance to generate solidification and separation of water. At this time, when phosphates exists, they react with the components to be charged to plus in the cosmetic prior to the polysaccharide to be used in the present invention to cancel the plus charge and charge to minus over the entire part of the cosmetic. Consequently, the dispersed state of the polysaccharide to be used in the present invention is maintained, and the cosmetic becomes more stable.

It is necessary to carry out the surface treatment with hydrous silicic acid and/or a hydrous silicate compound, which are least reactive on the polysaccharide containing glucuronic acid having carboxyl groups as a constituent component thereof. Titanium dioxide subjected to the surface treatment is not charged to plus in the cosmetic so that no aggregation force is generated in the polysaccharide dispersed in the cosmetic, whereby high stability is obtained. In addition, the cosmetic of the present invention does not contain any surfactant in order to raise the water resistance. Therefore, it is necessary to obtain an emulsification that is stable and blends in skin without adding any surfactant.

In accordance with the present invention, the three-phase emulsifying method of performing emulsification by adhering nanoparticles which are obtained by randomly granulating the polysaccharide composed of at least fucose, glucose, glucuronic acid and rhamnose as a constituent monosaccharide, and having fucose and/or rhamnose in a side chain thereof, to a surface of the oily component with van der Waals' force, is used. This emulsification is excellent as the emulsifying method, because no surfactant (inclusive of substances having substantially surface-acting performance) is added, and the emulsification stability of the components to be emulsified, such as the oily components, is kept over a long period. And, furthermore, by blending two or more kinds of higher alcohols, each having a melting point of 45° C. or more, the blending properties into skin is made good, and the stability is improved further.

The titanium dioxide microparticles coated with hydrous silicic acid and/or a hydrous silicate compound, which are adapted to be used in the present invention, are titanium dioxide of which the surfaces are revised by making the surfaces of the titanium dioxide microparticles react and be treated with hydrous silicic acid and/or a hydrous silicate compound. For example, by neutralizing an aqueous solution of titanium(IV) chloride with an aqueous solution of sodium hydroxide while keeping the aqueous solution of titanium (IV) chloride at room temperature, thereby depositing colloidal non-crystal titanium hydroxide, and aging the same to prepare a rutile type micro titania sol. By adding water glass (Alkali-silicate) that is prepared by reacting the silicon dioxide ($SiO_2$) and sodium hydroxide (NaOH) with each other, to the micro titania sol along with inorganic acids such as sulphuric acid, silicic acid is deposited on surfaces of titanium dioxide microparticles, thereby forming films, and pH is adjusted with sodium hydroxide to from neutrality to weak Alcali, and after aged, pH is adjusted with inorganic acid such as sulphuric acid to neutrality, whereby a water slurry of titanium dioxide microparticles coated with hydrous silicic acid and/or a hydrous silicate compound is obtained.

By properly adjusting the adding rate of water glass (Alcali-silicate), various kinds of slurries of titanium dioxide microparticles coated with hydrous silicic acid and/or a hydrous silicate compound are obtained. By subjecting these microparticles to filtering, washing with water, and drying, powders are obtained, and according to use thereof, the powder is subjected to the treatment such as pulverization, etc., whereby objective titanium dioxide microparticles coated with hydrous silicic acid and/or a hydrous silicate compound are obtained.

The polysaccharide to be used in the present invention (hereinafter will be referred to as "polysaccharide") is the polysaccharide composed of at least fucose, glucose, glucuronic acid and rhamnose as a constituent monosaccharide, and containing fucose and/or rhamnose in side chains. For example, it is the polysaccharide (C) composed of main chains with a repetition construction composed of glucose, glucuronic acid and rhamnose where one fucose diverges from one glucose in the main chain, as shown by the following formula (1).

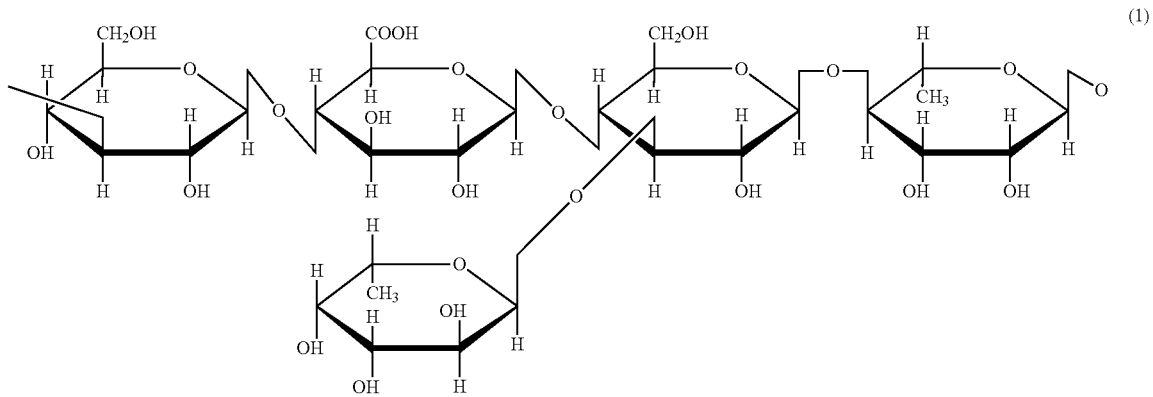

The polysaccharide represented by the formula (1) can be obtained as a product of a microorganism of Alcaligenes latus strain B-16 (FERM BP-2015), for example. The microorganism of Alcaligenes latus strain B-16 is cultured by a normal microbes culturing method, and, after cultured, organic solvents such as acetone, ethanol and isopropyl alcohol are added to a culture liquid. As a result, polysaccharide precipitates as an insoluble substance. The precipitation of polysaccharide is separated, thereby obtaining a polysaccharide.

Generally, microorganisms produce two or more kinds of polysaccharides. Other kinds of polysaccharide than the polysaccharide of the present invention may be included provided that they do not obstruct the effects of the present invention. For example, it has been proved that the polysaccharides produced by a microorganism Alcaligenes latus strain B-16 include at least two kinds of polysaccharides, and the molar ratio of the constituting monosaccharides of polysaccharides which are separated from culture liquid is:

fucose: glucose: glucuronic acid: rhamnose=1:(0.5 to 4): (0.5 to 2):(0.5 to 2). When these two kinds of polysaccharides are separated from each other, one kind of polysaccharide is a polysaccharide having a construction wherein one fucose diverges from one glucose in the main chains with a repeated construction, which is composed of glucose, glucuronic acid and rhamnose, as shown in the formula (1), and another kind of polysaccharide is a polysaccharide of which repetition unit is composed of fucose and mannose.

The former is the polysaccharide of the present invention, has a constituting ratio of fucose, glucose, glucuronic acid and rhamnose which is 1:2:1:1, and is a high molecular component having a molecular weight of about $10^9$ (see the Japan Agricultural Chemistry Society, 1998th year Large Meeting, Summary, P. 371). The latter is the polysaccharide having a repetition construction of fucose and mannose of 1:1, and is a low molecular component having a molecular weight of $10^3$ to $10^7$ (see Y. Nohata, J. Azuma, R. Kurane, Carbohydrate Research 293, (1996) 213 to 222). This low molecular component is not within the scope of the polysaccharide of the present invention, but does not obstruct the stabilizing effect of the present invention so that it may be contained in the cosmetic. This polysaccharide has been sold on market as Alcasealan (trade name, INCI name: Alcaligenes Polysacchaides, manufactured by HAKUTO CO., LTD.).

By using sphingomonas trueperiSPH-011(FERM BP-08582) or SPH-012 (FERM BP-08579) in place of a microorganism Alcaligenes latus strain B-16 (FERM BP-2015), the polysaccharide of the present invention can be obtained. There are welan gum (manufactured by CP Kelco), Daiyutan gum (manufactured by CP Kelco), etc., each having a main chain composed of glucuronic acid, glucose and rhamnose, and a side chain composed of rhamnose, other than the above-described material.

Hereinafter, the method for producing the cosmetic in accordance with the present invention will be explained.

In the producing method of the cosmetic, first, the polysaccharide composed of at least one of fucose, glucose, glucuronic acid and rhamnose as a constituent monosaccharide, and having fucose and/or rhamnose in a side chain thereof is dissolved in water alone, a hydrophilic solvent alone, or a mixture of water and a hydrophilic solvent in an amount of 0.01% by weight to 1% by weight relative to the total amount of the cosmetic. A specific one example of this polysaccharide is explained, as follows.

Upon dissolving the polysaccharide, it is necessary to apply a strong shear, and a homogenizer such as a TK homomixer MARK2 (trade name, manufactured by Tokushukika.co.) or a disperser such as TK homodisperser (trade name, manufactured by Tokushukika.co.) are used to agitate the same. As a result, the above-described polysaccharide can be randomly granulated. In addition, where the size of the above-described polysaccharide scatters, the size of the aggregates (clusters) generated upon adhering to the higher alcohol of the present invention scatters, whereby they are difficult to be crystallized, and the emulsification becomes more stable.

Next, two or more kinds of higher alcohols selected from 0.4% by weight or more of hexadecanol relative to the total amount of the cosmetic, 0.4% by weight or more of octadecanol relative to the total amount of the cosmetic, 0.4% by weight or more of eicosanol relative to the total amount of the cosmetic and 0.4% by weight or more of docosanol relative to the total amount of the cosmetic, are added to the aqueous solution of the polysaccharide of the present invention in an amount of 1% by weight to 20% by weight relative to the total amount of the cosmetic, and at the same time, a mixture containing the oily component in an amount of 1% by weight to 20% by weight relative to the total amount of the cosmetic is added to dissolve them and emulsify them at 70° C. or more, and cooled to 40° C. while emulsifying and agitating. When the component that is difficult to be emulsified, such as titanium dioxide, etc. is contained upon adding this higher alcohol and the oily component, the oily components of the groups having different polarities are used in combination.

In this emulsifying method, a normal emulsifying device called a "homogenizer" can be used. In that case, the higher alcohol and the oily component of the present invention, which are heated to 70° C. or more, as the components to be emulsified, if necessary, components for supplementing emulsification, are added and emulsified while agitating the solution of the specific polysaccharide of the present invention, which is heated to 70° C. or more, with the homogenizer. Depending on the device and the amount of liquid, after agitating for 10 minutes and 60 minutes, the cooling operation starts while agitating. The cooling time depends on the device and the amount of liquid, but the solution is made to normal temperature in 10 minutes to 60 minutes. The cosmetic in an emulsified state in accordance with the present invention can be obtained with this method.

In order to carry out the present invention efficiently, it is important that the polysaccharide to be used in the present invention is the polysaccharide composed of at least one of fucose, glucose, glucuronic acid and rhamnose as a constituting monosaccharide, and containing fucose and/or rhamnose in a side chain. For example, it is the polysaccharide containing at least fucose, glucose, glucuronic acid and rhamnose as a constituent monosaccharide, preferably the polysaccharide (C) having a main chain with a repetition construction, which is composed of glucose, glucuronic acid and rhamnose where one fucose diverges from one glucose in the main chain, as shown by the following formula (1).

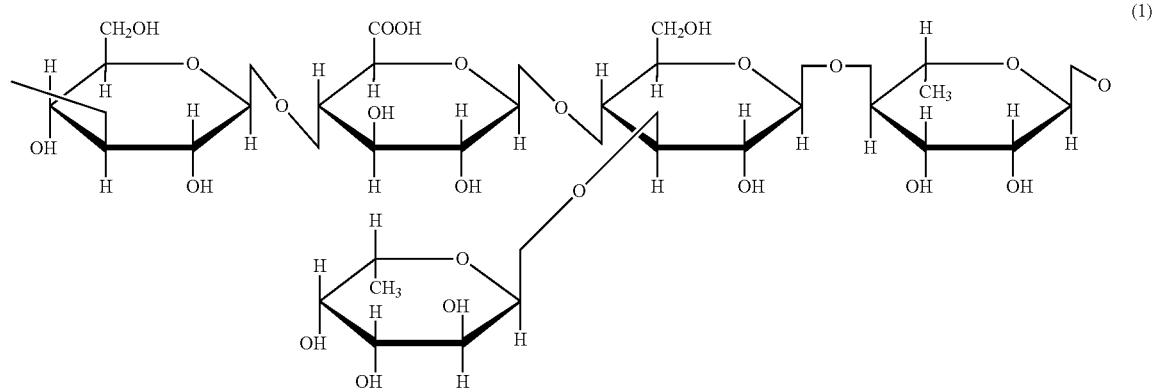

The polysaccharide represented by the formula (1) can be obtained as a product of a microorganism of Alcaligenes latus strain B-16 (FERM BP-2015), for example. The microorganism of Alcaligenes latus strain B-16 is cultured by a normal microbes culturing method, and, by adding organic solvents such as acetone, ethanol and isopropyl alcohol to a culture liquid after culturing, polysaccharide precipitates as an insoluble substance. The precipitation of polysaccharide is separated, thereby obtaining a polysaccharide.

By using the polysaccharide represented by the general formula (1) and the higher alcohol of the present invention, a more stable cosmetic can be obtained. By the adsorption of hydrogen groups of the polysaccharide represented by the general formula (1) and hydroxyl groups of the specific alcohol with hydrogen bonds, aggregates (clusters) of the polysaccharide and the specific higher alcohol are formed. In order to make the emulsification of the present invention more stable, it is desirable that the size and the polarization of the aggregates (clusters) of the polysaccharide and the specific higher alcohol scatter much more.

Figure 2:
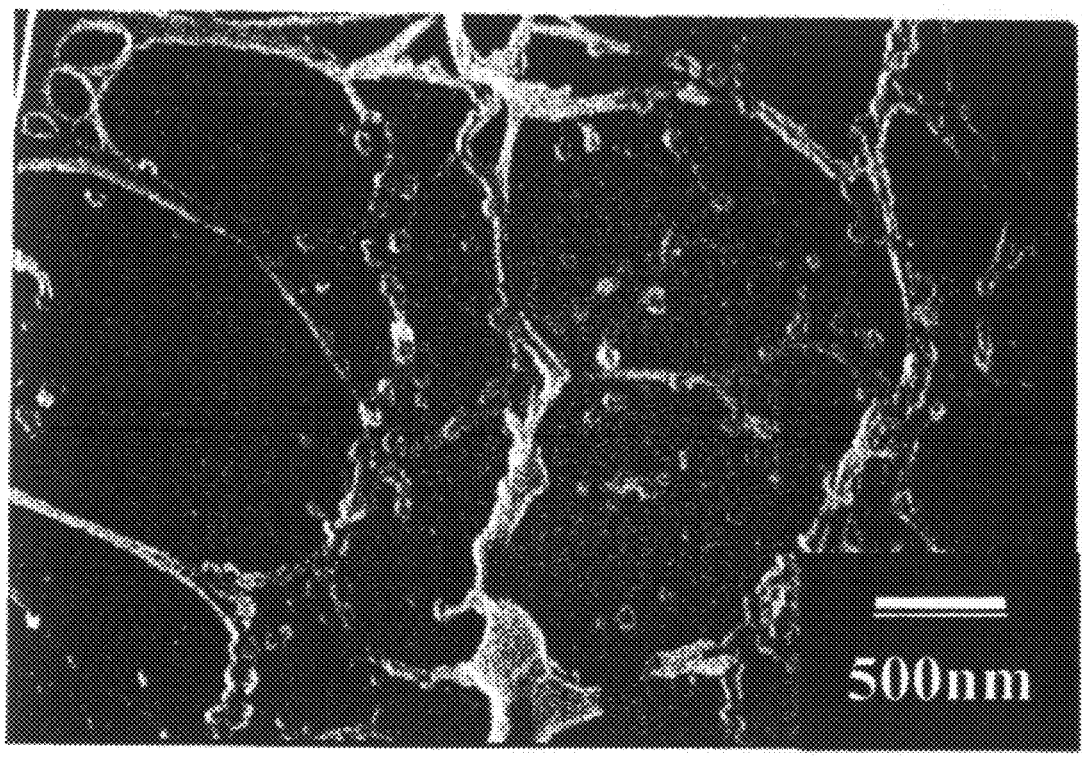
FIG. 2 is a photomicrograph showing a bonding state of a polysaccharide in accordance with the present invention.

The polysaccharide of the present invention forms a network in water, but one unit of the polysaccharide does not stretch in a string-shaped configuration with interwined with other units. As shown in FIG. 2, one unit thereof forms a sphere, and is connected to other units like raying beads with hydrogen bonds so as to become strings, and further intertwined into a network. Therefore, it is necessary to first apply a shearing force with a homogenizer, and cutting the hydrogen bonds physically into string-shaped pieces or spherical units.

When the polysaccharides having scattering sizes are mixed with the above-described higher alcohols at elevated temperatures, the higher alcohols aggregate with hydrogen bonds of the hydroxyl groups, and the hydrogen groups of the polysaccharides and the hydroxyl groups of the higher alcohols aggregate with hydrogen bonds, whereby the emulsified state of the higher alcohols and the polysaccharides is formed. Then, when the temperature of an emulsified solution becomes the melting point of the higher alcohols or less in the following gradually cooling step in such a state, it is solidified to form an aggregate (cluster). And, it contacts another oily component in the solution to form an assembly with another oily component. This assembly is surrounded with water and a hydrophilic solvent by emulsifying and agitating, and is cooled to 40° C. or less while emulsifying and agitating in a dispersed state, whereby the higher alcohols of the present invention become a melting point or less, and are solidified so that the emulsified state is fixed to obtain the cosmetic of the present invention.

The cosmetic of the present invention is in a specifically dispersed state of the oily component and water so that the cosmetic in an emulsified state, which preferably blends into skin, can be obtained.

In addition, in order to further stabilize the emulsification of the present invention, hydrophilic components may be added. Examples thereof include, amino acid, saccharide and derivatives thereof, (POE methyl glucoside), hydrophilic polymer, low molecular weight polyhydric alcohol, etc. By composing a water phase of a mixture system of many components, the water phase can be made inhomogeneous. As a result, the emulsified substance can be prevented from being crystallized with the water phase.

Examples of amino acid include asparagine, aspartic acid, alanine, arginine, isoleucine, orthinine, glutamine, glycine, glutamic acid, derivatives thereof, and salts thereof, cysteine, cystine, citrulline, threonine, cerine, tyrosine, tryptophan, theanine, valine, histidine, hydroxylysine, hydroxyproline, pyrrolidone carbonate, salts thereof.

Examples of saccharide and derivatives thereof include honey, erythritol, maltose, maltitol, xylitol, xylose, pentaerythritol, fructose, dextrine and derivatives thereof, mannitol, sorbitol, inositol, trehalose, glucose, POE methyl glucoside, hydrogenated starch hydrolysates, glucoside trehalose etc.

Examples of hydrophilic polymer include natural high polymers such as xanthan gum, gum arabic, guar gum, karaya gum, carrageenan, pectin, fucoidan, tragant gum, locust bean gum, galactomannan, curdlan, gellant gum, fuco gel, casein, gelatine, starch, collagen, etc., semi-synthetic high polymers such as methyl cellulose, ethyl cellulose, methyl hydroxypropylcellulose, carboxymethylcellulose, hydroxymethylcellulose, hydroxypropylcellulose, sodium carboxymethylcellulose, alginic acid propylene glycol ester, cellulose crystals, sodium acrylate starch, graft copolymer, hydrophobic hydroxypropyl methylcellulose, etc., and synthetic high polymers such as polyvinyl alcohol, polyvinylpyrrolidone, carboxyvinyl polymer, polyacrylic acid salt, polyethyleneoxide, etc. Inorganic minerals such as bentonite, laponite, hectorite, etc. may be used together.

Examples of low molecular weight polyhydrous alcohol include ethanol, 1,3-butylene glycol, ethylene glycol, diethylene glycol, triethylene glycol, polyethylene glycol, propylene glycol, dipropylene glycol, glycerin, butanol, propanol, pentanediol, octandiol, 1-(2-ethylhexyl)glycol ether, etc.

In the cosmetic in an O/W type emulsified state, containing a titanium dioxide microparticle of which a surface is coated with hydrous silicic acid and/or a hydrous silicate compound, the producing method thereof is not limited specifically, but the following method is used, for example.

In the method for producing the cosmetic, first, a component to be emulsified and a polysaccharide composed of at least glucuronic acid as a constituent monosaccharide, and containing fucose and/or rhamnose in a side chain thereof are dissolved in water alone, a hydrophilic solvent alone, or a mixture of water and a hydrophilic solvent at 70° C. or more in an amount of 0.01 to 1% by weight relative to the total amount of the cosmetic. At this time, it is necessary to apply a strong shear, and a homogenizer such as a TK homomixer MARK2 (trade name, manufactured by Tokushukika.co.) or a disperser (trade name, manufactured by Tokushukika.co.) are used.

The dissolving time depends on the device and the amount of liquid, but ranges from about 10 minutes to about 60 minutes. Next, a titanium dioxide microparticle coated with hydrous silicic acid and/or a hydrous silicate compound in an amount of 5% by weight to 30% by weight is previously dissolved in a polyhydrous alcohol such as glycerin, 1,3-butandiol, 1,2 pentadiol, octandiol, 1-(2-ethylhexyl)glycol ether, the temperature is raised to 70° C., and an obtained substance is added to a solution of the polysaccharide, and agitated.

Upon agitating, a normal emulsifying device called a "homogenizer" can be used. The agitating time depends on the device and the amount of liquid and ranges from about 10 to about 20 minutes. Then, an oily ingredient heated to 70° C. or more is added to a mixture liquid heated to 70° C. or more, thereby emulsifying the same. The emulsifying time depends on the device and the amount of liquid, but, after agitating for 10 minutes to 60 minutes, the cooling operation is started while agitating. The cooling time depends on the device and the amount of liquid, but the mixture liquid is cooled to normal temperature in 10 minutes to 60 minutes.

By this method, the cosmetic in an emulsified state where titanium dioxide microparticles coated with hydrous silicic acid and/or a hydrous silicate compound in accordance with the present invention are dispersed homogeneously can be obtained. The titanium dioxide microparticles coated with hydrous silicic acid and/or a hydrous silicate compound are contained in an amount of 1% by weight to 30% by weight, preferably 3% by weight to 20% by weight, and more preferably 5% by weight to 15% by weight relative to the total amount of the cosmetic. In the case of 1% by weight or less, the ultraviolet rays preventive effect is not sufficient, whereas in the case of 30% by weight or more, the ultraviolet rays preventive effect is obtained, but cosmetic floats in white color after application, whereby good appearance as cosmetics is deteriorated, and consequently, the cosmetic is not usable practically. The content of the oily base is determined to be in an amount of 0.5% by weight to 30% by weight, preferably 1% by weight to 20% by weight, and more preferably 5% by weight to 15% by weight relative to the total amount of the cosmetic. In the case of 0.5% by weight or less, sufficient water resistance is not obtained, whereas in the case of 30% by weight or more, the water resistance can be obtained, but the cosmetic becomes sticky after application, and consequently, the cosmetic is not usable practically.

In addition, various kinds of components are blended in a large amount in the cosmetic so that the stability thereof may become insufficient only with the blending of the polysaccharide and two or more kinds of higher alcohols, according to the kind and the amount of the components to be blended. In particular, where ceramide powder, zinc oxide powder, and mica powder as powder exhibiting surface activity, or ascorbic acid phosphate magnesium, ascorbic acid glucoside, etc. as powder that readily precipitate are blended, the effects thereof are great. In such cases, by blending the polysaccharide and the higher alcohols of the present invention, and blending one or more kinds of phosphates selected from the groups of tripotassium phosphate, trisodium phosphate, potassium metaphosphate, sodium metaphosphate, sodium pyrophosphate, sodium tripolyphosphate, sodium tetrapolyphosphate, sodium pentapolyphosphapte, potassium pyrophosphate, potassium tripolyphosphate, potassium tetrapolyphosphate, potassium pentapolyphosphate, citric acid, sodium citrate, potassium citrate, hydroxyethane diphosphonic acid, and diethylenetriamine pentaacetic acid in an amount of 0.1% by weight to 5% by weight relative to the total amount of the cosmetic, the stability of the cosmetic is improved.

In order to blend them, they are added upon dissolving the polysaccharide of the present invention, and are dissolved simultaneously with the polysaccharide of the present invention. As a result, phosphates (ion), citrates (ion), phosphinous acid compounds (ion), acetic acid compounds (ion) speedily react on the component adapted to add a plus electrical charge to the cosmetic prior to the reacting with the polysaccharide of the present invention to neutralize it, and make the apparent charge to a minus charge, whereby the stability of the cosmetic can be effected.

In addition, in order to further stabilize the emulsification of the present invention, hydrophilic components may be added. Examples thereof include amino acid, saccharide and derivatives thereof, (POE methyl glucoside), hydrophilic polymer, low molecular weight polyhydric alcohol, etc.

Examples of amino acid include asparagine, aspartic acid, alanine, arginine, isoleucine, orthinine, glutamine, glycine, glutamic acid, derivatives thereof, and salts thereof, cysteine, cystine, citrulline, threonine, cerine, tyrosine, tryptophan, theanine, valine, histidine, hydroxylysine, hydroxyproline, pyrrolidone carbonate, salts thereof. Examples of saccharide and derivatives thereof include honey, erythritol, maltose, maltitol, xylitol, xylose, pentaerythritol, fructose, dextrine and derivatives thereof, mannitol, sorbitol, inositol, trehalose, glucose, POE methyl glucoside, hydrogenated starch hydrolysates, glucoside trehalose etc.

Examples of hydrophilic polymer include natural high polymers such as xanthan gum, gum arabic, guar gum, karaya gum, carrageenan, pectin, fucoidan, tragant gum, locust bean gum, galactomannan, curdlan, gellant gum, fuco gel, casein, gelatine, starch, collagen, etc., semi-synthetic high polymers such as methyl cellulose, ethyl cellulose, methyl hydroxypropylcellulose, carboxymethylcellulose, hydroxymethylcellulose, hydroxypropylcellulose, sodium carboxymethylcellulose, alginic acid propylene glycol ester, cellulose crystals, sodium acrylate starch, graft copolymer, hydrophobic hydroxypropyl methylcellulose, etc., and synthetic high polymers such as polyvinyl alcohol, polyvinylpyrrolidone, carboxyvinyl polymer, polyacrylic acid salt, polyethyleneoxide, etc. Inorganic minerals such as bentonite, laponite, hectorite, etc. may be used together. Examples of low molecular weight polyhydrous alcohol include ethanol, 1,3-butylene glycol, ethylene glycol, diethylene glycol, triethylene glycol, polyethylene glycol, propylene glycol, dipropylene glycol, glycerin, butanol, propanol, pentanediol, octandiol, 1-(2-ethylhexyl)glycol ether, etc.

The cosmetic in accordance with the present invention can take various kinds of the cosmetic compositions according to their uses thereof, and, if necessary, components to be blended in drugs, quasi-drugs, cosmetics, etc., such as purified water, hot spring water, deep sea water, thickening agents, coloring agents, moisturizers, astringents, whitening agents, UV preventive agents, anti-inflammatory agents, skin (cell) activating agents, antibacterial agents, skin absorbing accelerating agents, carbonated agents, anti-oxidants, antiseptic agents, chelating agents, fade preventive agents, buffering agents, etc. may be added arbitrarily. The present invention does not limit the blending of these various additives provided that the effects of the invention are not damaged.

The cosmetic of the present invention can be used as the cosmetics having various configurations such as preparations for internal use, preparations for injection, etc., other than preparations for external use, but, normally, it is preferable to use as the preparations for external use of drugs, quasi-drugs, cosmetics, etc. The configuration (type of preparation) of the cosmetic is not limited specifically, and solution-shaped, paste-shaped, gel-shaped, solid body-shaped, powder-shaped type of preparations can be possible. In addition, the cosmetic for sunless sunburning can take oils, lotions, creams, milky lotions, jells, shampoos, hair rinses, etc., and the cosmetic of the present invention can be used as hair conditioners, enamels, foundations, lipsticks, face powders, packs, ointments, tablets, injection liquids, granules, capsules, powders, toothpastes, soaps, aerosols, cleansing foams, etc. provided that the effects of the invention are not damaged.

EMBODIMENTS

Hereinafter, the present invention will be explained in details based on the following embodiments, but the present invention is not limited to these embodiments.
(Oily Components Other than Higher Alcohols to be Used in the Present Invention)
(Oily Component (A) to be Used in the Present Invention)
dimethyl polysiloxane (A-1) KF-96-50 c s (trade name); (viscosity 50 mPa·s, 25° C.) (manufactured by Shin-Etsu Chemical Co., Ltd.)

squalane (A-2) ("Kuraray squalane N" (trade name); manufactured by KURARAY CO., LTD)
grape seed oil (A-3) ("Grape Seed Oil" (trade name); Nikko Chemicals Co., Ltd.) olive oil (A-4) ("Cropure OL" (trade name); manufactured by Croda Japan KK) liquid paraffin (A-5) ("Mineral Oil" (trade name); manufactured by B & O Laboratory)
glyceryl tri-2-ethylhexanoate (A-6) ("NIKKOL Trifat S-308" (trade name); manufactured by Nikko Chemicals Co., Ltd.)
caprylic/caproc acid triglyceryl (A-7) ("NIKKOL Triester F-810" (trade name); manufactured by Nikko Chemicals Co., Ltd.)
isostearyl myristate (A-8) ("Cosmol 812" (trade name); manufactured by The Nisshin OilliO Group, Ltd.)
jojoba seed oil (jojoba oil) (A-9) ("Jojoba Oil" (trade name); manufactured by B & O Laboratory)
(Oily Component (B) to be Used in the Present Invention)
chimyl alcohol (B-1) ("NIKKOL Chimil alcohol 100" (trade name); manufactured by Nikko Chemicals Co., Ltd.)
batyl alcohol (B-2) ("NIKKOL Batyl alcohol 100" (trade name); manufactured by Nikko Chemicals Co., Ltd.)
hydroxystearic acid cholesteryl (B-3)("SalakosuHS" (trade name); manufactured by The Nisshin OilliO Group, Ltd.)
di(cholesteryl/behenyl/octyldodecyl)lauroyl glutamate (B-4) ("Eldew CL-301" (trade name); manufactured by AJINOMOTO CO., INC.)
di(cholesteryl/octyldodecyl)lauroyl glutamate (B-5) ("Eldew CL-202" (trade name); manufactured by AJINOMOTO CO., INC.)
di(cholesteryl/behenyl/octyldodecyl)lauroyl glutamate (B-4) ("Eldew CL-301" (trade name); manufactured by AJINOMOTO CO., INC.)
di(cholesteryl.octyldodecyl) N-lauroyl-L-glutamate (B-5) ("Eldew CL-202" (trade name); manufactured by AJINOMOTO CO., INC.)
phytosteryl oleate (B-6) ("SalacosPQ" (trade name); manufactured by The Nisshin OilliO Group, Ltd.)
di(2-octyidodecyl)-N-lauroyl-L-glutamate (B-7) ("Eldew CL-203" (trade name); manufactured by AJINOMOTO CO., INC.)
di(phytosteryl.octydodecyl.behenyl)N-lauroyl-L-glutamate (B-8) ("Eldew CL-304" (trade name); manufactured by AJINOMOTO CO., INC.)
dipentaerythrityl hexahydroxystearate/hexastearate/hexarosinate (B-9) ("Cosmol168AR" (trade name); manufactured by The Nisshin OilliO Group, Ltd.)
dipentaerythrityl hexahydroxystearate (B-10) ("Cosmol168M" (trade name); manufactured by The Nisshin OilliO Group, Ltd.)
glycerye ethylhexanoate/stearate/adipate (B-11)("NomucoatLAH" (trade name); manufactured by The Nisshin OilliO Group, Ltd.)
caprylic/capric/myristic/stearic/triglyceride (B-12) ("Salacos334" (trade name); manufactured by The Nisshin OilliO Group, Ltd.) bees wax (B-13) ("Golden Brand Bleached Bees Wax" (trade name); manufactured by Miki Chemical Industry & Co., Ltd.)
(Polysaccharide)
(1) Polysaccharides (C-1): a Product of a Microorganism of Alcaligenes Latus Strain B-16 (Rough Product)
40.0 g of glucose (Wako Pure chemical Industries, Ltd., reagent), 4.0 g of dipotassium hydrogen phosphate (Wako Pure chemical Industries, Ltd., reagent), 2.0 g of potassium dihydrogen phosphate (Wako Pure chemical Industries, Ltd., reagent), 0.1 g of sodium chloride (Wako Pure chemical Industries, Ltd., reagent), 0.2 g of magnesium sulfate (Wako Pure chemical Industries, Ltd., reagent), 1.0 g of potassium nitrate (Wako Pure chemical Industries, Ltd., reagent), and 1.5 g of yeast extract (OXOID CO. Ltd.) were dissolved in an ion exchange water, and an obtained aqueous solution was adjusted to a pH of 6.5 using sodium hydroxide or sulphuric acid so that the total volume is 1 liter. 150 mL of the obtained aqueous solution was transferred into a 500 mL conical flask and sterilized by autoclaving at 121° C. for 15 minutes. Then, the temperature of the solution was lowered to room temperature, and Alcaligenes latus strain B-16 (FERM BP-2015) was inoculated in the solution in the flask. And the solution was subjected to shaking culture at 30° C. for 6 days (180 rpm). After cultivation, about three volumes of isopropyl alcohol was added thereto and agitated for mixing them. A resultant precipitated aggregations were filtered, recovered and dried under a reduced pressure to obtain polysaccharides of a product of a microorganism of Alcaligenes latus strain B-16 (C-1). This polysaccharide is composed of a polysaccharide containing fucose, glucose, glucuronic acid and rhamnose in a molar ratio of 1:2:1:1, as a main component, and another polysaccharide composed of fucose and mannose in a molar ratio of 1:1. The ratio of the former polysaccharide and the latter polysaccharides is 7:1 (weight ratio). The polysaccharides were hydrolyzed with sulfuric acid, and resultant constituent monosaccharides were analyzed with a high speed liquid chromatography (HPLC).

(2) Polysaccharide (C-2): Purified Product of the Above Polysaccharide (C-1)
An aqueous solution of 0.5% by weight of polysaccharide (C-1) was prepared, and an aqueous solution of sodium hydroxide was added thereto to a pH of 12. The obtained aqueous solution was processed using columns of ion exchange resin "DIAION HPA-75(OH—)(trade name)" (manufactured by Nippon Rensui, CO.) at 8Ru or less, and filtered with a filtration auxiliary "Radiolight RL700" and a membrane filter of 5 µm to remove proteins, nucleic acids, and microbes. After the filtered liquid was adjusted to a pH of 7 with dilute hydrochloric acid, the pressure of the liquid was reduced, and the liquid was concentrated. Then the polysaccharides were precipitated by using acetone, and washed with ten volumes of acetone to obtain a polysaccharide (C-2) composed of fucose, glucose, glucuronic acid and rhamnose in the ratio of 1:2:1:1 and having a molecular weight of fifty million.

(3) Polysaccharide (C-3): Alcasealan (Trade Name, INCI-name: Alcaligenes Polysacchaides; Manufactured by Hakuto CO., LTD.)

(4) Polysaccharide (C-4): a Product of a Microorganism of Sphingomonas trueperiSPH-011 (Rough Product)
50 L of a medium having the following composition was put in a fermentation tank of 90 L, which was manufactured by Marubishi-eg.co., bacteria were decreased, and the sphingomonas trueperiSPH-011(FERM BP-08582) was taken and cultivated. Agitation blades of the cultivation tank are composed of turbine agitation blades, and agitation was carried out in the range of 700 rpm to 800 rpm, and the amount of air was determined to 1 vvm to 2 vm. pH was controlled to the range of 6.5±0.4 using a 1N aqueous solution of NaOH. And, the cultivation temperature was controlled to the range of 30° C.±0.2. The cultivation was carried out for six days. After cultivation, about three volumes of isopropyl alcohol was added thereto and mixed by agitation. A resultant precipitated agglomeration was filtered, recovered and dried under a reduced pressure to obtain a polysaccharide of a product of a microorganism of sphingomonas trueperiSPH-011 (C-4). The polysaccharide (C-4) includes a polysaccharide composed of fucose, glucose, glucuronic acid and rhamnose in a molar ratio of 1:2:1:1, as a main component, and another polysaccharide composed of fucose and mannose in a molar ratio of 2:1. Constituent monosaccharides were analyzed with a high speed liquid chromatography (HPLC) after hydrolyzing the polysaccharide with sulfuric acid.

(5) Polysaccharide (C-5): a Product of a Microorganism of Sphingomonas trueperiSPH-012 (Rough Product)

By carrying out cultivation of the sphingomonas trueperiSPH-012(FERM BP-08579), similarly to the polysaccharide (C-4), a polysaccharide (C-5) was obtained. The polysaccharide (C-5) includes a polysaccharide composed of fucose, glucose, glucuronic acid and rhamnose in a molar ratio of 1:2:1:1 as a main component, and another polysaccharide composed of fucose and mannose in a molar ratio of 1:1.

(6) Polysaccharide (C-6): a Product of a Microorganism of Sphingomonas trueperiSPH-011 (Refined Product)

By adding sodium hydroxide to an aqueous solution of 0.5% by weight of the polysaccharide (C-4) so as to become a concentration of 0.02% by weight, and agitating the same for one night, the polysaccharide was dispersed. In addition, the dispersed solution was dissolved by heating the same at 121° C. for 10 minutes. Then, bacteria were removed by centrifugation (40,000 G, 40 minutes). Whether bacteria were removed or not was judged based on the transparency of a supernatant liquid. Next, the obtained aqueous solution was filtered with the above-described membrane filter to obtain a residue. About three volumes of a pure water was added to this residue, and refilteration was carried out after agitation. This operation was repeated five times, and consequently, components insoluble in water was demineralized. The components insoluble in water, of which water was removed to some degree with the membrane filter system to gel-shaped state, were dried at normal temperature under a reduced pressure, and consequently, the polysaccharide (C-6) that is a product of a microorganism of sphingomonas trueperiSPH-011 was obtained.

(7) Polysaccharide (C-7): a Product of a Microorganism of Sphingomonas trueperiSPH-012 (Refined Product)

By carrying out the separation of the produced polysaccharide in the polysaccharide (C-5), similarly to the polysaccharide (C-6), the polysaccharide (C-7) that is a product of a microorganism of sphingomonas trueperiSPH-012 was obtained.

The composition (composition of 100 mL) of the medium for forming the polysaccharide is as follows:

glucose (manufactured by Wako Pure chemical Industries, Ltd.) 4.0 g dipotassium hydrogen phosphate (manufactured by Wako Pure chemical Industries, Ltd.) 0.40 g potassium dihydrogen phosphate (manufactured by Wako Pure chemical Industries, Ltd.) 0.2 g sodium chloride (manufactured by Wako Pure chemical Industries, Ltd.) 0.01 g magnesium sulfate (manufactured by Wako Pure chemical Industries, Ltd.) 0.02 g potassium nitrate (manufactured by Wako Pure chemical Industries, Ltd.) 0.10 g yeast extract Hy-Yeast 412 (manufactured by Sigma Corporation) 0.15 g 6. Polysaccharide (C-8): Xanthan Gum (KELTROL (Trade Name); CP Kelco) (Higher Alcohol of the Present Invention)

hexadecanol (D-1) ["HAINOL 16SS (hexadecanol 99% or more, melting point 49 to 53° C.)" (trade name); manufactured by Kokyu Alcohol Kogyo Co., Ltd.]

octadecanol (D-2) ["HAINOL 18SS (octadecanol 99% or more, melting point 55 to 60° C.)" (trade name); manufactured by Kokyu Alcohol Kogyo Co., Ltd.]

eicosanol (D-3) ["HAINOL 20SS (eicosanol 95% or more, melting point 60 to 65° C.)" (trade name); manufactured by Kokyu Alcohol Kogyo Co., Ltd.]

docosanol (D-4) ["HAINOL 22S (docosanol 97% or more, melting point 67 to 73° C.)" (trade name); manufactured by Kokyu Alcohol Kogyo Co., Ltd.]

cetostearyl alcohol (D-5) ["CETOSTEARYL ALCOHOL (hexadecanol 50%, octadecanol 50%, melting point 54 to 56° C.)" (trade name); manufactured by Kokyu Alcohol Kogyo Co., Ltd.]

behenyl alcohol (D-6) ["BEHENYL ALCOHOL (docosanol 65 to 70%, eicosanol 10 to 20%, octadecanol 10 to 20%, melting point 65 to 73° C.)" (trade name); manufactured by Kokyu Alcohol Kogyo Co., Ltd.]

hydrogenated rapeseed oil alcohol (D-7) ["ALCOHOL No. 20-B (octadecanol 40%, docosanol 50%, melting point 60 to 70° C.)] (trade name); manufactured by Kokyu Alcohol Kogyo Co., Ltd.]

(Titanium Dioxide)

(1) titania sol (E-0): By neutralizing an aqueous solution of titanium(IV) chloride ($TiO_2$ 200 g/l) with an aqueous solution of sodium hydroxide while keeping the aqueous solution of titanium(IV) chloride at room temperature, thereby precipitating colloidal non-crystal titanium hydroxide, and aging the same to prepare a rutile type micro titania sol (E-0).

(2) Titanium dioxide (E-1): Silicon dioxide ($SiO2$ 320 g/l) and sodium hydroxide NaOH 480 g/L were mixed and reacted with each other to prepare water glass ($Na_2SiO_3$). An aqueous solution of this water glass: 220 mL (in terms of $SiO2$ 180 g/L) were added to 1000 mL of a micro titania sol dispersion liquid (E-0) along with sulphuric acid to deposit silicic acid on surfaces of titanium dioxide, thereby forming films. And, by adding an aqueous solution of sodium hydroxide of 2N at a rate of about 1 mL/minute for 60 minutes, pH was adjusted to 8. Then, after pH was adjusted with sulphuric acid to 7, the solution was aged for 60 minutes while agitating, whereby a slurry of titanium dioxide microparticles coated with hydrous silicic acid was obtained. Next, by filtering, washing with water, and drying this slurry, a powder body was obtained. By pulverizing this powder body for 20 seconds using a hammer mill, titanium dioxide (E-1) was obtained. The particle diameter of the coated powder body after pulverized was distributed between 0.05 μm and 3 μm, and the average particle diameter was 0.5 μm.

(3) titanium dioxide (E-2): MT-150W (trade name) (titanium dioxide coated with sodium metaphosphate; manufactured by Tayca Corporation)

(4) titanium dioxide (E-3): MT-01 (trade name) (titanium dioxide coated with aluminium hydroxide, stearic acid; manufactured by Tayca Corporation)

(5) titanium dioxide (E-4): MT-100AQ (trade name) (titanium dioxide coated with aluminium hydroxide, hydrous silicic acid, sodium alginate; manufactured by Tayca Corporation)

(6) titanium dioxide (E-5): MT-100SA (trade name) (titanium dioxide coated with aluminium hydroxide, hydrous silicic acid; manufactured by Tayca Corporation)

titanium dioxide (E-6): MT-02 (trade name) titanium dioxide coated with methicone, monomethyl polysiloxane; manufactured by Tayca Corporation)

(Inorganic Salt)

(1) tripotassium phosphate (F-1) (reagent; manufactured by TAIHEI CHEMICAL INDUSTRIAL CO., LTD.)

(2) trisodium phosphate (F-2) (reagent; manufactured by TAIHEI CHEMICAL INDUSTRIAL CO., LTD.)

(3) potassium metaphosphate (F-3) (reagent; manufactured by TAIHEI CHEMICAL INDUSTRIAL CO., LTD.)

(4) sodium metaphosphate (F-4) (reagent; manufactured by TAIHEI CHEMICAL INDUSTRIAL CO., LTD.)
(5) sodium pyrophosphate (F-5) (reagent; manufactured by TAIHEI CHEMICAL INDUSTRIAL CO., LTD.)
(6) sodium tripolyphosphate (F-6) (reagent; manufactured by TAIHEI CHEMICAL INDUSTRIAL CO., LTD.)
(7) sodium tetrapolyphosphate (F-7) (reagent; manufactured by TAIHEI CHEMICAL INDUSTRIAL CO., LTD.)
(8) sodium pentapolyphosphapte (F-8) (reagent; manufactured by TAIHEI CHEMICAL INDUSTRIAL CO., LTD.)
(9) potassium pyrophosphate (F-9) (reagent; manufactured by TAIHEI CHEMICAL INDUSTRIAL CO., LTD.)
(10) potassium tripolyphosphate (F-10) (reagent; manufactured by TAIHEI CHEMICAL INDUSTRIAL CO., LTD.)
(11) potassium tetrapolyphosphate (F-11) (reagent; manufactured by TAIHEI CHEMICAL INDUSTRIAL CO., LTD.)
(12) potassium pentapolyphosphate (F-12) (reagent; manufactured by TAIHEI CHEMICAL INDUSTRIAL CO., LTD.)
(13) sodium citrate (F-13) (reagent; manufactured by KANTO CHEMICAL CO., INC.)
(14) potassium citrate (F-14) (reagent; manufactured by KANTO CHEMICAL CO., INC.)
(15) hydroxyethane diphosphonic acid (F-15) (reagent; manufactured by CHELEST CORPORATION)
(16) diethylenetriamine pentaacetic acid (F-16) (reagent; manufactured by CHELEST CORPORATION)

The composition of sunscreen 1-1 as an embodiment 1 in accordance with the present invention is shown in Table 1.

TABLE 1

| Section | Components | % by weight |
|---|---|---|
| a | glycerin (glycerin S, Sakamoto Yakuhin Kogyo Co., Ltd.) | 5.00 |
|  | 1,3-buthyleneglycol (1,3BG, DAICEL CHEMICAL INDUSTRIES, LTD.) | 5.00 |
|  | 1-(2-ethyl hexyl) glycol ether (sencibaSC50, SEIWA KASEI Co., Ltd.) | 0.30 |
|  | 1,2-pentandiol (diolPD, Nikko Chemicals Co., Ltd.) | 3.00 |
|  | titanium dioxide coated with hydrous silicic acid (E-1) | 7.00 |
| b | cetostearyl alcohol (D-5) | 4.00 |
|  | dimethyl polysiloxane (A-1) | 2.00 |
|  | isostearyl myristate (A-8) | 1.00 |
|  | squalane (A-2) | 8.00 |
|  | olive oil (A-4) | 3.00 |
|  | liquid paraffin (A-5) | 1.00 |
|  | glyceryl tri-2-ethylhexanoate (A-6) | 2.00 |
| c | polysaccharide (C-1) | 0.06 |
|  | purified water | balance |

1. The polysaccharide (C-1) of Section c was heated to 80° C., and dispersed in purified water using a disperser to prepare a dispersion liquid of polysaccharide (C-1) and water.
2. Components of Section b were respectively weighed, mixed homogeneously, and dissolved by heating to 80° C., whereby a mixture liquid 1 was prepared.
3. Components of Section a were respectively weighed, and dissolved by heating at 80° C., whereby a mixture liquid 2 was prepared.
4. The mixture liquid 2 was added to the dispersion liquid of polysaccharide (C-1) and water, and the mixture liquid 1 was gradually added while operating the homogenizer or homomixer at 8000 rotations. After added, a mixture liquid was agitated for 10 minutes, and cooled to room temperature while agitating, whereby sunscreen 1-1 (Embodiment 1) was obtained.

Hereinafter, (Embodiment 2: sunscreen 1-2)~(Embodiment 7: sunscreen 1-7) and (Comparative example 1: sunscreen 1-8)~(Comparative example 8: sunscreen 1-14) will be shown.

Embodiment 2

Sunscreen 1-2

By replacing polysaccharide (C-1) of Section c of Embodiment 1 with the same amount of polysaccharide (C-2), sunscreen 1-2 (Embodiment 2) was obtained.

Embodiment 3

Sunscreen 1-3

By replacing polysaccharide (C-1) of Section c of Embodiment 1 with the same amount of polysaccharide (C-3), sunscreen 1-3 (Embodiment 3) was obtained.

Embodiment 4

Sunscreen 1-4

By replacing polysaccharide (C-1) of Section c of Embodiment 1 with the same amount of polysaccharide (C-4), sunscreen 1-4 (Embodiment 4) was obtained.

Embodiment 5

Sunscreen 1-5

By replacing polysaccharide (C-1) of Section c of Embodiment 1 with the same amount of polysaccharide (C-5), sunscreen 1-5 (Embodiment 5) was obtained.

Embodiment 6

Sunscreen 1-6

By replacing polysaccharide (C-1) of Section c of Embodiment 1 with the same amount of polysaccharide (C-6), sunscreen 1-6 (Embodiment 6) was obtained.

Embodiment 7

Sunscreen 1-7

By replacing polysaccharide (C-1) of Section c of Embodiment 1 with the same amount of polysaccharide (C-7), sunscreen 1-7 (Embodiment 7) was obtained.

Comparative Example 1

Sunscreen 1-8

By replacing polysaccharide (C-1) of Section c of Embodiment 1 with the same amount of xanthan gum (KELTROL (trade name); CP Kelco), and adding 1% by weight of sucrose myristate ester (M-160 (trade name); DAIICHI KOGYO SEIYAKU CO., LTD.) to Section a, sunscreen 1-8 (Comparative example 1) was obtained.

Comparative Example 2

Sunscreen 1-9

By replacing polysaccharide (C-1) of Section c of Embodiment 1 with the same amount of hydroxymethyl cellulose (METOLOSE (trade name); Shin-Etsu Chemical Co., Ltd.), and adding 1% by weight of sucrose myristate ester (M-160 (trade name); DAIICHI KOGYO SEIYAKU CO., LTD.) to Section a, sunscreen 1-9 (Comparative example 2) was obtained.

Comparative Example 3

Sunscreen 1-10

By replacing titanium dioxide (E-1) of Section a of Embodiment 3 with the same amount of titanium dioxide (E-2), sunscreen 1-10 (Comparative example 3) was obtained.

Comparative Example 4

Sunscreen 1-11

By replacing titanium dioxide (E-1) of Section a of Embodiment 3 with the same amount of titanium dioxide (E-3), sunscreen 1-11 (Comparative example 4) was obtained.

Comparative Example 5

Sunscreen 1-12

By replacing titanium dioxide (E-1) of Section a of Embodiment 3 with the same amount of titanium dioxide (E-4), sunscreen 1-12 (Comparative example 5) was obtained.

Comparative Example 6

Sunscreen 1-13

By replacing titanium dioxide (E-1) of Section a of Embodiment 3 with the same amount of titanium dioxide (E-5), sunscreen 1-13 (Comparative example 6) was obtained.

Comparative Example 7

Sunscreen 1-14

By replacing titanium dioxide (E-1) of Section a of Embodiment 3 with the same amount of titanium dioxide (E-6), sunscreen 1-14 (Comparative example 7) was obtained.

Comparative Example 8

Sunscreen 1-15

By adding sucrose myristate ester (M-160 (trade name); DAIICHI KOGYO SEIYAKU CO., LTD.) to Section a of Embodiment 3 in an amount of 1 g/100 ml), sunscreen 1-15 (Comparative example 8) was obtained.

Embodiment 8

Sunscreen 2-1

The composition of sunscreen 2-1 will be shown in Table 2.

TABLE 2

| Section | Components | % by weight |
|---|---|---|
| a | glycerin (glycerin S, Sakamoto Yakuhin Kogyo Co., Ltd.) | 5.00 |
|   | 1,3-buthyleneglycol (1, 3BG, DAICEL CHEMICAL INDUSTRIES, LTD.) | 5.00 |
|   | methylparaben (MekkinsM, UENO FINE CHEMICALS INDUSTRY, LTD.) | 0.15 |
|   | titanium dioxide coated with hydrous silicic acid (E-1) | 7.00 |
| b | behenyl alcohol (D-6) | 4.00 |
|   | dimethyl polysiloxane (A-1) | 2.00 |
|   | isostearyl myristate (A-8) | 1.00 |
|   | squalane (A-2) | 6.00 |
|   | olive oil (A-4) | 3.00 |
| c | polysaccharide (C-3) | 0.06 |
|   | purified water | balance |
|   | tripotassium phosphate(F-1) | 0.20 |
| d | L-Ascorbic Acid 2-Glucoside (AS-G, HAYASHIBARA BIOCHEMICAL LABS., INC.) | 2.00 |
|   | L-arginine (KANTO CHEMICAL CO., LTD.) | 0.70 |
|   | water | 8.50 |

1. Polysaccharide (C-3) of Section c was heated to 80° C., and dispersed in purified water using a disperser to prepare a dispersion liquid of polysaccharide (C-3) and water.

2. Components of Section b were respectively weighed, mixed homogeneously, and dissolved by heating at 80° C., whereby a mixture liquid 1 was prepared.

3. Components of Section a were respectively weighed, and dissolved by heating at 80° C., whereby a mixture liquid 2 was prepared.

4. The mixture liquid 2 was added to the dispersion liquid of polysaccharide (C-3) and water, and the mixture liquid 1 was gradually added while operating the homogenizer or homomixer at 8000 rotations. After added, a mixture liquid was agitated for 10 minutes, and cooled to room temperature while agitating.

5. After cooled, the components of Section d were added and mixed by agitating, whereby sunscreen 2-1 (Embodiment 8) was obtained.

Hereinafter, (Embodiment 9: sunscreen 2-2)~(Embodiment 19: sunscreen 2-12) and (Comparative example 9: sunscreen 2-13)~(Comparative example 10: sunscreen 2-14) will be shown.

Embodiment 9

Sunscreen 2-2

By replacing phosphate (F-1) of Section c of Embodiment 8 with the same amount of phosphate (F-2), sunscreen 2-2 (Embodiment 9) was obtained.

Embodiment 10

Sunscreen 2-3

By replacing phosphate (F-1) of Section c of Embodiment 8 with the same amount of phosphate (F-3), sunscreen 2-3 (Embodiment 10) was obtained.

Embodiment 11

Sunscreen 2-4

By replacing phosphate (F-1) of Section c of Embodiment 8 with the same amount of phosphate (F-4), sunscreen 2-4 (Embodiment 11) was obtained.

Embodiment 12

Sunscreen 2-5

By replacing phosphate (F-1) of Section c of Embodiment 8 with the same amount of phosphate (F-5), sunscreen 2-5 (Embodiment 12) was obtained.

Embodiment 13

Sunscreen 2-6

By replacing phosphate (F-1) of Section c of Embodiment 8 with the same amount of phosphate (F-6), sunscreen 2-6 (Embodiment 13) was obtained.

Embodiment 14

Sunscreen 2-7

By replacing phosphate (F-1) of Section c of Embodiment 8 with the same amount of phosphate (F-7), sunscreen 2-7 (Embodiment 14) was obtained.

Embodiment 15

Sunscreen 2-8

By replacing phosphate (F-1) of Section c of Embodiment 8 with the same amount of phosphate (F-8), sunscreen 2-8 (Embodiment 15) was obtained.

Embodiment 16

Sunscreen 2-9

By replacing phosphate (F-1) of Section c of Embodiment 8 with the same amount of phosphate (F-9), sunscreen 2-9 (Embodiment 16) was obtained.

Embodiment 17

Sunscreen 2-10

By replacing phosphate (F-1) of Section c of Embodiment 8 with the same amount of phosphate (F-10), sunscreen 2-10 (Embodiment 17) was obtained.

Embodiment 18

Sunscreen 2-11

By replacing phosphate (F-1) of Section c of Embodiment 8 with the same amount of phosphate (F-11), sunscreen 2-11 (Embodiment 18) was obtained.

Embodiment 19

Sunscreen 2-12

By replacing phosphate (F-1) of Section c of Embodiment 8 with the same amount of phosphate (F-12), sunscreen 2-12 (Embodiment 19) was obtained.

Embodiment 20

Sunscreen 2-13

By replacing phosphate (F-1) of Section c of Embodiment 8 with the same amount of sodium citrate (F-13), sunscreen 2-13 (Embodiment 20) was obtained.

Embodiment 21

Sunscreen 2-14

By replacing phosphate (F-1) of Section c of Embodiment 8 with the same amount of potassium citrate (F-14), sunscreen 2-14 (Embodiment 21) was obtained.

Embodiment 22

Sunscreen 2-15

By replacing phosphate (F-1) of Section c of Embodiment 8 with the same amount of hydroxyethane diphosphonic acid (F-15), sunscreen 2-15 (Embodiment 22) was obtained.

Embodiment 23

Sunscreen 2-16

By replacing phosphate (F-1) of Section c of Embodiment 8 with the same amount of diethylenetriamine pentaacetic acid (F-16), sunscreen 2-16 (Embodiment 23) was obtained.

Comparative Example 9

Sunscreen 2-17

By replacing phosphate (F-1) of Section c of Embodiment 8 with the same amount of water, sunscreen 2-17 (Comparative example 9) was obtained.

Comparative Example 10

Sunscreen 3

The composition of the sunscreen 3 will be shown in Table 3.

TABLE 3

| Section | Components | % by weight |
|---|---|---|
| a | glycerin (glycerin S, Sakamoto Yakuhin Kogyo Co., Ltd.) | 5.00 |
| | 1,3-buthyleneglycol (1,3BG, DAICEL CHEMICAL INDUSTRIES, LTD.) | 5.00 |
| | 1-(2-ethyl hexyl)glycol ether (sencibaSC50, SEIWA KASEI Co., Ltd.) | 0.30 |
| | 1,2-pentandiol (diolPD, Nikko Chemicals Co., Ltd.) | 3.00 |
| | sucrose myristate ester (M-160 (trade name); DAIICHI KOGYO SEIYAKU CO., LTD.) | 1.00 |

TABLE 3-continued

| Section | Components | % by weight |
|---|---|---|
| b | titanium dioxide (E-3) | 7.00 |
| | trimethylsiloxysilicate (DC593-560cs, Dow Corning Toray Co., Ltd.) | 2.00 |
| | dimethyl polysiloxane (A-1) | 2.00 |
| | decamethylcyclopentasiloxane (KF-995, Shin-Etsu Chemical Co., Ltd.) | 3.00 |
| | crosslinked methylphenylpolysiloxane (KSG-18 base oil 80-90%, Shin-Etsu Chemical Co., Ltd.) | 2.00 |
| c | isostearyl myristate (A-8) | 1.00 |
| | sqalane (A-2) | 8.00 |
| | glyceryl tri-2-ethylhexanoate (A-6) | 2.00 |
| d | polysaccharide (C-3) | 0.06 |
| | purified water | balance |

1. Polysaccharide (C-3) of Section d was heated to 80° C., and dispersed in purified water using a disperser to prepare a dispersion liquid of polysaccharide (C-3) and water.
2. Components of Section b were respectively weighed, mixed homogeneously, and dissolved by heating at 80° C., whereby a mixture liquid 1 was prepared.
3. Components of Section c were respectively weighed, mixed homogeneously, and dissolved by heating at 80° C., whereby a mixture liquid 2 was prepared.
4. Components of Section a were respectively weighed, and dissolved by heating at 80° C., whereby a mixture liquid 3 was prepared.
5. The mixture liquid 3 was gradually added to the mixture liquid 1 and mixed therewith to prepare a mixture liquid 4.
6. The mixture liquid 4 was gradually added while agitating the dispersion liquid of polysaccharide (C-3) and water with the homogenizer or homomixer at 8000 rotations. After added, a mixture liquid was agitated for 10 minutes to prepare a mixture liquid 5.
7. The mixture liquid 2 was gradually added to the mixture liquid 5 while agitating. Then, the mixture liquid 4 was gradually added and agitated for 10 minutes. After cooled to room temperature, sunscreen 3 (Comparative example 10) was obtained.

(Stability Test of Cosmetic)

The stability test was carried out using the prepared sunscreen 1 (Embodiments 1 through 7 and Comparative examples 1 through 8), the sunscreen 2 (Embodiments 8 through 23 and Comparative example 9), and the sunscreen 3 (Comparative example 10). The cosmetics just after being prepared were sampled in sample bottles of 200 mL, the bottles were sealed and placed in a thermostatic chamber at 5° C., 50° C. and with a cycle (repetition of −10° C. for one day, and 50° C. for one day), and after 1 week, and 3 months, the visual observation of the stability of the cosmetics was performed. The cosmetics in which no separation nor precipitation is observed are preferable. The test results are shown in Tables, 4, 5 and 6.

(Evaluation Criteria of Stability)

○: separation or precipitation is not observed visually; and
x: separation and precipitation are observed visually (Water Resistance Test of Cosmetic)

The water resistance test was carried out using the prepared sunscreen 1 (Embodiments 1 through 7 and Comparative examples 1 through 8), the sunscreen 2 (Embodiments 8 through 23 and Comparative example 9), and the sunscreen 3 (Comparative example 10). After 0.5 g of sunscreen just after being prepared is homogeneously applied to a rear surface of a filter paper No. 2 having 30 mm per side (manufactured by Advantec MFS, Inc.), the filter paper was dried at 105° C. for 1 hour, and weighed. The filter paper was immersed in a 100 mL of purified water put in a beaker of 200 mL for 30 minutes with a dried surface thereof faced downwardly, and the filter paper was removed from water, dried at 105° C. for 1 hour, and weighed. The flow rate (%) of the cosmetic was calculated according to the following equation, and the water resistance was evaluated. As the flow rate (%) decreases, the cosmetic does not flow with water and exhibits an elevated water resistance so as to be preferable.

Flow rate(%)=[{(weight before immersion)−(weight after immersion)}/(weight before immersion)]×100

The test results were listed in Tables 4, 5 and 6.

TABLE 4

| | Separation and precipitation | | | | | | Flow rate (%) |
|---|---|---|---|---|---|---|---|
| | After 1 week | | | After 3 months | | | |
| Cosmetic | 5° C. | 50° C. | cycle | 5° C. | 50° C. | cycle | |
| Embodiment 1 | stable | stable | stable | stable | stable | stable | 35.2 |
| Embodiment 2 | stable | stable | stable | stable | stable | stable | 34.8 |
| Embodiment 3 | stable | stable | stable | stable | stable | stable | 33.7 |
| Embodiment 4 | stable | stable | stable | stable | stable | stable | 36.0 |
| Embodiment 5 | stable | stable | stable | stable | stable | stable | 33.5 |
| Embodiment 6 | stable | stable | stable | stable | stable | stable | 32.9 |
| Embodiment 7 | stable | stable | stable | stable | stable | stable | 35.6 |
| Comparative example 1 | water separation | water separation | water separation | — | — | — | 34.1 |
| Comparative example 2 | water separation | water separation | water separation | — | — | — | 37.4 |
| Comparative example 3 | water separation | water separation | water separation | — | — | — | 38.7 |
| Comparative example 4 | water separation | water separation | water separation | — | — | — | 38.5 |
| Comparative example 5 | water separation | water separation | water separation | — | — | — | 34.0 |
| Comparative example 6 | water separation | water separation | water separation | — | — | — | 37.7 |
| Comparative example 7 | water separation | water separation | water separation | — | — | — | 35.3 |

TABLE 4-continued

| | Separation and precipitation | | | | | | Flow rate (%) |
|---|---|---|---|---|---|---|---|
| | After 1 week | | | After 3 months | | | |
| Cosmetic | 5° C. | 50° C. | cycle | 5° C. | 50° C. | cycle | |
| Comparative example 8 | stable | stable | stable | stable | stable | stable | 46.2 |

The sunscreens of the present invention (Embodiments 1~7) maintained stability over 3 months or more under the storage condition of 5° C., 50° C., and cycle (repetition of −10° C. for one day, and 50° C. for one day), and the flow rate into water is 40% or less so as to exhibit a high water resistance. On the other hand, the conventional sunscreens, which use titanium dioxide, (Comparative examples 1 through 7) can restrain the flow into water, but the stability of the emulsified state thereof was 1 week or less. In addition, comparative example 8 using hydrate silica subjected to the surface treatment, and containing surfactants was high in storage stability, but had a flow rate of 46.2% so as not to exhibit a preferable water resistance.

TABLE 5

| | Separation and precipitation | | | | | | Flow rate (%) |
|---|---|---|---|---|---|---|---|
| | After 1 week | | | After 3 months | | | |
| Cosmetic | 5° C. | 50° C. | cycle | 5° C. | 50° C. | cycle | |
| Embodiment 8 | stable | stable | stable | stable | stable | stable | 38.3 |
| Embodiment 9 | stable | stable | stable | stable | stable | stable | 39.1 |
| Embodiment 10 | stable | stable | stable | stable | stable | stable | 37.4 |
| Embodiment 11 | stable | stable | stable | stable | stable | stable | 37.7 |
| Embodiment 12 | stable | stable | stable | stable | stable | stable | 37.2 |
| Embodiment 13 | stable | stable | stable | stable | stable | stable | 38.6 |
| Embodiment 14 | stable | stable | stable | stable | stable | stable | 39.0 |
| Embodiment 15 | stable | stable | stable | stable | stable | stable | 37.2 |
| Embodiment 16 | stable | stable | stable | stable | stable | stable | 38.4 |
| Embodiment 17 | stable | stable | stable | stable | stable | stable | 37.6 |
| Embodiment 18 | stable | stable | stable | stable | stable | stable | 38.1 |
| Embodiment 19 | stable | stable | stable | stable | stable | stable | 37.9 |
| Comparative example 9 | stable | stable | stable | stable | stable | Water separation | 38.3 |

* The flow rate in the case no flow occurred is 36%, and the flow rate in the case titanium dioxide flowed entirely is 56%.

It has been clarified that the sunscreens of the present invention (Embodiments 8~19) maintain stability over 3 months or more, and exhibit the flow rate of 40% or less into water so as to have a high water resistance under the storage condition of 5° C., 50° C., and cycle (repetition of −10° C. for one day, and 50° C. for one day), even when ascorbic acid glucoside that makes emulsification instable is added. In Comparative example 9 containing no phosphate, etc., the water resistance and stability were exhibited, but the stability under the cycle condition was inferior so that separation occurred after 3 months.

(Soap Cleansing Test—Evaluation of Good Feeling)

2 g of each of the cosmetics just after preparation, the sunscreen 1-1 (Embodiment 1) and the sunscreen 3 (Comparative example 10) were spread on skin of each of ten panelers so as to blend into skin. After one hour, namely, after the moisture content sufficiently evaporates, faces were cleansed with soaps, and the removing degree thereof was evaluated. The evaluation was performed by the sensory test of "stickiness" and "fresh good feel" thereof. And after cleansing, the cosmetics, etc. were wiped away with cotton wetted with 1 g of cyclopentasiloxane (KF-995 Shin-Etsu Chemical Co., Ltd.), and wiped results were evaluated by visual observation. It is preferable that wiped results are not good, because the removing properties with cleansing are high. The evaluation results are shown in TABLE 7.

TABLE 6

| | Separation and precipitation | | | | | | Flow rate (%) |
|---|---|---|---|---|---|---|---|
| | After one week | | | After three months | | | |
| Cosmetic | 5° C. | 50° C. | cycle | 5° C. | 50° C. | cycle | |
| Comparative example 10 | stable | stable | stable | stable | stable | stable | 35.1 |

* The flow rate in the case no flow occurred is 33%, and the flow rate in the case titanium dioxide flowed entirely is 56%.

TABLE 7

| | Sensory test after face-cleansing | | | Wiping test | | |
|---|---|---|---|---|---|---|
| | | | | | Titanium | |
| Cosmetic | Fresh and good | sticky | not fresh and not sticky | Titanium dioxide attached | dioxde not attached | Cleansing properties with soap |
| Embodiment 1 | 8 people | 0 people | 2 people | 1 people | 9 people | good |
| Embodiment 2 | 9 people | 0 people | 1 people | 1 people | 9 people | good |

TABLE 7-continued

| Cosmetic | Sensory test after face-cleansing | | | Wiping test | | Cleansing properties with soap |
| --- | --- | --- | --- | --- | --- | --- |
| | Fresh and good | sticky | not fresh and not sticky | Titanium dioxde attached | Titanium dioxde not attached | |
| Embodiment 3 | 8 people | 0 people | 2 people | 1 people | 9 people | good |
| Embodiment 4 | 8 people | 0 people | 2 people | 2 people | 8 people | good |
| Embodiment 5 | 9 people | 0 people | 1 people | 0 people | 10 people | good |
| Embodiment 6 | 8 people | 0 people | 2 people | 1 people | 9 people | good |
| Embodiment 7 | 9 people | 0 people | 1 people | 0 people | 10 people | good |
| Embodiment 8 | 8 people | 0 people | 2 people | 1 people | 9 people | good |
| Embodiment 9 | 9 people | 0 people | 1 people | 0 people | 10 people | good |
| Embodiment 10 | 8 people | 0 people | 2 people | 1 people | 9 people | good |
| Embodiment 11 | 9 people | 0 people | 1 people | 1 people | 9 people | good |
| Embodiment 12 | 8 people | 0 people | 2 people | 2 people | 8 people | good |
| Embodiment 13 | 10 people | 0 people | 1 people | 0 people | 10 people | good |
| Embodiment 14 | 8 people | 0 people | 2 people | 1 people | 9 people | good |
| Embodiment 15 | 8 people | 0 people | 2 people | 1 people | 9 people | good |
| Embodiment 16 | 8 people | 0 people | 2 people | 1 people | 9 people | good |
| Embodiment 17 | 9 people | 0 people | 1 people | 0 people | 10 people | good |
| Embodiment 18 | 8 people | 0 people | 2 people | 1 people | 9 people | good |
| Embodiment 19 | 8 people | 0 people | 2 people | 2 people | 8 people | good |
| Comparative example 8 | 8 people | 0 people | 2 people | 1 people | 9 people | good |
| Comparative example 10 | 1 people | 6 people | 3 people | 10 people | 0 people | bad |

It is clear that in Embodiment 1 of the present invention, the sunscreen can be readily washed away only by cleansing faces with soaps. On the other hand, as shown in Table 6, in the case of Comparative example 10 using titanium dioxide subjected to no surface treatment with hydrous silica, surfactants, and high viscosity silicone compounds, the sunscreen is restrained from flowing out into water so as to exhibit a high water resistance and a high stability. However, as shown in Table 7, it cannot be washed away with soaps, and by wiping after cleansing faces, a large amount of the cosmetic adhered to cotton. It is clear from this result that the cosmetic remains on skin after cleansed. In addition, Comparative example 8 is inferior in water resistance, as shown in Table 4, but can be cleansed with soaps, as shown in Table 7. The present invention is excellent in cleansing properties with soaps, and is also excellent in water resistance, as shown in Tables 4 and 5.

Embodiments 20 through 105 in accordance with the present invention and Comparative examples 11 through 25 will be explained.

[Preparation and Evaluation (1) of Emulsified Substances of Higher Alcohol]

Embodiments 20 Through 38

0.2 g of methyl p-hydroxybenzoate was added to 159.7 g of a warm water of 80° C., 0.1 g of polysaccharide (C-3) was further added thereto, and a resultant mixture was agitated for 10 minutes while rotating a homomixer (manufactured by IKA) at 16,000 rpm A, thereby dissolving the polysaccharide therein. Next, 10 g of the higher alcohol (D-1), 10 g of the higher alcohol (D-2), 5 g of dimethylpolysiloxane (A-1), 5 g of squalane (A-2), 5 g of liquid paraffin, 5 g of glyceryl tri-2-ethylhexanoate (A-6) heated to 80° C. were mixed together while agitating a homomixer (manufactured by IKA) at 16,000 rpm paraffin), and were continuously agitated for five minutes to be emulsified. Next, by decreasing the agitating rate to 13,000 rpm, cooling the mixture to 40° C. with a cold water in 10 minutes, and further cooling the mixture to 25° C. with an ice cold water in 5 minutes, an emulsified substance of Embodiment 20 was obtained. Similarly, emulsified substances of Embodiments 21 trough 30, and Embodiments 32 through 38 were obtained by using 20 g of a combination of two or more kinds of the higher alcohols (D-2) through (D-7), and an emulsified substance of Embodiment 31 was obtained by using 40 g of the higher alcohol (D-7).

Embodiments 39 Through 47

0.2 g of methyl p-hydroxybenzoate as an antiseptic agent was added to 159.7 g of a warm water of 80° C., 0.1 g of polysaccharide (C-1) was further added thereto, and a resultant mixture was agitated for 10 minutes while rotating a homomixer (manufactured by IKA) at 16,000 rpm, thereby dissolving the polysaccharide. Next, 10 g of the behenyl alcohol (D-6), 10 g of the hydrogenated rapeseed oil alcohol (D-7), 5 g of caprylic/capric/myristic/stearic/triglyceride (B-12), 5 g of bees wax (B-13), 5 g of batyl alcohol (B-2), 5 g of dipentaerythrityl hexylydroxystearate (B-10) heated to 80° C. were mixed together while agitating for 5 minutes for emulsification. Next, by decreasing the agitating rate to 13,000 rpm, cooling the mixture to 40° C. with a cold water in 10 minutes, and further cooling the mixture to 25° C. with an ice cold water in 5 minutes, an emulsified substance of Embodiment 39 was obtained. Similarly, emulsified substances of Embodiments 40 trough 47 were obtained by replacing polysaccharide (C-1) with polysaccharides (C-2) through (C-7).

Comparative Example 11

0.2 g of methyl p-hydroxybenzoate was added to 189.7 g of a warm water of 80° C., 0.1 g of polysaccharide (C-3) was further added thereto, and a resultant mixture was agitated for 10 minutes while rotating a homomixer (manufactured by IKA) at 16,000 rpm, thereby dissolving the polysaccharide therein. Next, 10 g of higher alcohol (D-1) heated to 80° C. was mixed while agitating for 5 minutes for emulsification.

Next, by decreasing the agitating rate to 13,000 rpm, cooling the mixture to 40° C. with a cold water in 10 minutes, and further cooling the mixture to 25° C. with an ice cold water in 5 minutes, an emulsified substance of comparative example 11 was obtained.

Comparative Examples 12 Through 16

The comparative examples 12 through 16 correspond to Embodiments 20 through 23, and were prepared by using 10 g of only one kind of higher alcohol out of higher alcohols (D-1) through (D-4). And Comparative example 16 was prepared by replacing 10 g of higher alcohol (D-1) and 10 g of higher alcohol (D-2) of Embodiment 20 with 20 g of a warm water.

(Sensory Test of Emulsified Substances of Higher Alcohols)

Obtained emulsified substances of higher alcohols were applied to skin, and sensory tests of the feel against skin were performed. And they were evaluated as follows:

○: well blending into skin x: not well blending into skin, water repelling or oil repelling occurred on skin with repelling feel.

Further, in order to evaluate the stability of the emulsified substances by visual observation, 50 g of emulsified substances were put in glass vessels, sealed, and placed in a thermostatic chamber with a cycle of −10° C. (24 hours) to 50° C. (24 hours). And evaluation was performed such that ○: an emulsified state is maintained.

x: oil contents float on surface, or emulsification phases separate as an upper part, and separation between a water phase and an oil phase is observed. The evaluation results are as follows.

TABLE 8

| Example | No | Composition and content (wt %) | | | Stability | | Feel |
| --- | --- | --- | --- | --- | --- | --- | --- |
| | | Polysaccharide | Higher alcohol | Oily component | 1 week | 1 month | |
| Embodiment | 20 | C-3:0.05 | D-1:5, D-2:5 | A-1:2.5 | ○ | ○ | ○ |
| | 21 | | D-1:5, D-3:5 | A-2:2.5 | ○ | ○ | ○ |
| | 22 | | D-1:5, D-4:5 | A-5:2.5 | ○ | ○ | ○ |
| | 23 | | D-1:5, D-5:5 | A-6:2.5 | ○ | ○ | ○ |
| | 24 | | D-1:5, D-6:5 | | ○ | ○ | ○ |
| | 25 | | D-1:5, D-7:5 | | ○ | ○ | ○ |
| | 26 | | D-2:5, D-3:5 | | ○ | ○ | ○ |
| | 27 | | D-3:5, D-4:5 | | ○ | ○ | ○ |
| | 28 | | D-1:2.5, D-2:2.5 D-3:2.5, D-4:2.5 | | ○ | ○ | ○ |
| | 29 | | D-5:10 | | ○ | ○ | ○ |
| | 30 | | D-7:10 | | ○ | ○ | ○ |
| | 31 | | D-7:20 | | ○ | ○ | ○ |
| | 32 | | D-6:5, D-7:5 | | ○ | ○ | ○ |
| | 33 | | D-1:0.4, D-3:0.4 | | ○ | ○ | ○ |
| | 34 | | D-5:0.8 | | ○ | ○ | ○ |
| | 35 | | D-1:1.6, D-3:8.4 | | ○ | ○ | ○ |
| | 36 | | D-1:8.4, D-3:1.6 | | ○ | ○ | ○ |
| | 37 | | D-1:1, D-5:9 | | ○ | ○ | ○ |
| | 38 | | D-1:6, D-5:4 | | ○ | ○ | ○ |
| | 39 | C-1:0.06 | D-6:5, D-7:5 | B-2:2.5 | ○ | ○ | ○ |
| | 40 | C-2:0.05 | | B-10:2.5 | ○ | ○ | ○ |
| | 41 | C-3:0.05 | | B-12:2.5 | ○ | ○ | ○ |
| | 42 | C-4:0.05 | | B-13:2.5 | ○ | ○ | ○ |
| | 43 | C-5:0.05 | | | ○ | ○ | ○ |
| | 44 | C-6:0.05 | | | ○ | ○ | ○ |
| | 45 | C-7:0.05 | | | ○ | ○ | ○ |
| | 46 | C-3:0.05 C-7:0.05 | | | ○ | ○ | ○ |
| | 47 | C-2:0.05 C-5:0.05 | | | ○ | ○ | ○ |
| Comparative example | 11 | C-3:0.05 | D-1:10 | — | x | x | ○ |
| | 12 | | D-1:10 | A-1:2.5 | x | x | ○ |
| | 13 | | D-2:10 | A-1:2.5 | x | x | ○ |
| | 14 | | D-3:10 | A-1:2.5 | x | x | ○ |
| | 15 | | D-4:10 | A-1:2.5 | x | x | ○ |
| | 16 | — | — | | x | x | x |

It is clear that by using the emulsifying method in accordance with the present invention, wherein two or more kinds of higher alcohols, each having a melting point of 45° C. or more, are used, an emulsified substance of higher alcohol, which exhibits a stable emulsified state and preferably blends into skin, can be obtained without adding any surface activity.

[Preparation and Evaluation (2) of Emulsified Substances of Higher Alcohol-Emulsified Substance Containing Titanium Dioxide Microparticles]

Embodiments 48 Through 77

0.2 g of methyl p-hydroxybenzoate as an antiseptic agent was added to 115.7 g of a warm water of 80° C., 0.1 g of polysaccharide (C-3) was further added thereto, and a resultant mixture was agitated for 10 minutes while rotating a homomixer (manufactured by IKA) at 16,000 rpm, thereby dissolving the polysaccharide therein. Next, 20 g of microparticles of titanium dioxide (SMT-100WR; TAYCA Co., Ltd.) was added, and 10 g of behenyl alcohol (D-6) heated to 80° C., 10 g of the hydrogenated rapeseed oil alcohol (D-7), 5 g of dimethylpolysiloxane (A-1), 5 g of squalane (A-2), 5 g of olive oil (A-4) and 5 g of glyceryl tri-2-ethylhexanoate (A-6) as the oily component (A) were mixed while agitating the homomixer (manufactured by IKA) at 16,000 rpm., and 4 g of the chimyl alcohol (B-1) as the oily component (B) was added and agitated for five minutes for emulsification. Next, by decreasing the agitating rate to 13,000 rpm, cooling the mixture to 40° C. with a cold water in 10 minutes, and further cooling the mixture to 25° C. with an ice cold water in 5 minutes, an emulsified substance of higher alcohol, which contains microparticles of titanium dioxide of Embodiment 48, was obtained. Similarly, by replacing chimyl alcohol (B-1) as the oily component (B) with various substances, emulsified substances of higher alcohols of Embodiments 49 trough 77 were obtained.

Comparative Example 17

0.2 g of methyl p-hydroxybenzoate as an antiseptic agent was added to 139.7 g of a warm water of 80° C., 0.1 g of polysaccharide (C-3) was further added thereto, and a resultant mixture was agitated for 10 minutes while rotating a homomixer (manufactured by IKA) at 16,000 rpm, thereby dissolving the polysaccharide therein. Next, 20 g of microparticles of titanium dioxide (SMT-100WR; TAYCA Co., Ltd.) was added, and 10 g of behenyl alcohol (D-6) heated to 80° C., and 10 g of hydrogenated rapeseed oil alcohol (D-7) were mixed while agitating the homomixer (manufactured by IKA) at 16,000 rpm, and agitated for five minutes for emulsification. Next, by decreasing the agitating rate to 13,000 rpm, cooling the mixture to 40° C. with a cold water in 10 minutes, and further cooling the mixture to 25° C. with an ice cold water in 5 minutes, an emulsified substance of higher alcohol, which contains microparticles of titanium dioxide of Comparative example 6 was obtained.

Comparative Example 18

0.2 g of methyl p-hydroxybenzoate as an antiseptic agent was added to 139.7 g of a warm water of 80° C., 0.1 g of polysaccharide (C-3) was further added thereto, and a resultant mixture was agitated for 10 minutes while rotating a homomixer (manufactured by IKA) at 16,000 rpm, thereby dissolving the polysaccharide therein. Next, 20 g of microparticles of titanium dioxide (SMT-100WR; TAYCA Co., Ltd.) was added, and 10 g of behenyl alcohol (D-6) heated to 80° C., 10 g of hydrogenated rapeseed oil alcohol (D-7) were mixed while agitating the homomixer (manufactured by IKA) at 16,000 rpm, and 4 g of the chimyl alcohol (B-1) as the oily component (B) was added and agitated for five minutes for emulsification. Next, by decreasing the agitating rate to 13,000 rpm, cooling the mixture to 40° C. with a cold water in 10 minutes, and further cooling the mixture to 25° C. with an ice cold water in 5 minutes, an emulsified substance, which contains microparticles of titanium dioxide of Comparative example 18 was obtained.

Comparative Example 19

0.2 g of methyl p-hydroxybenzoate as an antiseptic agent was added to 139.7 g of a warm water of 80° C., 0.1 g of polysaccharide (C-3) was further added thereto, and a resultant mixture was agitated for 10 minutes while rotating a homomixer (manufactured by IKA) at 16,000 rpm, thereby dissolving the polysaccharide. Next, 20 g of microparticles of titanium dioxide (SMT-100WR; TAYCA Co., Ltd.) was added, and 10 g of behenyl alcohol (D-6) heated to 80° C., 10 g of hydrogenated rapeseed oil alcohol (D-7), 5 g of dimethylpolysiloxane (A-1), 5 g of squalane (A-2), 5 g of olive oil (A-4) and 5 g of glyceryl tri-2-ethylhexanoate (A-6) as the oily component (A) were mixed and agitated for five minutes for emulsification. Next, by decreasing the agitating rate to 13,000 rpm, cooling the mixture to 40° C. with a cold water in 10 minutes, and further cooling the mixture to 25° C. with an ice cold water in 5 minutes, an emulsified substance of Comparative example 18 was obtained.

(Sensory Test of Emulsified Substances of Higher Alcohols, Each Containing Microparticles of Titanium Dioxide)

Obtained emulsified substances of higher alcohols, each containing microparticles of titanium dioxide, were applied to skin, and sensory tests of skin feel were performed. And they were evaluated as follows:

○: well blending into skin x: not well blending into skin, water repelling or oil repelling occurred on skin with repelling feel.

Further, in order to evaluate the stability of the emulsified substances by visual observation, 50 g of emulsified substances were put in glass vessels, sealed, and placed in a thermostatic chamber with a cycle of –10° C. (24 hours) to 50° C. (24 hours). And evaluation was performed such that ○: an emulsified state is maintained.

x: oil contents float on surface, or emulsification phases separate as an upper part, and separation between a water phase and an oil phase is observed. The evaluation results are shown in Table 9

TABLE 9

| Example | No | Higher alcohol | Oily component (A) | Oily component (B) | Stability 1 week | 1 month | Feel |
|---|---|---|---|---|---|---|---|
| Embodiment | 48 | D-6:5 | A-1:2.5 | B-1:4 | ○ | ○ | ○ |
| | 49 | D-7:5 | A-2:2.5 | B-2:4 | ○ | ○ | ○ |
| | 50 | | A-5:2.5 | B-3:4 | ○ | ○ | ○ |
| | 51 | | A-6:2.5 | B-4:4 | ○ | ○ | ○ |
| | 52 | | | B-5:4 | ○ | ○ | ○ |
| | 53 | | | B-6:4 | ○ | ○ | ○ |
| | 54 | | | B-7:4 | ○ | ○ | ○ |
| | 55 | | | B-8:4 | ○ | ○ | ○ |
| | 56 | | | B-9:4 | ○ | ○ | ○ |
| | 57 | | | B-10:4 | ○ | ○ | ○ |
| | 58 | | | B-11:4 | ○ | ○ | ○ |
| | 59 | | | B-12:4 | ○ | ○ | ○ |

TABLE 9-continued

| Example | No | Higher alcohol | Oily component (A) | Oily component (B) | 1 week | 1 month | Feel |
|---|---|---|---|---|---|---|---|
| | 60 | | | B-13:4 | ○ | ○ | ○ |
| | 61 | | | B-1:2, B-3:2 | ○ | ○ | ○ |
| | 62 | | | B-2:2, B-13:2 | ○ | ○ | ○ |
| | 63 | | | B-2:2, B-12:2 | ○ | ○ | ○ |
| | 64 | | | B-13:2, B-7:2 | ○ | ○ | ○ |
| | 65 | | | B-13:2, B-8:2 | ○ | ○ | ○ |
| | 66 | | | B-13:2, B-10:2 | ○ | ○ | ○ |
| | 67 | | | B-2:2, B-10:2 | ○ | ○ | ○ |
| | 68 | | | B-2:2, B-8:2 | ○ | ○ | ○ |
| | 69 | | | B-1:1, B-13:1, B-12:2 | ○ | ○ | ○ |
| | 70 | | | B-7:1, B-10-1 | ○ | ○ | ○ |
| | 71 | | | B-2:1, B-13:1, B-12:1, B-10:1 | ○ | ○ | ○ |
| | 72 | | | B-13:1, B-12:1 B-7:1, B-8:1 | ○ | ○ | ○ |
| | 73 | | | B-7:0.5, B-8:0.5 | ○ | ○ | ○ |
| | 74 | | | B-12:0.5, B-10:0.5 | ○ | ○ | ○ |
| | 75 | | | B-8:0.5, B-10:0.5 | ○ | ○ | ○ |
| | 76 | | | B-13:0.5, B-12:0.5, B-10:0.5 | ○ | ○ | ○ |
| | 77 | | | B-13:0.5, B-12:0.5, B-10:0.5, B-7:0.45, B-8:0.05 | ○ | ○ | ○ |
| Comparative Example | 17 | | | — | x | x | ○ |
| | 18 | D-6:5 | — | B-1:4 | ○ | x | ○ |
| | 19 | D-7:5 | — | — | ○ | x | ○ |
| | | | A-1:5 A-2:5 A-4:5 A-6:5 | | | | |

It is clear that by using the emulsifying method in accordance with the present invention, an emulsified substance of higher alcohol, which contains titanium dioxide that is difficult to be emulsified and dispersed, can be obtained without adding any surface activity. Furthermore, it is clear that an emulsified substance well blending into skin can be obtained.

[Preparation and Evaluation (3) of Emulsified Substances of Higher Alcohols]

Embodiments 78 Through 84

0.2 g of methyl p-hydroxybenzoate as an antiseptic agent was added to 129.7 g to 184.7 g of a warm water of 80° C., 0.1 g (or 0.2 g) of polysaccharide (C-3) was further added, and a resultant mixture was agitated for 10 minutes while rotating a homomixer (manufactured by IKA) at 16,000 rpm, thereby dissolving the polysaccharide therein. Next, 5 g of an equivalent mixture of cetostearyl alcohol (D-5) and behenyl alcohol (D-6), 10 g (otherwise, 25 or 40 g) of an equivalent mixture of 9 g of dimethylpolysiloxane (A-1) and 5 g of bees wax (B-13) as the oily component were added and agitated for five minutes for emulsification. Next, by decreasing the agitating rate to 13,000 rpm, cooling the mixture to 40° C. with a cold water in 10 minutes, and further cooling the mixture to 25° C. with an ice cold water in 5 minutes, emulsified substances of higher alcohols of Embodiments 78 through 80 were obtained. Similarly, emulsified substances of higher alcohols of Embodiments 81 trough 84 were obtained by determining the amount of the equivalent mixture of cetostearyl alcohol and behenyl alcohol to 15 g and 25 g, and determining the amount of the mixture of the oily components (A-1) and (B-13) in the ratio of 9:1, to 10 g, 25 g, 40 g, Comparative Examples 20 Through 22

0.2 g of methyl p-hydroxybenzoate as an antiseptic agent was added to 129.7 g through 184.7 g of a warm water of 80° C., 0.1 g of polysaccharide (C-3) was further added thereto, and a resultant mixture was agitated for 10 minutes while rotating a homomixer (manufactured by IKA) at 16,000 rpm, thereby dissolving the polysaccharide therein. Next, 20 g of an equivalent mixture of cetostearyl alcohol (D-5) and behenyl alcohol (D-6) and 20 g (or 30 g) of an equivalent mixture of 9 g of dimethylpolysiloxane (A-1) and 5 g of bees wax (B-13) as the oily component were added and agitated for five minutes for emulsification. Next, by decreasing the agitating rate to 13,000 rpm, cooling the mixture to 40° C. with a cold water in 10 minutes, and further cooling the mixture to 25° C. with an ice cold water in 5 minutes, emulsified substances of higher alcohol of Comparative examples 20 through 22 were obtained.

(Sensory Test of Emulsified Substances of Higher Alcohols)

Obtained emulsified substances of higher alcohols were applied to skin, and sensory tests of feel for skin were performed. And they were evaluated as follows:
 ○: well blending into skin
 x: not well blending into skin, repelling occurred on skin
Further, in order to evaluate the stability of the emulsified substances by visual observation, 50 g of emulsified substances were put in glass vessels, sealed, and placed in a thermostatic chamber with a cycle of −10° C. (24 hours) to 50° C. (24 hours). And evaluation was performed such that
 ○: an emulsified state is maintained.
 x: oil contents float on surface, or emulsification phases separate as an upper part, and separation between a water phase and an oil phase is observed. The evaluation results are shown in Table 10.

TABLE 10

| Example | No. | Content of polysaccharide (wt %) | Content of higher alcohol (wt %) | Content of oily component (wt %) | Stability (3 months) | Feel |
|---|---|---|---|---|---|---|
| Embodiment | 78 | C-1:0.05 | D-5:2.5, D-6:2.5 | 10 | ○ | ○ |
|  | 79 | C-1:0.05 | D-5:2.5, D-6:2.5 | 20 | ○ | ○ |
|  | 80 | C-1:0.05 | D-5:2.5, D-6:2.5 | 40 | ○ | ○ |
|  | 81 | C-1:0.05 | D-5:5, D-6:5 | 40 | ○ | ○ |
|  | 82 | C-1:0.05 | D-5:10, D-6:10 | 40 | ○ | ○ |
|  | 83 | C-1:0.1 | D-5:10, D-6:10 | 20 | ○ | ○ |
|  | 84 | C-1:0.1 | D-5:10, D-6:10 | 40 | ○ | ○ |
| Comparative example | 20 | C-1:0.05 | D-5:10, D-6:10 | 0 | x | ○ |
|  | 21 | C-1:0.05 | D-5:15, D-6:15 | 20 | x | ○ |
|  | 22 | C-1:0.05 | D-5:15, D-6:15 | 20 | x | ○ |

By using the emulsifying method in accordance with the present invention, not only a stable emulsified state but also an emulsification well blending into skin are obtained without adding any surface activity

[Preparation and Evaluation of Cosmetics]

Embodiment 85

Milky Lotion 1

The composition of the milky lotion 1 will be shown in Table 11.

TABLE 11

| Section | Components (trade name, maker) | % by weight |
|---|---|---|
| a | glycerin (glycerin S, Sakamoto Yakuhin Kogyo Co., Ltd.) | 5.00 |
|  | diglycerin (diglycerin 801, Sakamoto Yakuhin Kogyo Co., Ltd.) | 2.00 |
|  | 1,3-buthyleneglycol (1,3BG, DAICEL CHEMICAL INDUSTRIES, LTD.) | 7.00 |
|  | 1-(2-ethyl hexyl)glycol ether (sencibaSC50, SEIWA KASEI Co., Ltd.) | 0.30 |
|  | 1,2-Pentandiol (diolPD, Nikko Chemicals Co., Ltd.) | 3.00 |
|  | POE methyl glucoside (MagbioburaidoMG-20E, NOF CORPORATION) | 0.50 |
| b | behenyll alcohol (D-6) | 2.00 |
|  | hydrogenated rapeseed oil alcohol (D-7) | 2.00 |
|  | dimethyl polysiloxane (A-1) | 2.00 |
|  | squalane (A-2) | 2.00 |
|  | olive oil (A-4) | 2.00 |
|  | bees wax (B-13) | 2.00 |
|  | glyceryl tri-2-ethylhexanoate (A-6) | 2.00 |
|  | natural vitamin E (Riken oil E700, Riken Vitamin co., Ltd.) | 0.01 |
| c | polysaccharide (C-3) | 0.05 |
|  | purified water | balance |

1. Polysaccharide (C-3) of Section c was heated to 80° C., and pre-dispersed in purified water using a disperser (Dispersion liquid 1).

2. Components of Section a were respectively weighed, mixed with the dispersion liquid 1 homogeneously, and dissolved by heating at 80° C. (Dispersion liquid 2).

3. Components of Section b were respectively weighed, and dissolved by heating at 80° C. (Mixture liquid 1)

4. The mixture liquid 1 was added to the dispersion liquid 2 while agitating with a homogenizer (or homomixer) at 8000 rpm. After added, a resultant mixture was further agitated for 10 minutes, and cooled to room temperature, whereby milky lotion 1 (Embodiment 85) was obtained.

Embodiment 86

Milky Lotion 2

By replacing behenyl alcohol (D-6) of Section b of Embodiment 85 with the same amount of hexadecanol (D-1), and replacing hydrogenated rapeseed oil alcohol (D-7) with the same amount of octadecanol (D-2), milky lotion 2 (Embodiment 86) was obtained.

Embodiment 87

Milky Lotion 3

By replacing behenyl alcohol (D-6) of Section b of Embodiment 85 with the same amount of cetostearyl alcohol (D-5), and replacing hydrogenated rapeseed oil alcohol (D-7) with the same amount of docosanol (D-4), milky lotion 3 (Embodiment 87) was obtained.

Embodiment 88

Milky Lotion 4

By replacing behenyl alcohol (D-6) of Section b of Embodiment 85 with a half amount of hexadecanol (D-1) and a half amount of octadecanol (D-2), and replacing hydrogenated rapeseed oil alcohol (D-7) with a half amount of eicosanol (D-3) and a half amount of docosanol (D-4), milky lotion 4 (Embodiment 87) was obtained.

Embodiment 89

Milky Lotion 5

The composition of the milky lotion 5 will be shown in Table 12. By preparing, similarly to Embodiment 66: milky lotion 1, milky lotion 5 (Embodiment 89) was obtained.

TABLE 12

| Section | Components (trade name, maker) | % by weight |
|---|---|---|
| a | glycerin (glycerin S, Sakamoto Yakuhin Kogyo Co., Ltd.) | 5.000 |
|   | diglycerin (diglycerin 801, Sakamoto Yakuhin Kogyo Co., Ltd.) | 2.000 |
|   | 1,3-buthyleneglycol (1,3BG, DAICEL CHEMICAL INDUSTRIES, LTD.) | 7.000 |
|   | 1-(2-ethyl hexyl)glycol ether (sencibaSC50, SEIWA KASEI Co., Ltd.) | 0.300 |
|   | 1,2-Pentandiol (diolPD, Nikko Chemicals Co., Ltd.) | 3.000 |
|   | Trehalose glucoside (Tornare HAYASHIBARA BIOCHEMICAL LABS., INC.) | 0.500 |
| b | behenyll alcohol (D-6) | 2.000 |
|   | hydrogenated rapeseed oil alcohol (D-7) | 2.000 |
|   | dimethyl polysiloxane (A-1) | 2.000 |
|   | Olive oil (A-4) | 2.000 |
|   | Bees wax (B-13) | 0.500 |
|   | hydroxystearic acid cholesteryl (B-3) | 2.000 |
|   | batyl alcohol (B-2) | 0.500 |
|   | jojoba seed oil (jojoba oil) (A-9) | 2.000 |
|   | glyceryl tri-2-ethylhexanoate (A-6) | 2.000 |
|   | natural vitamin E (Riken oil E700, Riken Vitamin co., Ltd.) | 0.010 |
| c | polysaccharide (C-3) | 0.045 |
|   | purified water | balance |

Embodiment 90

Milky Lotion 6

By replacing olive oil (A-4) of Section b of Embodiment 89 with the same amount of liquid paraffin (A-5), replacing glyceryl tri-2-ethylhexanoate (A-6) with the same amount of di(cholesteryl/octyldodecyl)lauroyl glutamate (B-5), and replacing batyl alcohol (B-2) with the same amount of chimyl alcohol (B-1), milky lotion 6 (Embodiment 90) was obtained.

Embodiment 91

Milky Lotion 7

By replacing olive oil (A-4) of Section b of Embodiment 89 with the same amount of phytosteryl oleate (B-6), replacing glyceryl tri-2-ethylhexanoate (A-6) with the same amount of di(cholesteryl/behenyl/octyidodecyl)lauroyl glutamate (B-4), and replacing batyl alcohol (B-2) with the same amount of di(cholesteryl/octyldodecyl)lauroyl glutamate (B-5), milky lotion 7 (Embodiment 91) was obtained.

Embodiment 92

Milky Lotion 8

By replacing olive oil (A-4) of Section b of Embodiment 89 with the same amount of dipentaerythrityl hexylhydroxystearate/hexastearate/hexarosinate (B-9), replacing hydroxystearic acid cholesteryl (B-3) with the same amount of dipentaerythrityl hexylhydroxystearate (B-10), and replacing batyl alcohol (B-2) with the same amount of glycerye ethylhexanoate/stearate/adipate (B-11), milky lotion 8 (Embodiment 92) was obtained.

Embodiment 93

Milky Lotion 9

By replacing olive oil (A-4) of Section b of Embodiment 89 with the same amount of caprylic/caproc acid triglyceryl (A-7), and replacing hydroxystearic acid cholesteryl (B-3) with the same amount of dipentaerythrityl hexylydroxystearate (B-10), milky lotion 9 (Embodiment 93) was obtained.

Embodiment 94

Milky Lotion 10

The composition of the milky lotion 10 will be shown in Table 13.

TABLE 13

| Section | Components (trade name, maker) | % by weight |
|---|---|---|
| a | glycerin (glycerin S, Sakamoto Yakuhin Kogyo Co., Ltd.) | 5.00 |
|   | xylitol (xylitol, Kanto Chemical Co., Inc.) | 1.00 |
|   | 1,3-buthyleneglycol (1,3BG, DAICEL CHEMICAL INDUSTRIES, LTD.) | 8.00 |
|   | Esters of p-hydroxybenzoic acid (, UENO FINE CHEMICALS INDUSTRY) | 0.10 |
| b | behenyll alcohol (D-6) | 4.00 |
|   | dimethyl polysiloxane (A-1) | 2.00 |
|   | liquid paraffin (A-5) | 2.00 |
|   | bees wax (B-13) | 0.50 |
|   | dipentaerythrityl hexalydroxystearate (B-10) | 2.00 |
|   | batyl alcohol (B-2) | 0.50 |
|   | isostearyl myristate (A-8) | 2.00 |
|   | caprylic/caproc acid triglyceryl (A-7) | 2.00 |
|   | natural vitamin E (Riken oil E700, Riken Vitamin co., Ltd.) | 0.01 |
| c | polysaccharide (C-3) | 0.06 |
|   | purified water | balance |
| d | carboxyvinylpolymer (HIVISWAKO105, Wako Pure Chemical Industries, Ltd.) | 0.05 |
| e | purified water | 2.45 |
|   | L-Arginine (l-Arginine, AJINOMONOT CO., INC.) | 0.05 |

1. Polysaccharide (C-3) of Section c was heated to 80° C., and pre-dispersed in water using a disperser (Dispersion liquid 1).
2. Components of Section a were respectively weighed, mixed with the dispersion liquid 1 homogeneously and dissolved by heating to 80° C. (Dispersion liquid 2).
3. Components of Section b were respectively weighed, and dissolved by heating at 80° C. (Mixture liquid 1).
4. The mixture liquid 2 was added to the dispersion liquid 2 while agitating the dispersion liquid 2 with a homogenizer (or homomixer) at 8000 rpm (Dispersion liquid 3).
5. HIVISWAKO105 was pre-dispersed in water by using a disperser (Dispersion liquid 4).
6. The dispersion liquid 4 was added to the dispersion liquid 3 and mixed therewith homogeneously (Dispersion liquid 5).
7. Components of Section e were dispersed homogeneously (Dispersion liquid 6).
8. The dispersion liquid 6 was added to the dispersion liquid 5, after being neutralized, agitation was performed, and the cooling step to room temperature was performed, whereby milky lotion 10 (Embodiment 94) was obtained.

Embodiment 95

Milky Lotion 11

By replacing carboxy vinyl polymer of Section d of Embodiment 94 with the same amount of acylates/C-10-30 alkyl acrylate crosspolymer (Pemulen TR-1 Nikko Chemicals Co., Ltd.), milky lotion 11 (Embodiment 95) was obtained.

Comparative Example 23

Milky Lotion 12

By replacing behenyl alcohol (D-6) of Section b of Embodiment 75 with the same amount of docosanol (D-4), milky lotion 12 (Comparative example 23) was obtained.

Embodiment 96

Cream 1

The composition of cream 1 will be shown in Table 14.

TABLE 14

| Section | Components (trade name, maker) | % by weight |
|---|---|---|
| a | glycerin (glycerin S, Sakamoto Yakuhin Kogyo Co., Ltd.) | 5.00 |
|   | diglycerin (diglycerin 801, Sakamoto Yakuhin Kogyo Co., Ltd.) | 2.00 |
|   | 1,3-buthyleneglycol (1,3BG, DAICEL CHEMICAL INDUSTRIES, LTD.) | 7.00 |
|   | 1-(2-ethyl hexyl)glycol ether (sencibaSC50, SEIWA KASEI Co., Ltd.) | 0.300 |
|   | 1,2-pentandiol (diolPD, Nikko Chemicals Co., Ltd.) | 3.00 |
|   | POE methyl glucoside (MagbioburaidoMG-20E, NOF CORPORATION) | 0.50 |
| b | polysaccharide (C-3) | 0.06 |
|   | purified water | balance |
| c | behenyl alcohol (D-6) | 3.00 |
|   | hydrogenated rapeseed oil alcohol (D-7) | 2.00 |
|   | dimethyl polysiloxane (A-1) | 2.00 |
|   | squalane (A-2) | 4.00 |
|   | Jojoba oil (A-9) | 1.00 |
|   | chimyl alcohol (B-1) | 1.00 |
|   | bees wax (B-13) | 2.00 |
|   | glyceryl tri-2-ethylhexanoate (A-6) | 9.00 |
|   | dipentaerythrityl tri-polyhydroxystearate (B-10) | 4.00 |
|   | di(2-octyldodecyl)-N-lauroyl-L-glutamate (B-7) | 2.00 |
|   | di(phytosteryl•octyldodecyl•behenyl)-N-lauroyl-L-glutamate (B-8) | 0.50 |
|   | natural vitamin E (Riken oil E700, Riken Vitamin co., Ltd.) | 0.05 |
| d | carboxyvinylpolymer (HIVISWAKO104, Wako Pure Chemical Industries, Ltd.) | 0.20 |
|   | purified water | 9.80 |
|   | carboxyvinylpolymer (HIVISWAKO105, Wako Pure Chemical Industries, Ltd.) | 0.10 |
|   | purified water | 4.90 |
| e | L-Arginine (L-Arginine, AJINONOMOTO CO., INC.) | 0.30 |
|   | purified water | 2.70 |

1. Polysaccharide (C-3) of Section b was heated to 80° C., and pre-dispersed in water using a disperser (Dispersion liquid 1).
2. Components of Section a were respectively weighed, and mixed with the dispersion liquid 1 homogeneously, and dissolved by heating to 80° C. (Dispersion liquid 2).
3. Components of Section c were respectively weighed, and dissolved by heating at 80° C. (Mixture liquid 1)
4. The mixture liquid 1 was gradually added to the dispersion liquid 2 while agitating the dispersion liquid 2 with a homogenizer (or homomixer) at 8000 rpm (Dispersion liquid 3).
5. After added, the agitating operation was performed for 10 minutes.
6. HIVISWAKO 104, 105 of Section d were pre-dispersed in water by using a disperser (Dispersion liquid 4).
7. Components of Section e were respectively dispersed homogeneously (Dispersion liquid 5).
8. The dispersion liquid 4 was added to the dispersion liquid 3, and mixed therewith homogeneously (Dispersion liquid 6).
9. The dispersion liquid 5 was added to the dispersion liquid 6, and after being neutralized, cooling operation to room temperature was performed, whereby cream 1 (Embodiment 96) was obtained.

Embodiment 97

Cream 2

By replacing carboxyvinyl polymer (HIVISWAKO 104, 105) of Section d of Embodiment 96 with the same amount of hydroxypropylmethylcellulose stearoxy ether (SANGELOSE90L: manufactured by Daido Chemical Corporation), cream 2 (Embodiment 97) was obtained.

Embodiment 98

Cream 3

By replacing carboxyvinyl polymer (HIVISWAKO 104, 105) of Section d of Embodiment 96 with the same amount of starch-sodium acrylic acid graft copolymer (SANFRESH ST-500D: manufactured by Sanyo Chemical Industries, Ltd), cream 3 (Embodiment 97) was obtained.

Embodiment 99

Cream 4

By replacing carboxyvinyl polymer (HIVISWAKO 104, 105) of Section d of Embodiment 96 with the same amount of cellulose crystals (RC-591S: manufactured by Asahi Kasei Corporation), cream 4 (Embodiment 99) was obtained.

Embodiment 100

Cream 5

The composition of cream 5 will be shown in Table 15.

TABLE 15

| Section | Components (trade name, maker) | % by weight |
|---|---|---|
| a | purified hydrogenated Lecithin (Lecithinol, Sakamoto Nikko Chemicals Co., Ltd.) | 0.20 |
|   | glycerin (glycerin S, Sakamoto Yakuhin Kogyo Co., Ltd.) | 5.00 |
|   | diglycerin (diglycerin 801, Sakamoto Yakuhin Kogyo Co., Ltd.) | 2.00 |
|   | 1,3-buthyleneglycol (1,3BG, DAICEL CHEMICAL INDUSTRIES, LTD.) | 7.00 |
|   | 1-(2-ethyl hexyl)glycol ether (sencibaSC50, SEIWA KASEI Co., Ltd.) | 0.300 |
|   | 1,2-pentandiol (diolPD, Nikko Chemicals Co., Ltd.) | 3.00 |
|   | POE methyl glucoside (MagbioburaidoMG-20E, NOF CORPORATION) | 0.50 |
| b | polysaccharide (C-3) | 0.06 |
|   | purified water | balance |
| c | behenyl alcohol (D-6) | 3.00 |
|   | hydrogenated rapeseed oil alcohol (D-7) | 2.00 |
|   | dimethyl polysiloxane (A-1) | 2.00 |
|   | squalane (A-2) | 4.00 |
|   | Jojoba oil (A-9) | 1.00 |
|   | chimyl alcohol (B-1) | 1.00 |
|   | bees wax (B-13) | 2.00 |
|   | glyceryl tri-2-ethylhexanoate (A-4) | 9.00 |
|   | dipentaerythrityl tri-polyhydroxystearate (B-10) | 4.00 |

TABLE 15-continued

| Section | Components (trade name, maker) | % by weight |
| --- | --- | --- |
| | di(2-octyldodecyl)-N-lauroyl-L-glutamate (B-7) | 2.00 |
| | di(phytosteryl•octyldodecyl•behenyl)-N-lauroyl-L-glutamate (B-8) | 0.50 |
| | natural vitamin E (Riken oil E700, Riken Vitamin co., Ltd.) | 0.05 |

1. Polysaccharide (C-3) of Section b was heated to 80° C., and pre-dispersed in water using a disperser (Dispersion liquid 1).

2. Components of Section a were respectively weighed, and mixed with the dispersion liquid 1 homogeneously, and dissolved by heating to 80° C. (Dispersion liquid 2).

3. Components of Section c were respectively weighed, and dissolved by heating at 80° C. (Mixture liquid 1)

4. The dispersion liquid 2 was gradually added to the mixture liquid 1 while agitating the mixture liquid 1 with a homogenizer (or homomixer) at 8000 rpm. After added, the agitating operation was performed for 10 minutes and the cooling operation to room temperature was performed, whereby cream 5 (Embodiment 100) was obtained.

Embodiment 101

Cream 6

The composition of cream 6 will be shown in Table 16.

TABLE 16

| Section | Components (trade name, maker) | % by weight |
| --- | --- | --- |
| a | polysaccharide (C-3) | 0.064 |
| | purified water | 32.806 |
| b | glycerin (glycerin S, Sakamoto Yakuhin Kogyo Co., Ltd.) | 5.000 |
| | diglycerin (diglycerin 801, Sakamoto Yakuhin Kogyo Co., Ltd.) | 2.000 |
| | 1,3-buthyleneglycol (1,3BG, DAICEL CHEMICAL INDUSTRIES, LTD.) | 7.000 |
| | 1-(2-ethyl hexyl) glycol ether (sencibaSC50, SEIWA KASEI Co., Ltd.) | 0.300 |
| | 1,2-pentandiol (diolPD, Nikko Chemicals Co., Ltd.) | 3.000 |
| | purified water | balance |
| c | Behenyl alcohol (D-6) | 6.000 |
| | dimethyl polysiloxane (A-1) | 2.000 |
| | squalane (A-2) | 4.000 |
| | olive oil (A-4) | 1.000 |
| | Phytosteryl oleate (B-6) | 4.000 |
| | batyl alcohol (B-2) | 0.50 |
| | caprylic/capric triglyceride (A-7) | 2.000 |
| | glyceryl tri-2-ethylhexanoate (A-6) | 8.000 |
| | natural vitamin E (Riken oil E700, Riken Vitamin co., Ltd.) | 0.030 |
| | polyglyceryl monostearate (DECAGREEN, NIHONSURFACTANT KOGYO K.K.) | 0.500 |
| d | carboxyvinylpolymer (HIVISWAKO104, Wako Pure Chemical Industries, Ltd.) | 0.200 |
| | 1,3-buthyleneglycol (1,3BG, DAICEL CHEMICAL INDUSTRIES, LTD.) | 2.000 |
| | purified water | 7.800 |
| e | acylates/C-10-30 alkyl acrylate crosspolymer (Pemulen TR-2 Nikko Chemicals) | 0.080 |
| | 1,3-buthyleneglycol (1,3BG, DAICEL CHEMICAL INDUSTRIES) | 0.800 |
| | purified water | 3.120 |
| f | dipotassium glycyrrhizinate (GLYTIONON K2, TOKIWA PHYTOCHEMICAL CO., LTD.) | 0.100 |
| | purified water | 5.000 |
| g | L-Arginine (L-Arginine, AJINOMOTO CO., INC.) | 0.600 |
| | purified water | 5.400 |

TABLE 16-continued

| Section | Components (trade name, maker) | % by weight |
| --- | --- | --- |
| h | L-Ascorbic acid 2-glucoside (AS-G, HAYASHIBARA BIOCHEMICAL LABS., INC.) | 2.000 |
| | triethanolamine | 1.000 |
| | purified water | 10.000 |

1. Polysaccharide (C-3) of Section b was heated to 80° C., and pre-dispersed in water using a disperser (Dispersion liquid 1).

2. Components of Section b were respectively weighed, and dissolved by heating at 70° C. (Mixture liquid 2).

3. Components of Section c were respectively weighed, and dissolved by heating at 80° C. (Mixture liquid 2)

4. Components of Section d and Section e were respectively weighed, and homogeneously dissolved, and then homogeneously mixed (Mixture liquid 3)

5. The mixture liquid 1 was gradually added to the dispersion liquid 1 while agitating the mixture liquid 1 with a homogenizer (or homomixer) at 8000 rpm, and the mixture liquid 2 was gradually added at 70° C.

6. After added, the heating and agitating operation was performed for 10 minutes (Dispersion liquid 2).

7. The mixture liquid 2 was added to the dispersion liquid 2, and mixed homogeneously (Dispersion liquid 3).

8. Components of Section f, Section g, Section h were respectively weighed, and homogeneously dissolved. Then, they were added to the dispersion liquid 3, agitated and cooled to room temperature, whereby Cream 6 (Embodiment 101) was obtained.

Embodiment 102

Cream 7

By replacing behenyl alcohol (D-6) of Section c of Embodiment 77 with the same amount of octadecanol (D-2), and replacing hydrogenated rapeseed oil alcohol (D-7) with the same amount of docosanol (D-4), Cream 7 (Embodiment 102) was obtained.

Embodiment 103

Cream 8

By replacing behenyl alcohol (D-6) of Section c of Embodiment 77 with the same amount of cetostearyl alcohol (D-5), and replacing hydrogenated rapeseed oil alcohol (D-7) with the same amount of eicosanol (D-3), cream 8 (Embodiment 103) was obtained.

Comparative Example 24

Cream 9

By replacing behenyl alcohol (D-6) of Section c of Embodiment 98 with the same amount of octadecanol (D-2), and replacing hydrogenated rapeseed oil alcohol (D-7) with the same amount of octadecanol (D-2), cream 9 (Comparative example 24) was obtained.

Embodiment 104

Sunscreen 1

The composition of sunscreen 1 will be shown in Table 17.

TABLE 17

| Section | Components (trade name, maker) | % by weight |
|---|---|---|
| a | titanium dioxide (E-3) | 10.000 |
|   | silicone (Shin-etsusilicon KF96-100, Shin-Etsu Chemical Co., Ltd.) | 15.000 |
| b | hydrogenated Lecithin (LecithinolSH50, Sakamoto Nikko Chemicals Co., Ltd.) | 3.000 |
|   | 1,3-buthyleneglycol (1,3BG, DAICEL CHEMICAL INDUSTRIES, LTD.) | 15.000 |
|   | glycerin (glycerin S, Sakamoto Yakuhin Kogyo Co., Ltd.) | 15.000 |
|   | phenoxyethanol (PHENOXYETHANOL S, Lion corporation) | 0.300 |
| c | behenyl alcohol (D-6) | 1.500 |
|   | Jojoba oil (A-9) | 10.000 |
|   | hydroxystearic acid cholesteryl (B-3) | 2.000 |
|   | batyl alcohol (B-2) | 0.500 |
| d | polysaccharide (C-3) | 0.045 |
|   | purified water | balance |

1. Polysaccharide (C-3) of Section d was heated to 80° C., and pre-dispersed in water using a disperser (Dispersion liquid 1).

2. Components of Section a were respectively weighed, homogeneously mixed, and dispersed by heating at 80° C. (Dispersion liquid 2).

3. Components of Section b were respectively weighed, and homogeneously mixed, and dispersed by heating at 80° C. (Dispersion liquid 3)

4. The dispersion liquid 3 was gradually added to the dispersion liquid 2 while heating and agitating the dispersion liquid 2.

5. Components of Section c were respectively weighed, homogeneously mixed, and dispersed by heating at 80° C. (Dispersion liquid 5).

6. The dispersion liquid 5 was gradually added to the dispersion liquid 1 while agitating the dispersion liquid 1 with a homogenizer (or homomixer) at 8000 rpm. Then, the dispersion liquid 4 was also added gradually.

5. After added, the mixture liquid 2 was gradually added at 70° C.

6. After added, the agitating operation was performed for 10 minutes, and cooling operation to room temperature was performed, where sunscreen 1 (Embodiment 104) was obtained.

Embodiment 105

Sunscreen 2

The composition of sunscreen 2 will be shown in Table 18.

TABLE 18

| Section | Components (trade name, maker) | % by weight |
|---|---|---|
| a | glycerin (glycerin S, Sakamoto Yakuhin Kogyo Co., Ltd.) | 5.000 |
|   | 1,3-buthyleneglycol (1,3BG, DAICEL CHEMICAL INDUSTRIES, LTD.) | 7.000 |
|   | 1-(2-ethyl hexyl)glycol ether (sencibaSC50, SEIWA KASEI Co., Ltd.) | 0.300 |
|   | 1,2-pentandiol (diolPD, Nikko Chemicals Co., Ltd.) | 3.000 |
|   | titanium dioxide (SMT-100WR, TAYCA CORPORATION) | 7,000 |
| b | behenyll alcohol (D-6) | 4.000 |
|   | dimethyl polysiloxane (A-1) | 2.000 |
|   | Grape seed oil (A-3) | 8.000 |
|   | Squalane (A-2) | 0.500 |
|   | hydroxystearic acid cholesteryl (B-3) | 2.000 |
|   | batyl alcohol (B-2) | 0.500 |
|   | bees wax (B-13) | 2.000 |
|   | glyceryl tri-2-ethylhexanoate (A-6) | 2.000 |
|   | natural vitamin E (Riken oil E700, Riken Vitamin co., Ltd.) | 0.010 |
| c | polysaccharide (C-3) | 0.045 |
|   | purified water | balance |

1. Polysaccharide (C-3) of Section c was heated to 80° C., and pre-dispersed in water using a disperser (Dispersion liquid 1).

2. Components of Section a were respectively weighed, and homogeneously mixed with the dispersion liquid 1, and dispersed by heating at 80° C. (Dispersion liquid 2).

3. Components of Section c were respectively weighed, and dispersed by heating at 80° C. (Mixture liquid 1)

4. The mixture liquid 1 was gradually added to the dispersion liquid 2 while agitating the dispersion liquid 2 with a homogenizer (or homomixer) at 8000 rpm. After added, the agitating operation was performed for 10 minutes, and cooling operation to room temperature was performed, where sunscreen 2 (Embodiment 105) was obtained.

Comparative Example 25

Sunscreen 3

By replacing behenyl alcohol (D-6) of Section b of Embodiment 105 with the same amount of octadecanol (D-2), sunscreen 3 (Comparative example 25) was obtained.

[Stability Test of Cosmetic]

After preparing the cosmetics of Embodiments 85 through 105 and Comparative examples 23 through 25, 100 ml of each cosmetic was put in a graduated cylinder with a ground-in steeper, sealed, and placed in a thermostatic chamber at 45° C. After 12 weeks, the separation in the cosmetic within the graduated cylinder was measured by visual observation. The results were shown in Table 19 according to the following evaluation criteria. All embodiments show good results.

(Evaluation Criteria of Stability)

○: no separation nor precipitation is observed visually; and
x: separation and precipitation are observed visually

[Sensory Test of Cosmetic (Evaluation of Feeling upon Using)]

The cosmetics (Embodiments 85 through 105 and Comparative examples 23 through 25) just after preparation, and the cosmetics (Embodiments 20 through 45 and Comparative examples 11 through 14) placed in the thermostatic chamber at 45° C. continuously for 12 weeks were respectively subdivided in ten sets of vessels, each having an identical external appearance to each other, such that they cannot be distinguished from each other. Two panelers in every ages from teens to fifties, ten panelers in total, were selected, a proper amount of each of the cosmetic was taken with fingers, spread on backs of both hands of each paneler, and "smoothness" thereof was respectively evaluated. The evaluation criteria of "smoothness" were determined as follows. The results were shown in Table 19. All embodiments show good results.

(Evaluation Criteria of "Smoothness")

○: evaluated by eight or more out of ten panelers to have smooth feel

X: evaluated by seven or less out of ten panelers to have smooth feel

TABLE 19

| Example | Cosmetic | Separation and precipitation | Smoothness Just after preparation | After 12 weeks |
|---|---|---|---|---|
| Embodiment 85 | milky lotion 1 | ○ | ○ | ○ |
| Embodiment 86 | milky lotion 2 | ○ | ○ | ○ |
| Embodiment 87 | milky lotion 3 | ○ | ○ | ○ |
| Embodiment 88 | milky lotion 4 | ○ | ○ | ○ |
| Embodiment 89 | milky lotion 5 | ○ | ○ | ○ |
| Embodiment 100 | milky lotion 6 | ○ | ○ | ○ |
| Embodiment 101 | milky lotion 7 | ○ | ○ | ○ |
| Embodiment 102 | milky lotion 8 | ○ | ○ | ○ |
| Embodiment 103 | milky lotion 9 | ○ | ○ | ○ |
| Embodiment 104 | milky lotion 10 | ○ | ○ | ○ |
| Embodiment 105 | milky lotion 11 | ○ | ○ | ○ |
| Embodiment 106 | cream 1 | ○ | ○ | ○ |
| Embodiment 107 | cream 2 | ○ | ○ | ○ |
| Embodiment 108 | cream 3 | ○ | ○ | ○ |
| Embodiment 109 | cream 4 | ○ | ○ | ○ |
| Embodiment 100 | cream 5 | ○ | ○ | ○ |
| Embodiment 101 | cream 6 | ○ | ○ | ○ |
| Embodiment 102 | cream 7 | ○ | ○ | ○ |
| Embodiment 103 | cream 8 | ○ | ○ | ○ |
| Embodiment 104 | sunscreen 1 | ○ | ○ | ○ |
| Embodiment 105 | sunscreen 2 | ○ | ○ | ○ |
| Compartive example 23 | milky lotion 12 | x | ○ | x |
| Compartive example 24 | cream 9 | x | ○ | x |
| Compartive example 25 | sunscreen 3 | x | ○ | x |

○: evaluated by eight or more out of ten panelers to have smooth feel
x: evaluated by seven or less out of ten panelers to have smooth feel

The invention claimed is:

1. A cosmetic in an emulsified state, said cosmetic comprising:
a higher alcohol, an oily component other than the higher alcohol, and polysaccharide in an emulsified state,
wherein the higher alcohol comprises two or more kinds of higher alcohols, each having a melting point of 45° C. or more, in an amount of 1% by weight to 20% by weight relative to a total amount of the cosmetic,
wherein the oily component is contained in an amount of 1% by weight to 20% by weight relative to the total amount of the cosmetic,
wherein the polysaccharide comprises at least one of fucose, glucose, glucuronic acid and rhamnose as a constituent monosaccharide, and comprises fucose and/or rhamnose in a side chain in an amount of 0.01% by weight to 1% by weight relative to the total amount of the cosmetic,
wherein a mixing ratio of two or more kinds of higher alcohols, as said higher alcohol, is such that a mixing ratio of a higher alcohol of which the content is a maximum and a higher alcohol of which the content is a minimum ranges from 1:1 to 5:1,
wherein said higher alcohol comprises two or more kinds of higher alcohols selected from hexadecanol, octadecanol, eicosanol and docosanol, each of the selected two or more kinds of higher alcohols is contained in an amount of 0.4% by weight or more relative to the total amount of the cosmetic, and a total of the selected two or more kinds of higher alcohols is contained in an amount of 0.8% by weight to 20% by weight relative to the total amount of the cosmetic,
wherein said polysaccharide comprises at least a polysaccharide represented by the following general formula (1)

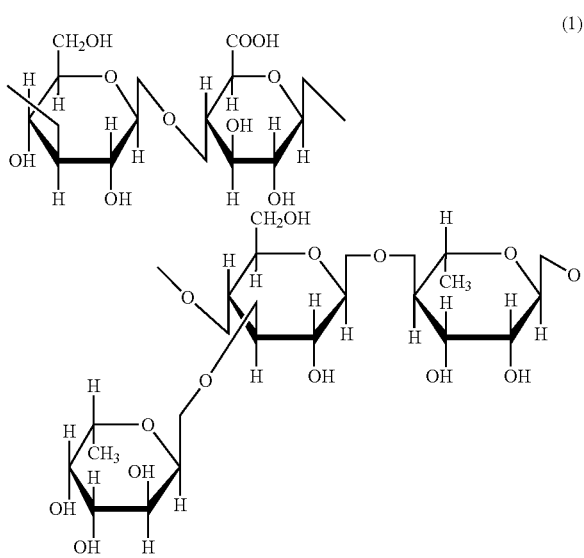

wherein said oily component comprises:
an oily component (A) comprising at least one member selected from a group consisting of dimethyl polysiloxan, trimethyl polysiloxan, squalane, paraffin, isopropyl palmitate, myristyl myristate, isostearyl myristate, glyceryl triethylhexanoate, glyceryl tricaplyrate tricaprate, grape seed oil, rosa canina fruit oil, sunflower oil, olive fruit oil, avocado oil, macadamia ternifolia seed oil, meadowfoam seed oil, shea oil and jojoba seed oil; and
an oily component (B) comprising at least one member selected from a group consisting of beeswax, hydrogenated jojoba oil, chimyl alcohol, batyl alcohol, cholesterol, cholesteryl stearate, phytosterol, glyceryl trimyristate and glyceryl tristearate, and
wherein said oily component (A) and said oily component (B) are used in combination, and wherein the weight ratio of said oily component (A) to said oily component (B) ranges from 5:1 to 10:1.

2. A cosmetic in an emulsified state, as claimed in claim 1, wherein said cosmetic does not contain any one of a cationic surfactant, anionic surfactant, and nonionic surfactant composed of alkylene (carbon atoms: 2 to 4) oxide adduct.

3. A cosmetic in an emulsified state, as claimed in claim 1, wherein said polysaccharide is granulated into random particle diameters.

4. A cosmetic in an emulsified state, as claimed in claim 1, further comprising:
   a titanium dioxide component comprising a surface coated with at least one of hydrous silicic acid and a hydrous silicate compound.

5. A cosmetic in an emulsified state, as claimed in claim 4, wherein the surface of the titanium dioxide component is coated with hydrous silicic acid and a hydrous silicate compound.

6. A cosmetic in an emulsified state, as claimed in claim 4, wherein the surface of the titanium dioxide component is coated with hydrous silicic acid.

* * * * *